United States Patent
Breuer et al.

(10) Patent No.: US 12,298,167 B2
(45) Date of Patent: May 13, 2025

(54) LOW LEVEL WATER SENSOR AND METHOD OF USE

(71) Applicant: FRANKLIN FUELING SYSTEMS, LLC, Madison, WI (US)

(72) Inventors: Todd Breuer, McFarland, WI (US); Vitaliy Demin, Saco, ME (US); Randall Boucher, Saco, ME (US); Adam Main, McFarland, WI (US)

(73) Assignee: FRANKLIN FUELING SYSTEMS, LLC, Madison, WI (US)

( * ) Notice: Subject to any disclaimer, the term of this patent is extended or adjusted under 35 U.S.C. 154(b) by 0 days.

(21) Appl. No.: 17/516,298

(22) Filed: Nov. 1, 2021

(65) Prior Publication Data
US 2022/0136885 A1    May 5, 2022

Related U.S. Application Data

(60) Provisional application No. 63/221,432, filed on Jul. 13, 2021, provisional application No. 63/108,387, filed on Nov. 1, 2020.

(51) Int. Cl.

| | | |
|---|---|---|
| *G01F 23/24* | (2006.01) | |
| *B01D 36/00* | (2006.01) | |
| *B67D 7/76* | (2010.01) | |
| *B67D 7/78* | (2010.01) | |
| *F02M 37/32* | (2019.01) | |
| *G01N 33/28* | (2006.01) | |

(52) U.S. Cl.
CPC ......... *G01F 23/241* (2013.01); *B01D 36/005* (2013.01); *B67D 7/766* (2013.01); *B67D 7/78* (2013.01); *F02M 37/32* (2019.01); *G01N 33/2858* (2013.01)

(58) Field of Classification Search
CPC .......... G01F 23/30; G01F 23/64; G01F 23/72; G01F 23/74; G01F 23/38; G01F 23/241; B01D 36/005; G01N 33/2858
See application file for complete search history.

(56) References Cited

U.S. PATENT DOCUMENTS

| | | | |
|---|---|---|---|
| 3,412,321 | A | 11/1968 | Unterberger et al. |
| 3,793,586 | A | 2/1974 | Heeps |
| 3,950,740 | A | 4/1976 | Greene |
| 4,304,132 | A | 12/1981 | Snaper |

(Continued)

FOREIGN PATENT DOCUMENTS

| | | |
|---|---|---|
| BR | MU8702878 | 10/2009 |
| GB | 1378895 A | 12/1974 |

(Continued)

OTHER PUBLICATIONS

"Tres", (Paul A. Tres's book Designing Plastic Parts for Assembly 2nd, Revised Edition; https://web.archive.org/web/20120125035927/http://engr.bd.psu.edu/pkoch/plasticdesign/snap_design.htm; 2012) (Year: 2012).*

(Continued)

*Primary Examiner* — Kristina M Deherrera
*Assistant Examiner* — Fatemeh Esfandiari Nia
(74) *Attorney, Agent, or Firm* — Faegre Drinker Biddle & Reath LLP

(57) ABSTRACT

A low level water sensor and method of use in, e.g., mitigating acidic corrosion in a fuel storage tank is disclosed.

17 Claims, 51 Drawing Sheets

(56) References Cited

U.S. PATENT DOCUMENTS

| | | |
|---|---|---|
| 4,349,882 A | 9/1982 | Asmundsson et al. |
| 4,419,236 A | 12/1983 | Hsu |
| 4,434,657 A | 3/1984 | Matsumura et al. |
| 4,462,249 A | 7/1984 | Adams |
| 4,589,077 A | 5/1986 | Pope |
| 4,591,946 A | 5/1986 | Pope |
| 4,594,892 A | 6/1986 | Asmundsson |
| 4,601,201 A | 7/1986 | Oota et al. |
| 4,638,305 A | 1/1987 | Sutton |
| 4,648,523 A | 3/1987 | Strock |
| 4,774,680 A | 9/1988 | Agar |
| 4,805,453 A | 2/1989 | Haynes |
| 4,827,246 A | 5/1989 | Dolan et al. |
| 4,861,469 A | 8/1989 | Rossi et al. |
| 4,877,923 A | 10/1989 | Sahakian |
| 5,076,100 A | 12/1991 | Hunter et al. |
| 5,095,933 A * | 3/1992 | Olejak ............... F15B 1/08 137/433 |
| 5,132,923 A | 7/1992 | Crawford et al. |
| 5,319,956 A | 6/1994 | Bogle et al. |
| 5,600,998 A | 2/1997 | Dean |
| 5,767,390 A | 6/1998 | Chapman, IV |
| 5,802,910 A | 9/1998 | Krahn et al. |
| 5,841,825 A | 11/1998 | Roberts |
| 5,950,487 A | 9/1999 | Maresca et al. |
| 6,023,445 A | 2/2000 | Cook et al. |
| 6,182,013 B1 | 1/2001 | Malinverno et al. |
| 7,403,860 B2 | 7/2008 | Hart |
| 7,825,816 B2 | 11/2010 | Jarvie et al. |
| 8,020,438 B2 | 9/2011 | Miskell et al. |
| 8,096,177 B2 | 1/2012 | Burris |
| 8,171,786 B2 | 5/2012 | Burris |
| 8,539,828 B2 | 9/2013 | Prinstil et al. |
| 8,539,829 B2 | 9/2013 | Bardsley et al. |
| 8,555,697 B2 | 10/2013 | Kaya |
| 8,601,867 B2 | 12/2013 | Prinstil et al. |
| 8,656,774 B2 | 2/2014 | Moss |
| 8,770,048 B2 | 7/2014 | Khuzwayo |
| 8,978,464 B2 | 3/2015 | Prinstil |
| 9,037,423 B2 | 5/2015 | Prinstil |
| 9,505,992 B2 | 11/2016 | Vanover et al. |
| 9,557,314 B2 | 1/2017 | Jarvie et al. |
| 9,766,178 B2 | 9/2017 | Pechstedt |
| 10,226,736 B1 | 3/2019 | Cottingham |
| 10,239,745 B2 | 3/2019 | Cornett et al. |
| 10,551,237 B2 | 2/2020 | Cipullo et al. |
| 10,604,402 B2 | 3/2020 | Cloutier |
| 2004/0093942 A1 | 5/2004 | Brun |
| 2006/0169039 A1 | 8/2006 | Zalenski et al. |
| 2006/0248952 A1 | 11/2006 | Jarvie |
| 2011/0187529 A1 | 8/2011 | Maurer et al. |
| 2012/0152016 A1* | 6/2012 | Prinstil ............... G01F 23/68 73/311 |
| 2012/0261437 A1 | 10/2012 | Sabo et al. |
| 2015/0096525 A1* | 4/2015 | Reinhart ............... F02F 7/0073 123/195 C |
| 2016/0281478 A1* | 9/2016 | Brewer ............... E21B 43/127 |
| 2018/0093825 A1 | 4/2018 | Young et al. |
| 2018/0257925 A1 | 9/2018 | Schultz et al. |
| 2019/0062142 A1 | 2/2019 | Bevins et al. |

FOREIGN PATENT DOCUMENTS

| | | | |
|---|---|---|---|
| JP | 2005-076070 A | | 3/2005 |
| JP | 2007107986 A | * | 4/2007 |
| JP | 4152816 B2 | | 9/2008 |
| JP | 5083094 B2 | | 11/2012 |
| JP | 2012-250744 A | | 12/2012 |
| JP | 5610317 B2 | | 10/2014 |
| JP | 5665017 B2 | | 2/2015 |
| JP | 5765637 B2 | | 8/2015 |
| JP | 6265825 B2 | | 1/2018 |
| JP | 6497970 B2 | | 4/2019 |
| JP | 6617115 B2 | | 12/2019 |
| WO | 86/03043 A1 | | 5/1986 |
| WO | 2008/064010 A2 | | 5/2008 |
| WO | 2016/024957 A1 | | 2/2016 |
| WO | 2019/121105 A1 | | 6/2019 |

OTHER PUBLICATIONS

Zytel HTN51G35HSL BK083, High Performance Plyamide Resin, Dupont, dated May 10, 2021, 11 pages.

Skeie, N. O. et al., "Using multi sensor data fusion for level estimation in a separator", Computer Aided Chemical Engineering vol. 21, 2006, pp. 1383-1388.

Casanella et al., "Oil-water interface level sensor based on an electrode array," 2006 IEEE Instrumentation and Measurement Technology Conference Proceedings. IEEE, 2006.

Chen et al., "Real-time estimation of oil quantity in crude oil tanks," IEE Proceedings-Science, Measurement and Technology 153.3 (2006): 108-112.

Khalid et al., "Microwave application for the detection of biodiesel-glycerine and biodiesel-water interfaces in the biodiesel production," Sensors, 2009 IEEE (2009): 631-634.

Li et al., "A method to detect the mixed petrol interface by refractive index measurement with a fiber-optic SPR sensor," IEEE Sensors Journal 14.10 (2014): 3701-3707.

Meribout et al., "Interface layers detection in oil field tanks: a critical review," Expert Systems for Human, Materials and Automation (2011): 181-208.

Sadrolhosseini et al., "Surface plasmon resonance characterization of virgin coconut oil biodiesel: Detection of iron corrosion using polypyrrole chitosan sensing layer," Sensors and materials 24.5 (2012): 221-232.

Skeie et al., "Level estimation in oil/water separators based on multiple pressure sensors and multivariate calibration," Journal of Chemometrics 24 (2010): 387-398.

Yang, "Sensors and instrumentation for monitoring and control of multi-phase separation," Measurement and control 39.6 (2006): 178-184.

Zhang et al., "Water detection in jet fuel using a polymer optical fibre Bragg grating," 20th International Conference on Optical Fibre Sensors. vol. 7503. International Society for Optics and Photonics, 2009.

* cited by examiner

| No. | Control | 23 hours | 80 hours | 130 hours |
|---|---|---|---|---|
| 1 | | | | |
| 2 | | | | |
| 3 | | | | |
| 4 | | | | |
| 5 | | | | |

FIG. 7

LOW LEVEL WATER SENSOR AND METHOD OF USE

CROSS REFERENCE TO RELATED APPLICATIONS

This application is related to U.S. Provisional Patent Application Ser. No. 62/814,428 filed Mar. 6, 2019, U.S. patent application Ser. No. 16/557,363 filed Aug. 30, 2019, U.S. patent application Ser. No. 15/914,535 filed Mar. 7, 2018, U.S. Provisional Patent Application Ser. No. 62/468,033 filed Mar. 7, 2017, U.S., Provisional Patent Application Ser. No. 62/509,506 filed May 22, 2017, U.S., Provisional Patent Application Ser. No. 62/520,891 filed Jun. 16, 2017, U.S., Provisional Patent Application Ser. No. 62/563,596 filed Sep. 26, 2017, U.S., PCT Application No. PCT/US21/37089 filed Jun. 22, 2021, PCT Application No. PCT/US19/49104 filed Aug. 30, 2019, PCT Application No. PCT/US18/21350 filed Mar. 7, 2018, U.S. patent application Ser. No. 17/345,997 filed Jun. 11, 2021, and Provisional Patent Application Ser. No. 63/037,986 filed Jun. 11, 2020. The disclosures of all of the foregoing applications are hereby expressly incorporated by reference herein in their entireties.

This application claims priority to U.S. Provisional Patent Application Ser. No. 63/108,387 filed Nov. 1, 2020 and also claims priority to U.S. Provisional Patent Application Ser. No. 63/221,432 filed Jul. 13, 2021, the disclosures of both of which are hereby expressly incorporated by reference herein in their entireties.

FIELD OF THE DISCLOSURE

The present disclosure relates to a water sensor for sensing the level of water in a fuel storage tank and a method of using such sensor to facilitate appropriate implementation of systems to limit acidic corrosion, and/or to limit the accumulation of water and particulate matter in stored fuel. More particularly, the present disclosure relates to a water sensor particularly adapted to sense very low water levels in fuel storage tanks.

BACKGROUND OF THE DISCLOSURE

A fuel delivery system typically includes one or more underground storage tanks that store various fuel products and one or more fuel dispensers that dispense the fuel products to consumers. The underground storage tanks may be coupled to the fuel dispensers via corresponding underground fuel delivery lines.

In the context of an automobile fuel delivery system, for example, the fuel products may be delivered to consumers' automobiles. In such systems, the fuel products may contain a blend of gasoline and alcohol, specifically ethanol. Blends having about 2.5 vol. % ethanol ("E-2.5"), 5 vol. % ethanol ("E-5"), 10 vol. % ethanol ("E-10"), or more, in some cases up to 85 vol. % ethanol ("E-85"), are now available as fuel for cars and trucks in the United States and abroad. Other fuel products include diesel and biodiesel, for example.

Sumps (i.e., pits) may be provided around the equipment of the fuel delivery system. Such sumps may trap liquids and vapors to prevent environmental releases. Also, such sumps may facilitate access and repairs to the equipment. Sumps may be provided in various locations throughout the fuel delivery system. For example, dispenser sumps may be located beneath the fuel dispensers to provide access to piping, connectors, valves, and other equipment located beneath the fuel dispensers. As another example, turbine sumps may be located above the underground storage tanks to provide access to turbine pump heads, piping, leak detectors, electrical wiring, and other equipment located above the underground storage tanks.

Underground storage tanks and sumps may experience premature corrosion. Efforts have been made to control such corrosion with fuel additives, such as biocides and corrosion inhibitors. However, the fuel additives may be ineffective against certain microbial species, become depleted over time, and cause fouling, for example. Efforts have also been made to control such corrosion with rigorous and time-consuming water maintenance practices, which are typically disfavored by retail fueling station operators.

Water and/or particulate matter sometimes also contaminates the fuel stored in underground storage tanks. Because these contaminants are generally heavier than the fuel product itself, any water or particulate matter found in the storage tank is generally confined to a "layer" of fuel mixed with contaminants at bottom of the tank. Because dispensation of these contaminants may have adverse effects on vehicles or other end-use applications, efforts have been made to timely detect and remediate such contaminants.

SUMMARY

The present disclosure relates to a method and apparatus for controlling a fuel delivery system to limit acidic corrosion. An exemplary control system includes a controller, at least one monitor, an output, and a remediation system. The monitor of the control system may collect and analyze data indicative of a corrosive environment in the fuel delivery system. The output of the control system may automatically warn an operator of the fueling station of the corrosive environment so that the operator can take preventative or corrective action. The remediation system of the control system may take at least one corrective action to remediate the corrosive environment in the fuel delivery system.

The present disclosure further relates to a method and apparatus for filtration of fuel contained in a storage tank, in which activation of a fuel dispensation pump concurrently activates a filtration system. In particular, a portion of pressurized fuel delivered by the dispensation pump is diverted to an eductor designed to create a vacuum by the venturi effect. This vacuum draws fluid from the bottom of the storage tank, at a point lower than the intake for the dispensation pump so that any water or particulate matter at the bottom of the storage tank is delivered to the eductor before it can reach the dispensation pump intake. The eductor delivers a mix of the diverted fuel and the tank-bottom fluid to a filter, where any entrained particulate matter or water is filtered out and removed from the product stream. Clean, filtered fuel is then delivered back to the storage tank.

The present disclosure further provides a probe combining flow and water level detection.

The present disclosure additionally provides a low level water sensor capable of registering low levels of water contamination in a fuel tank.

In another form thereof, the disclosure provides a low-level water float, comprising: a float base; a frame extending upwardly from the float base; and a float magnet spaced a distance from the float base by the frame.

In embodiments, the distance is at least about 3.0 inches.

In embodiments, the low level water float is provided in combination with a magnetostrictive probe shaft, the low-level water float reciprocatable through a float travel on the magnetostrictive probe shaft, the magnetostrictive probe shaft having a datum magnet positioned at a distal end of the magnetostricitve probe shaft, the frame spacing the float magnet a minimum distance from the datum magnet throughout the travel of the low-level water float.

In embodiments, the frame further comprises at least one frame spacer creating a nominal point contact between the low-level water float and the magnetostrictive probe shaft.

In embodiments, the frame comprises a ballast receiver sized to secure at least one ballast to the low-level water float.

In embodiments, the ballast receiver includes a plurality of ballast receiver dimensions including a ballast receiver height, and the at least one ballast has at least one ballast dimension complementary to at least one of the plurality of ballast receiver dimensions.

In embodiments, the low level water float is provided in combination with a magnetostrictive probe shaft having a foot secured to the magnetostrictive probe shaft, the low-level water float reciprocatable along the probe shaft through a float travel, the foot defining an end point of the float travel of the low-level water float, the low-level water float having a foot recess, the foot insertable into the foot recess of the low-level water float, the low-level water float have at least one float foot creating a nominal point contact with the foot when the float is at the end point of travel.

In embodiments, the combination further comprises: a foot secured to the magnetostrictive probe shaft, the foot defining an end point of the float travel of the low-level water float, the low-level water float having a foot recess, the foot insertable into the foot recess of the low-level water float, the low-level water float have at least one float foot creating a nominal point contact with the foot when the float is at the end point of travel.

In a further form thereof, the present disclosure provides a low-level water probe, comprising: a probe shaft; a low-level water float reciprocatable along the probe shaft through a travel; and a foot, the foot defining an end point of the travel of the low-level water float, the low-level water float having a foot recess, the foot insertable into the foot recess of the low-level water float.

In embodiments, the low-level water float comprises at least one float foot creating a nominal point contact with the foot when the float is at the end point of travel.

In embodiments, the probe shaft comprises a magnetostrictive probe shaft and wherein the low-level water float comprises a magnet.

In embodiments, the foot recess has a foot recess inner diameter and the foot has a foot outer diameter, the foot outer diameter smaller than the foot recess inner diameter.

In embodiments, the low-level water float further comprises at least one float spacer creating a nominal point contact between the low-level water float and the magnetostrictive probe shaft.

In a further form thereof, the present disclosure provides a method of configuring a low-level water float for use, comprising: accessing a ballast receiver formed in the low-level water float, the ballast receiver having a plurality of ballast receiver dimensions including a ballast receiver height; testing the buoyancy of the low-level water float relative to a desired buoyancy; and adjusting the buoyancy of the low-level water float by securing to the low-level water float with the ballast receiver at least one ballast having at least one ballast dimension complementary to one of the ballast receiver dimensions.

In embodiments, the testing step comprises testing the buoyancy of the low level water float on a low-level of water, the low level of water comprising a level of water having a depth of ¼ inch.

In embodiments, the adjusting step comprises: detaching a first portion of the water float from a second portion of the water float to provide access to the ballast receiver, wherein the securing step comprises positioning the at least one ballast radially inward of the low-level water float; and attaching the first portion of the water float to the second portion of the water float.

In embodiments, the ballast receiver comprises a cylindrical recess formed in the water float and the ballast receiver dimensions further include a radius, and wherein the adjusting step comprises: detaching a first half of the water float from a second half of the water float to provide access to the ballast receiver, wherein the securing step comprises positioning the at least one ballast radially inward of the low-level water float; and attaching the first portion of the water float to the second portion of the water float.

In embodiments, the ballast dimension comprises a ballast height, and wherein the adjusting step comprises: determining a determined ballast height required to achieve the desired buoyancy.

In embodiments, the securing step comprises: selecting a plurality of ballasts of the at least one ballast having a total height substantially equal to the determined ballast height.

In a further form thereof, the disclosure provides a low-level water float, comprising: a float body comprising a ballast receiver including a plurality of ballast receiver dimensions including a ballast receiver height; and at least one ballast having at least one ballast dimension complementary to at least one of the plurality of ballast receiver dimensions, the ballast secured by the ballast receiver.

According to an embodiment of the present disclosure, a fuel delivery system is provided including a storage tank containing a fuel product, a fuel delivery line in communication with the storage tank, at least one monitor that collects data indicative of a corrosive environment in the fuel delivery system, a controller in communication with the at least one monitor to receive collected data from the at least one monitor, and a remediation system configured to take at least one corrective action to remediate the corrosive environment when activated by the controller in response to the collected data.

According to another embodiment of the present disclosure, a fuel delivery system is provided including a storage tank containing a fuel product, a fuel delivery line in communication with the storage tank, a monitor including a light source, a corrosive target material exposed to a corrosive environment in the fuel delivery system, and a detector configured to detect light from the light source through the target material, and a controller in communication with the monitor.

According to yet another embodiment of the present disclosure, a fuel delivery system is provided including a storage tank containing a fuel product, a sump, a pump having a first portion positioned in the sump and a second portion positioned in the storage tank, and a water filtration system. The water filtration system includes a water filter positioned in the sump and configured to separate the fuel product into a filtered fuel product and a separated water product, a fuel inlet passageway in fluid communication with the storage tank and the water filter via the pump to direct the fuel product to the water filter, a fuel return passageway in fluid communication with the water filter and the storage tank to return the filtered fuel product to the storage tank, and a water removal passageway in fluid communication with the water filter to drain the separated water product from the water filter.

According to still another embodiment of the present disclosure, a fuel delivery system is provided including a water filtration system. The water filtration system includes a filter configured to separate a fuel product into a filtered fuel product and a separated water product, an eductor configured to receive a flow of fuel from a fuel delivery pump and send the flow of fuel to the filter, and a vacuum port on the eductor configured to be operably connected to a source of contaminated fuel, such that the vacuum port draws the contaminated fuel into the flow of fuel through the eductor and delivers a mixture of fuel and contaminated fuel to the filter.

According to still another embodiment of the present disclosure, a fuel delivery system is disclosed including a storage tank containing a fuel product, a dispenser, a water filter, a fuel uptake line in fluid communication with the storage tank and the dispenser to deliver the fuel product to the dispenser, a filtration uptake line in fluid communication with the storage tank and the water filter to deliver the fuel product to the water filter, the water filter being configured to separate the fuel product into a filtered fuel product and a separated water product, a fuel return passageway in fluid communication with the water filter and the storage tank to return the filtered fuel product to the storage tank, and a water removal passageway in fluid communication with the water filter to drain the separated water product from the water filter.

According to another embodiment, a probe is disclosed, the probe comprising: a water float buoyant on a quantity of water; a probe shaft having a longitudinal axis, the water float restrained for displacement along a longitudinal axis of the probe shaft, the probe capable of communicating a position of the water float along the probe shaft to signal an amount of the quantity of water; an isolator fixed along the longitudinal axis of the probe shaft, whereby the isolator maintains a fixed position relative to the probe shaft along the longitudinal axis of the probe shaft; a flow sensing shuttle restrained by the probe shaft for displacement along the longitudinal axis of the probe shaft, the isolator interposed between the water float and the flow sensing shuttle, whereby the isolator isolates the flow sensing shuttle from the water float; and a stop secured to the probe shaft, the flow sensing shuttle displaceable along the longitudinal axis of the probe shaft between the isolator and the stop; the flow sensing shuttle moveable by a fluid flow between a no-flow position and a flow position, the probe capable of communicating the presence of the fluid flow in the flow position, the probe capable of communicating the absence of the fluid flow in the no-flow position.

According to yet another embodiment, a probe is disclosed, the probe comprising: a probe shaft; a flow sensing shuttle restrained by the probe shaft for displacement along the longitudinal axis of the probe shaft; the flow sensing shuttle displaceable along the longitudinal axis of the probe shaft; the flow sensing shuttle moveable by a fluid defining a fluid flow, the flow sensing shuttle is not buoyant on the fluid, the flow sensing shuttle moveable by a fluid flow along a flow sensing shuttle travel between a no-flow position and a flow position, the probe capable of communicating the presence of the fluid flow in the flow position, the probe capable of communicating the absence of the fluid flow in the no-flow position.

According to a further yet embodiment, a prove is disclosed, the probe comprising: a water float buoyant on a quantity of water, the water float having a retracted position defining a retracted float width, the water float having an extended position defining an extended float width greater than the retracted float width; and a probe shaft having a longitudinal axis, the water float restrained for displacement along a longitudinal axis of the probe shaft, the probe capable of communicating a position of the water float along the probe shaft to signal an amount of the quantity of water.

According to an additional embodiment, a method of mitigating acidic corrosion in a fuel storage tank is provided, the method comprising: measuring a low level of water in the fuel storage tank, the low level of water defining a layer of water having a height of less than 1 inch from a floor of the fuel storage tank; and employing an acetic corrosion mitigation system to remove the layer of water responsive to measuring the low level of water in the fuel storage tank.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein:

FIG. 7 includes photographs of the corrosive samples tested in Example 1;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
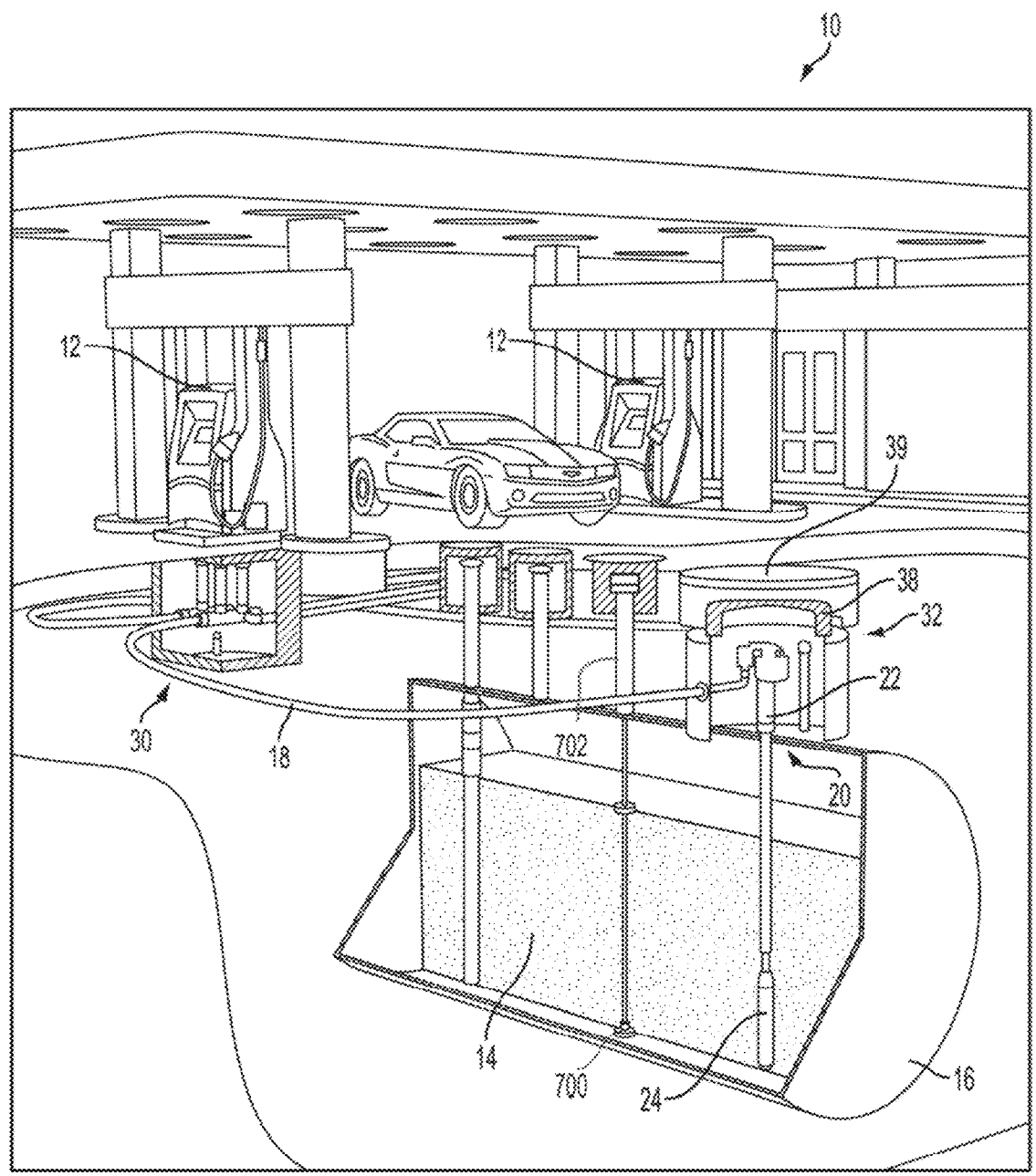
FIG. 1 depicts an exemplary fuel delivery system of the present disclosure showing above ground components, such as a fuel dispenser, and below ground components, such as a storage tank containing a fuel product, a fuel delivery line, a turbine sump, and a dispenser sump.

An exemplary fuel delivery system 10 is shown in FIG. 1. Fuel delivery system 10 includes a fuel dispenser 12 for dispensing a liquid fuel product 14 from a liquid storage tank 16 to consumers. Each storage tank 16 is fluidly coupled to one or more dispensers 12 via a corresponding fuel delivery line 18. Storage tank 16 and delivery line 18 are illustratively positioned underground, but it is also within the scope of the present disclosure that storage tank 16 and/or delivery line 18 may be positioned above ground.

Fuel delivery system 10 of FIG. 1 also includes a pump 20 to draw fuel product 14 from storage tank 16 and to convey fuel product 14 through delivery line 18 to dispenser 12. Pump 20 is illustratively a submersible turbine pump ("STP") having a turbine pump head 22 located above storage tank 16 and a submersible motor 24 located inside storage tank 16. However, it is within the scope of the present disclosure that other types of pumps may be used to transport fuel product 14 through fuel delivery system 10.

Figure 2:
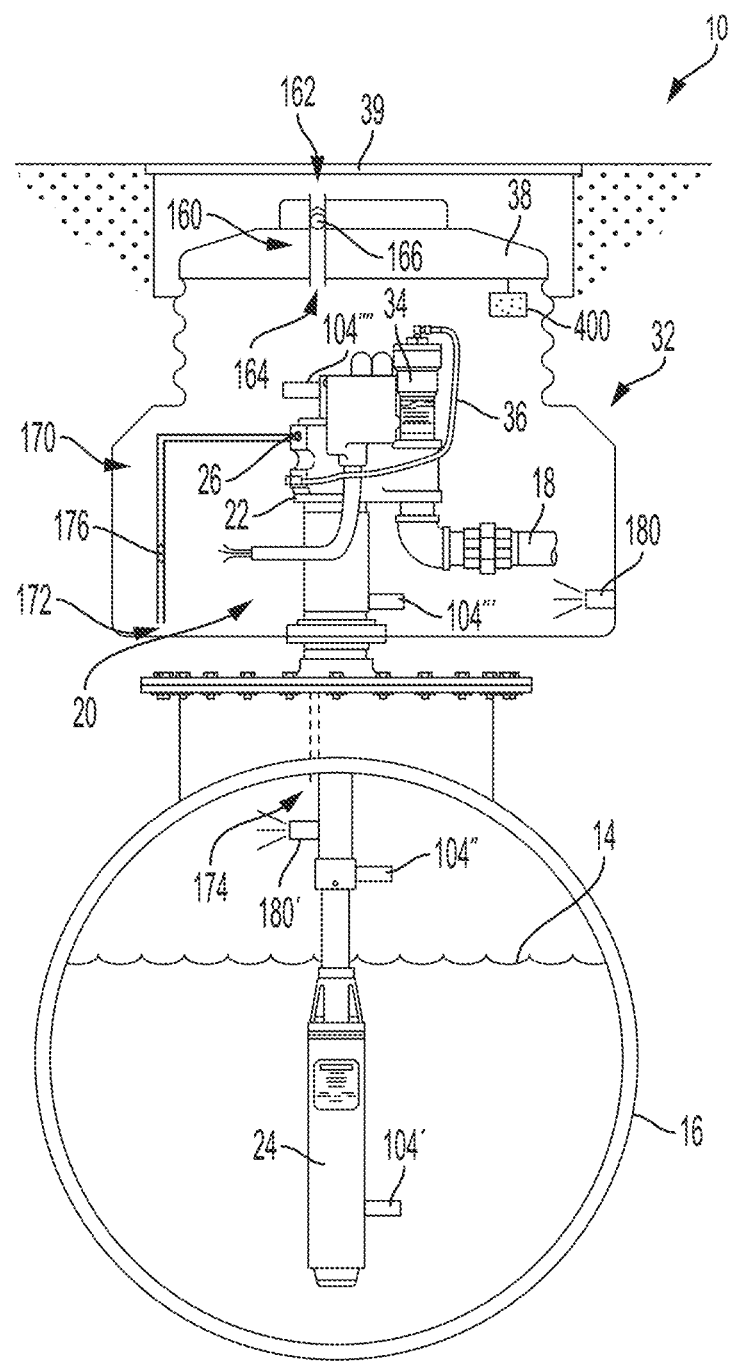
FIG. 2 is a cross-sectional view of the storage tank and the turbine sump of FIG. 1.

Fuel delivery system 10 of FIG. 1 further includes various underground sumps (i.e., pits). A first, dispenser sump 30 is provided beneath dispenser 12 to protect and provide access to piping (e.g., delivery line 18), connectors, valves, and other equipment located therein, and to contain any materials that may be released beneath dispenser 12. A second, turbine sump 32, which is also shown in FIG. 2, is provided above storage tank 16 to protect and provide access to pump 20, piping (e.g., delivery line 18), leak detector 34, electrical wiring 36, and other equipment located therein. Turbine sump 32 is illustratively capped with an underground lid 38 and a ground-level manhole cover 39, which protect the equipment inside turbine sump 32 when installed and allow access to the equipment inside turbine sump 32 when removed.

According to an exemplary embodiment of the present disclosure, fuel delivery system 10 is an automobile fuel delivery system. In this embodiment, fuel product 14 may be a gasoline/ethanol blend that is delivered to consumers' automobiles, for example. The concentration of ethanol in the gasoline/ethanol blended fuel product 14 may vary from 0 vol. % to 15 vol. % or more. For example, fuel product 14 may contain about 2.5 vol. % ethanol ("E-2.5"), about 5 vol. % ethanol ("E-5"), about 7.5 vol. % ethanol ("E-7.5"), about 10 vol. % ethanol ("E-10"), about 15 vol. % ethanol ("E-15"), or more, in some cases up to about 85 vol. % ethanol ("E-85"). As discussed in U.S. Publication No. 2012/0261437, the disclosure of which is expressly incorporated herein by reference in its entirety, the ethanol may attract water into the gasoline/ethanol blended fuel product 14. The water in fuel product 14 may be present in a dissolved state, an emulsified state, or a free water state. Eventually, the water may also cause phase separation of fuel product 14.

In addition to being present in storage tank 16 as part of the gasoline/ethanol blended fuel product 14, ethanol may find its way into other locations of fuel delivery system 10 in a vapor or liquid state, including dispenser sump 30 and turbine sump 32. In the event of a fluid leak from dispenser 12, for example, some of the gasoline/ethanol blended fuel product 14 may drip from dispenser 12 into dispenser sump 30 in a liquid state. Also, in the event of a vapor leak from storage tank 16, vapor in the ullage of storage tank 16 may escape from storage tank 16 and travel into turbine sump 32. In certain situations, turbine sump 32 and/or components contained therein (e.g., metal fittings, metal valves, metal plates) may be sufficiently cool in temperature to condense the ethanol vapor back into a liquid state in turbine sump 32. Along with ethanol, water from the surrounding soil, fuel product 14, or another source may also find its way into sumps 30, 32 in a vapor or liquid state, such as by dripping into sumps 30, 32 in a liquid state or by evaporating and then condensing in sumps 30, 32. Ethanol and/or water leaks into sumps 30, 32 may occur through various connection points in sumps 30, 32, for example. Ethanol and/or water may escape from ventilated sumps 30, 32 but may become trapped in unventilated sumps 30, 32.

In the presence of certain bacteria and water, ethanol that is present in fuel delivery system 10 may be oxidized to produce acetate, according to Reaction I below.

$$CH_3CH_2OH+H_2O \rightarrow CH_3COO^-+H^++2H_2 \quad (I)$$

The acetate may then be protonated to produce acetic acid, according to Reaction II below.

$$CH_3COO^-+H^+ \rightarrow CH_3COOH \quad (II)$$

The conversion of ethanol to acetic acid may also occur in the presence of oxygen according to Reaction III below.

$$2CH_3CH_2OH+O_2 \rightarrow 2CH_3COOH+2H_2O \quad (III)$$

Acetic acid producing bacteria or AAB may produce acetate and acetic acid by a metabolic fermentation process, which is used commercially to produce vinegar, for example. Acetic acid producing bacteria generally belong to the Acetobacteraceae family, which includes the genera *Acetobacter*, *Gluconobacter*, and *Gluconacetobacter*. Acetic acid producing bacteria are very prevalent in nature and may be present in the soil around fuel delivery system 10, for example. Such bacteria may find their way into sumps 30, 32 to drive Reactions I-III above, such as when soil or debris falls into sumps 30, 32 or when rainwater seeps into sumps 30, 32.

The products of Reactions I-III above may reach equilibrium in sumps 30, 32, with some of the acetate and acetic acid dissolving into liquid water that is present in sumps 30, 32, and some of the acetate and acetic acid volatilizing into a vapor state. In general, the amount acetate or acetic acid that is present in the vapor state is proportional to the amount of acetate or acetic acid that is present in the liquid state (i.e, the more acetate or acetic acid that is present in the vapor state, the more acetate or acetic acid that is present in the liquid state).

Even though acetic acid is classified as a weak acid, it may be corrosive to fuel delivery system 10, especially at high concentrations. For example, the acetic acid may react to deposit metal oxides (e.g., rust) or metal acetates on metallic fittings of fuel delivery system 10. Because Reactions I-III are microbiologically-influenced reactions, these deposits in fuel delivery system 10 may be tubular or globular in shape.

Figure 3:
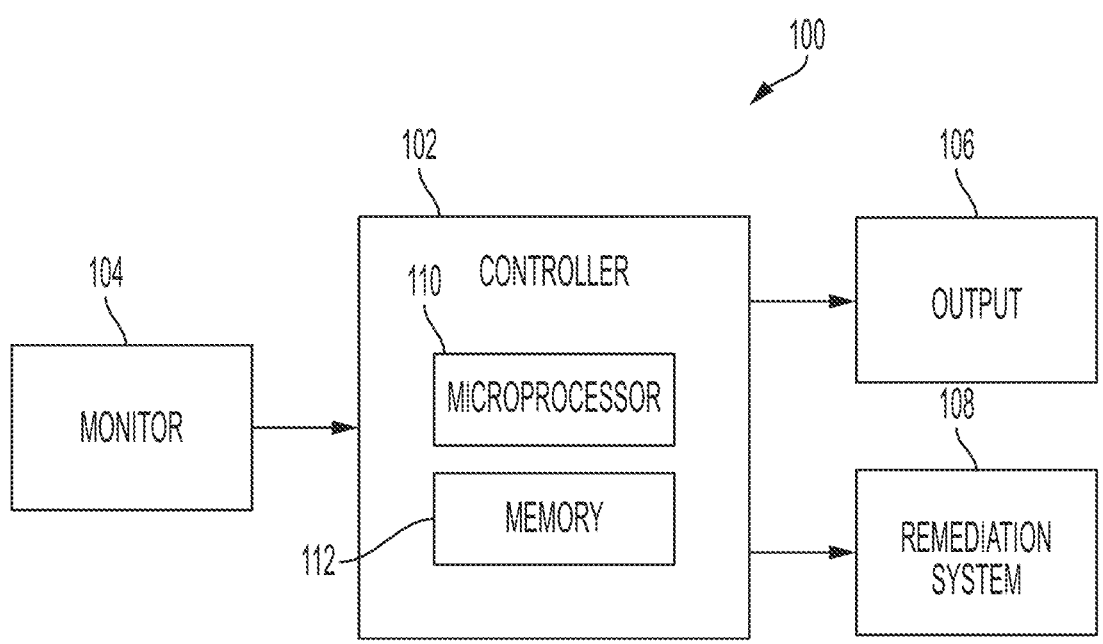
FIG. 3 is a schematic view of an exemplary control system of the present disclosure, the control system including a controller, at least one monitor, an output, and a remediation system.

To limit corrosion in fuel delivery system 10, a control system 100 and a corresponding monitoring method are provided herein. As shown in FIG. 3, the illustrative control system 100 includes controller 102, one or more monitors 104 in communication with controller 102, output 106 in communication with controller 102, and remediation system 108 in communication with controller 102, each of which is described further below.

Controller 102 of control system 100 illustratively includes a microprocessor 110 (e.g., a central processing unit (CPU)) and an associated memory 112. Controller 102 may be any type of computing device capable of accessing a computer-readable medium having one or more sets of instructions (e.g., software code) stored therein and executing the instructions to perform one or more of the sequences, methodologies, procedures, or functions described herein. In general, controller 102 may access and execute the instructions to collect, sort, and/or analyze data from monitor 104, determine an appropriate response, and communicate the response to output 106 and/or remediation system 108. Controller 102 is not limited to being a single computing device, but rather may be a collection of computing devices (e.g., a collection of computing devices accessible over a network) which together execute the instructions. The instructions and a suitable operating system for executing the instructions may reside within memory 112 of controller 102, for example. Memory 112 may also be configured to store real-time and historical data and measurements from monitors 104, as well as reference data. Memory 112 may store information in database arrangements, such as arrays and look-up tables.

Controller 102 of control system 100 may be part of a larger controller that controls the rest of fuel delivery system 10. In this embodiment, controller 102 may be capable of operating and communicating with other components of fuel delivery system 10, such as dispenser 12 (FIG. 1), pump 20 (FIG. 2), and leak detector 34 (FIG. 2), for example. An exemplary controller 102 is the TS-550 Evo® Fuel Management System available from Franklin Fueling Systems Inc. of Madison, Wis.

Monitor 104 of control system 100 is configured to automatically and routinely collect data indicative of a corrosive environment in fuel delivery system 10. In operation, monitor 104 may draw in a liquid or vapor sample from fuel delivery system 10 and directly test the sample or test a target material that has been exposed to the sample, for example. In certain embodiments, monitor 104 operates continuously, collecting samples and measuring data approximately once every second or minute, for example. Monitor 104 is also configured to communicate the collected data to controller 102. In certain embodiments, monitor 104 manipulates the data before sending the data to controller 102. In other embodiments, monitor 104 sends the data to controller 102 in raw form for manipulation by controller 102. The illustrative monitor 104 is wired to controller 102, but it is also within the scope of the present disclosure that monitor 104 may communicate wirelessly (e.g., via an internet network) with controller 102.

Depending on the type of data being collected by each monitor 104, the location of each monitor 104 in fuel delivery system 10 may vary. Returning to the illustrated embodiment of FIG. 2, for example, monitor 104' is positioned in the liquid space (e.g., middle or bottom) of storage tank 16 to collect data regarding the liquid fuel product 14 in storage tank 16, monitor 104" is positioned in the ullage or vapor space (i.e., top) of storage tank 16 to collect data regarding any vapors present in storage tank 16, monitor 104''' is positioned in the liquid space (i.e., bottom) of turbine sump 32 to collect data regarding any liquids present in turbine sump 32, and monitor 104'''' is positioned in the vapor space (i.e., top) of turbine sump 32 to collect data regarding any vapors present in turbine sump 32. Monitor 104 may be positioned in other suitable locations of fuel delivery system 10, including delivery line 18 and dispenser sump 30 (FIG. 1), for example. Various monitors 104 for use in control system 100 of FIG. 3 are discussed further below.

Output 106 of control system 100 may be capable of communicating an alarm or warning from controller 102 to an operator. Output 106 may include a visual indication device (e.g., a gauge, a display screen, lights, a printer), an audio indication device (e.g., a speaker, an audible alarm), a tactile indication device, or another suitable device for communicating information to the operator, as well as combinations thereof. Controller 102 may transmit information to output 106 in real-time, or controller 102 may store information in memory 112 for subsequent transmission or download to output 106.

Remediation system 108 of control system 100 may be capable of taking at least one corrective action to remediate the corrosive environment in fuel delivery system 10. Various embodiments of remediation system 108 are described below.

The illustrative output 106 and remediation system 108 are wired to controller 102, but it is also within the scope of the present disclosure that output 106 and/or remediation system 108 may communicate wirelessly (e.g., via an internet network) with controller 102. For example, to facilitate communication between output 106 and the operator, output 106 may be located in the operator's control room or office.

In operation, and as discussed above, controller 102 collects, sorts, and/or analyzes data from monitor 104, determines an appropriate response, and communicates the response to output 106 and/or remediation system 108. According to an exemplary embodiment of the present disclosure, output 106 warns the operator of a corrosive environment in fuel delivery system 10 and/or remediation system 108 takes corrective action before the occurrence of any corrosion or any significant corrosion in fuel delivery system 10. In this embodiment, corrosion may be prevented or minimized. It is also within the scope of the present disclosure that output 106 may alert the operator to the occurrence of corrosion in fuel delivery system 10 and/or remediation system 108 may take corrective action to at least avoid further corrosion.

Various factors may influence whether controller 102 issues an alarm or warning from output 106 that a corrosive environment is present in fuel delivery system 10 or becoming more likely to develop. Similar factors may also influence whether controller 102 instructs remediation system 108 to take corrective action in response to the corrosive environment. As discussed further below, these factors may be evaluated based on data obtained from one or more monitors 104.

One factor indicative of a corrosive environment includes the concentration of acidic molecules in fuel delivery system 10, with controller 102 issuing an alarm or warning from output 106 and/or activating remediation system 108 when the measured concentration of acidic molecules in fuel delivery system 10 exceeds an acceptable concentration of acidic molecules in fuel delivery system 10. The concentration may be expressed in various units. For example, controller 102 may activate output 106 and/or remediation system 108 when the measured concentration of acidic molecules in fuel delivery system 10 exceeds 25 ppm, 50 ppm, 100 ppm, 150 ppm, 200 ppm, or more, or when the measured concentration of acidic molecules in fuel delivery system 10 exceeds 25 mg/L, 50 mg/L, 100 mg/L, 150 mg/L, 200 mg/L, or more. At or beneath the acceptable concentration, corrosion in fuel delivery system 10 may be limited. Controller 102 may also issue an alarm or warning from output 106 and/or activate remediation system 108 when the concentration of acidic molecules increases at an undesirably high rate.

Another factor indicative of a corrosive environment includes the concentration of hydrogen ions in fuel delivery system 10, with controller 102 issuing an alarm or warning from output 106 and/or activating remediation system 108 when the measured concentration of hydrogen ions in fuel delivery system 10 exceeds an acceptable concentration of hydrogen ions in fuel delivery system 10. For example, controller 102 may activate output 106 and/or remediation system 108 when the hydrogen ion concentration causes the pH in fuel delivery system 10 to drop below 5, 4, 3, or 2, for example. Within the acceptable pH range, corrosion in fuel delivery system 10 may be limited. Controller 102 may also issue an alarm or warning from output 106 and/or activate remediation system 108 when the concentration of hydrogen ions increases at an undesirably high rate.

Yet another factor indicative of a corrosive environment includes the concentration of bacteria in fuel delivery system 10, with controller 102 issuing an alarm or warning from output 106 and/or activating remediation system 108 when the measured concentration of bacteria in fuel delivery system 10 exceeds an acceptable concentration of bacteria in fuel delivery system 10. At or beneath the acceptable concentration, the production of corrosive materials in fuel delivery system 10 may be limited. Controller 102 may also issue an alarm or warning from output 106 and/or activate remediation system 108 when the concentration of bacteria increases at an undesirably high rate.

Yet another factor indicative of a corrosive environment includes the concentration of water in fuel delivery system 10, with controller 102 issuing an alarm or warning from output 106 and/or activating remediation system 108 when the measured concentration of water in fuel delivery system 10 exceeds an acceptable concentration of water in fuel delivery system 10. At or beneath the acceptable concentration, the production of corrosive materials in fuel delivery system 10 may be limited. Controller 102 may also issue an alarm or warning from output 106 and/or activate remediation system 108 when the concentration of water increases at an undesirably high rate. The water may be present in liquid and/or vapor form. Liquid water in storage tank 16 may be measured with the low level water sensor described hereinbelow.

Controller 102 may be programmed to progressively vary the alarm or warning communication from output 106 as the risk of corrosion in fuel delivery system 10 increases. For example, controller 102 may automatically trigger: a minor alarm (e.g., a blinking light) when monitor 104 detects a relatively low acid concentration level (e.g., 5 ppm) in fuel delivery system 10 or a relatively steady acid concentration level over time; a moderate alarm (e.g., an audible alarm) when monitor 104 detects a moderate acid concentration level (e.g., 10 ppm) in fuel delivery system 10 or a moderate increase in the acid concentration level over time; and a severe alarm (e.g., a telephone call or an e-mail to the gas station operator) when monitor 104 detects a relatively high acid concentration level (e.g., 25 ppm) in fuel delivery system 10 or a relatively high increase in the acid concentration level over time.

The alarm or warning communication from output 106 allows the operator to manually take precautionary or corrective measures to limit corrosion of fuel delivery system 10. For example, if an alarm or warning communication is signaled from turbine sump 32 (FIG. 2), the operator may remove manhole cover 39 and lid 38 to clean turbine sump 32, which may involve removing bacteria and potentially corrosive liquids and vapors from turbine sump 32. As another example, the operator may inspect fuel delivery system 10 for a liquid leak or a vapor leak that allowed ethanol and/or its acidic reaction products to enter turbine sump 32 in the first place.

Even if no immediate action is required, the alarm or warning communication from output 106 may allow the operator to better plan for and predict when such action may become necessary. For example, the minor alarm from output 106 may indicate that service should be performed within about 2 months, the moderate alarm from output 106 may indicate that service should be performed within about 1 month, and the severe alarm from output 106 may indicate that service should be performed within about 1 week.

As discussed above, control system 100 includes one or more monitors 104 that collect data indicative of a corrosive environment in fuel delivery system 10. Each monitor 104 may vary in the type of data that is collected, the type of sample that is evaluated for testing, and the location of the sample that is evaluated for testing, as exemplified below.

Figure 4:
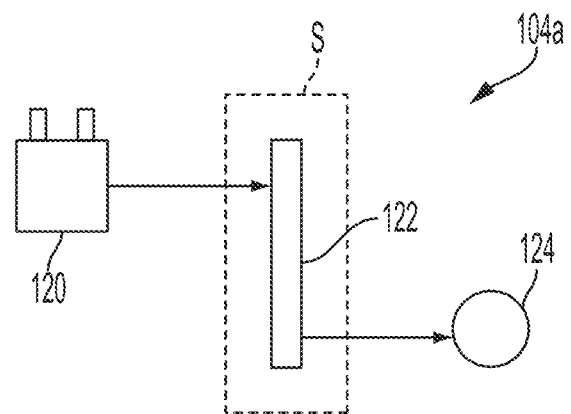
FIG. 4 is a schematic view of a first exemplary electrical monitor for use in the control system of FIG. 3.

In one embodiment, monitor 104 collects electrical data indicative of a corrosive environment in fuel delivery system 10. An exemplary electrical monitor 104a is shown in FIG. 4 and includes an energy source 120, a corrosive target material 122 that is exposed to a liquid or vapor sample S from fuel delivery system 10, and a sensor 124. To enhance the longevity of monitor 104a, energy source 120 and/or sensor 124 may be protected from any corrosive environment in fuel delivery system 10, unlike target material 122. Target material 122 may be designed to corrode before the equipment of fuel delivery system 10 corrodes. Target material 122 may be constructed of or coated with a material that is susceptible to acidic corrosion, such as copper or low carbon steel. Also, target material 122 may be relatively thin or small in size compared to the equipment of fuel delivery system 10 such that even a small amount of corrosion will impact the structural integrity of target material 122. For example, target material 122 may be in the form of a thin film or wire.

In use, energy source 120 directs an electrical current through target material 122. When target material 122 is intact, sensor 124 senses the electrical current traveling through target material 122. However, when exposure to sample S causes target material 122 to corrode and potentially break, sensor 124 will sense a decreased electrical current, or no current, traveling through target material 122. It is also within the scope of the present disclosure that the corrosion and/or breakage of target material 122 may be detected visually, such as by using a camera as sensor 124. First monitor 104a may share the data collected by sensor 124 with controller 102 (FIG. 3) to signal a corrosive environment in fuel delivery system 10 when the electrical current reaches an undesirable level or changes at an undesirable rate, for example. After use, the corroded target material 122 may be discarded and replaced.

Figure 5:
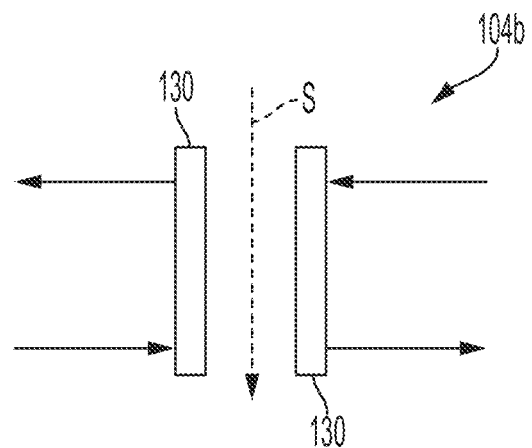
FIG. 5 is a schematic view of a second exemplary electrical monitor for use in the control system of FIG. 3.

Another exemplary electrical monitor 104b is shown in FIG. 5 and includes opposing, charged metal plates 130. The electrical monitor 104b operates by measuring electrical properties (e.g., capacitance, impedance) of a liquid or vapor sample S that has been withdrawn from fuel delivery system 10. In the case of a capacitance monitor 104b, for example, the sample S is directed between plates 130. Knowing the size of plates 130 and the distance between plates 130, the dielectric constant of the sample S may be calculated. As the quantity of acetate, acetic acid, and/or water in the sample S varies, the dielectric constant of the sample S may also vary. The electrical monitor 104b may share the collected data with controller 102 (FIG. 3) to signal a corrosive environment in fuel delivery system 10 when the dielectric constant reaches an undesirable level or changes at an undesirable rate, for example. One example of electrical monitor 104b is a water content monitor that may be used to monitor the water content of fuel product 14 or another sample S from fuel delivery system 10. An exemplary water content monitor is the ICM-W monitor available from MP Filtri, which uses a capacitive sensor to measure the relative humidity (RH) of the tested fluid. As the RH increases toward a saturation point, the water in the fluid may transition from a dissolved state, to an emulsified state, to a free water state. Other exemplary water content monitors are described in the above-incorporated U.S. Publication No. 2012/0261437. Another example of electrical monitor 104b is a humidity sensor that may be used to monitor the humidity in the vapor space of storage tank 16 and/or turbine sump 32.

In another embodiment, monitor 104 collects elecro-chemical data indicative of a corrosive environment in fuel delivery system 10. An exemplary electrochemical monitor (not shown) performs potentiometric titration of a sample that has been withdrawn from fuel delivery system 10. A suitable potentiometric titration device includes an electrochemical cell with an indicator electrode and a reference electrode that maintains a consistent electrical potential. As a titrant is added to the sample and the electrodes interact with the sample, the electric potential across the sample is measured. Potentiometric or chronopotentiometric sensors, which may be based on solid-state reversible oxide films, such as that of iridium, may be used to measure potential in the cell. As the concentration of acetate or acetic acid in the sample varies, the potential may also vary. The potentiometric titration device may share the collected data with controller 102 (FIG. 3) to signal a corrosive environment in fuel delivery system 10 when the potential reaches an undesirable level or changes at an undesirable rate, for example. An electrochemical monitor may also operate by exposing the sample to an electrode, performing a reduction-oxidation with the sample at the electrode, and measuring the resulting current, for example.

Figure 6:
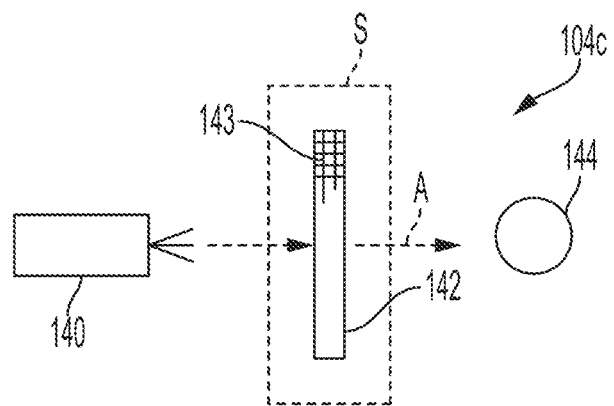
FIG. 6 is a schematic view of a third exemplary optical monitor for use in the control system of FIG. 3.

In yet another embodiment, monitor 104 collects optical data indicative of a corrosive environment in fuel delivery system 10. An exemplary optical monitor 104c is shown in FIG. 6 and includes a light source 140 (e.g., LED, laser), an optical target material 142 that is exposed to a liquid or vapor sample S from fuel delivery system 10, and an optical detector 144 (e.g., photosensor, camera). To enhance the safety of monitor 104c, light source 140 may be a low-energy and high-output device, such as a green LED. Target material 142 may be constructed of or coated with a material (e.g., an acid-sensitive polymer) that changes optical properties (e.g., color, transmitted light intensity) in the presence of the sample S.

Optical monitor 104c may enable real-time, continuous monitoring of fuel delivery system 10 by installing light source 140, target material 142, and detector 144 together in fuel delivery system 10. To enhance the longevity of this real-time monitor 104c, light source 140 and/or detector 144 may be protected from any corrosive environment in fuel delivery system 10, unlike target material 142. For example, light source 140 and/or detector 144 may be contained in a sealed housing, whereas target material 142 may be exposed to the surrounding environment in fuel delivery system 10.

Alternatively, optical monitor 104c may enable manual, periodic monitoring of fuel delivery system 10. During exposure, target material 142 may be installed alone in fuel delivery system 10. During testing, target material 142 may be periodically removed from fuel delivery system 10 and positioned between light source 140 and detector 144. In a first embodiment of the manual monitor 104c, light source 140 and detector 144 may be sold as a stand-alone, hand-held unit that is configured to receive the removed target material 142. In a second embodiment of the manual monitor 104c, light source 140 may be sold along with a software application to convert the operator's own smartphone or mobile device into a suitable detecor 144. Detector 144 of monitor 104c may transmit information to controller 102 (FIG. 3) in real-time or store information in memory for subsequent transmission or download.

One suitable target material 142 includes a pH indicator that changes color when target material 142 is exposed to an acidic pH with $H^+$ protons, such as a pH less than about 5, 4, 3, or 2, for example. The optical properties of target material 142 may be configured to change before the equipment of fuel delivery system 10 corrodes. Detector 144 may use optical fibers as the sensing element (i.e., intrinsic sensors) or as a means of relaying signals to a remote sensing element (i.e., extrinsic sensors).

In use, light source 140 directs a beam of light toward target material 142. Before target material 142 changes color, for example, detector 144 may detect a certain reflection, transmission (i.e., spectrophotometry), absorbtion (i.e., densitometry), and/or refraction of the light beam from target material 142. However, after target material 142 changes color, detector 144 will detect a different reflection, transmission, absorbtion, and/or refraction of the light beam. It is also within the scope of the present disclosure that the changes in target material 142 may be detected visually, such as by using a camera (e.g., a smartphone camera) as detector 144. Third monitor 104c may share the data collected by detector 144 with controller 102 (FIG. 3) to signal a corrosive environment in fuel delivery system 10 when the color reaches an undesirable level or changes at an undesirable rate, for example.

Another suitable target material 142 includes a sacrificial, corrosive material that corrodes (e.g., rusts) when exposed to a corrosive environment in fuel delivery system 10. For example, the corrosive target material 142 may include copper or low carbon steel. The corrosive target material 142 may have a high surface area to volume ratio to provide detector 144 with a large and reliable sample size. For example, as shown in FIG. 6, the corrosive target material 142 may be in the form of a woven mesh or perforated sheet having a large plurality of pores 143.

In use, light source 140 directs a beam of light along an axis A toward the corrosive target material 142. Before target material 142 corrodes, detector 144 may detect a certain amount of light that passes from the light source 140 and through the open pores 143 of the illuminated target material 142 along the same axis A. However, as target material 142 corrodes, the material may visibly swell as rust accumulates in and around some or all of the pores 143. This accumulating rust may obstruct or prevent light from traveling through pores 143, so detector 144 (e.g., a photodiode) will detect a decreasing amount of light through the corroding target material 142. It is also within the scope of the present disclosure that the changes in target material 142 may be detected visually, such as by using a camera or another suitable imaging device as detector 144. Detector 144 may capture an image of the illuminated target material 142 and then evaluate the image (e.g., pixels of the image) for transmitted light intensity, specific light patterns, etc. As discussed above, third monitor 104c may share the data collected by detector 144 with controller 102 (FIG. 3) to signal a corrosive environment in fuel delivery system 10 when the transmitted light intensity reaches an undesirable level or changes at an undesirable rate, for example. After use, the corroded target material 142 may be discarded and replaced.

Another exemplary optical monitor 104c' is shown in FIGS. 16-19. Optical monitor 104c' of FIGS. 16-19 is similar to optical monitor 104c of FIG. 6 and includes several components and features in common with optical monitor 104c as indicated by the use of common reference numbers between optical monitors 104c, 104c', including a light source 140', a corrosive target material 142', and an optical detector 144'. Optical monitor 104c' may be mounted in the vapor space of storage tank 16 and/or turbine sump 32 of fuel delivery system 10 (FIG. 2).

The illustrative optical monitor 104c' is generally cylindrical in shape and has a longitudinal axis L. In the illustrated embodiment of FIG. 19, light source 140' and target material 142' are located on a first side of axis L (illustratively the right side of axis L), and optical detector 144' is located on a second side of axis L (illustratively the left side of axis L). Light source 140' and optical detector 144' are substantially coplanar and are located above target material 142'. The illustrative target material 142' is a L-shaped mesh sheet, with a vertical portion 145a' of target material 142' extending parallel to axis L and a horizontal portion 145b' of target material 142' extending perpendicular to axis L.

Figure 19:
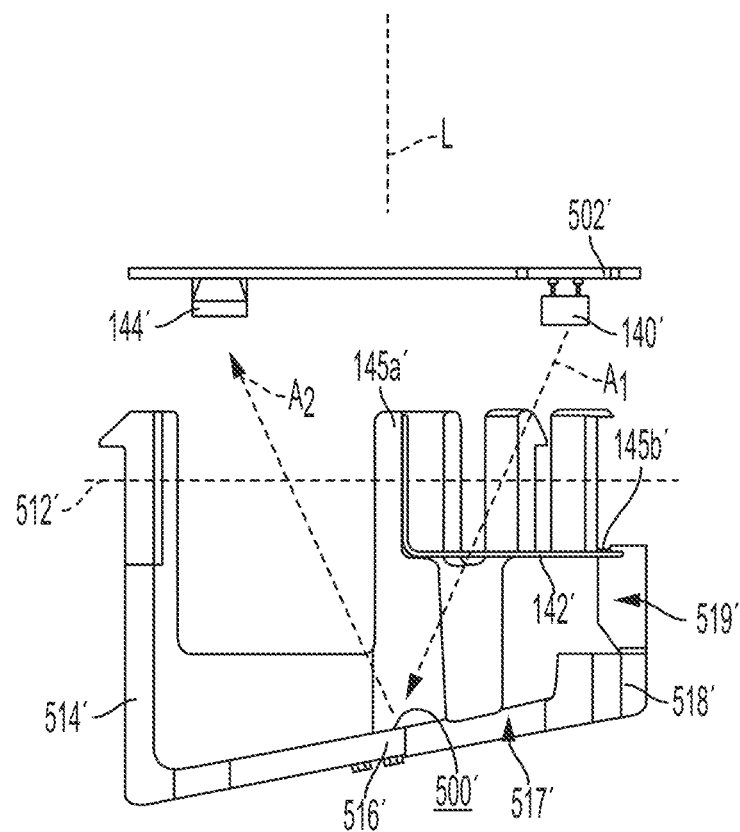
FIG. 19 is a partial cross-sectional view of the optical monitor of FIG. 16.

The illustrative optical monitor 104c' includes a reflective surface 500' positioned downstream of light source 140' and upstream of optical detector 144', wherein the reflective surface 500' is configured to reflect incident light from light source 140' toward optical detector 144'. In the illustrated embodiment of FIG. 19, the incident light from light source 140' travels downward and inward toward axis L along a first axis $A_1$ toward reflective surface 500', and then the reflected light from reflective surface 500' travels upward and outward from axis L along a second axis $A_2$ toward optical detector 144'. Reflective surface 500' may produce a specular reflection with the reflected light traveling along a single axis $A_2$, as shown in FIG. 19, or a diffuse reflection with the reflected light traveling in many different directions. Reflective surface 500' may be a shiny, mirrored, or otherwise reflective surface. Reflective surface 500' may be shaped and oriented to direct the reflected light toward optical detector 144'. For example, in FIG. 19, the reflective surface 500' is flat and is angled about 10 degrees relative to a horizontal plane to direct the reflected light toward optical detector 144'. The angled reflective surface 500' of FIG. 19 may also encourage drainage of any condensation (fuel or aqueous) that forms upon reflective surface 500'.

The illustrative optical monitor 104c' also includes at least one printed circuit board (PCB) 502' that mechanically and electrically supports light source 140' and optical detector 144'. PCB 502' may also allow light source 140' and/or optical detector 144' to communicate with controller 102 (FIG. 3). Light source 140' and optical detector 144' are illustratively coupled to the same PCB 502', but it is also within the scope of the present disclosure to use distinct PCBs.

The illustrative optical monitor 104c' further includes a cover 510', an upper housing 512', and a lower housing 514'. Lower housing 514' may be removably coupled to upper housing 512', such as using a snap connection 515', a threaded connection, or another removable connection.

Upper housing 512' contains light source 140', optical detector 144', and circuit board 502'. Upper housing 512' may be hermetically sealed to separate and protect its contents from the potentially corrosive environment in fuel delivery system 10 (FIG. 2). However, upper housing 512' may be at least partially or entirely transparent to permit the passage of light, as discussed further below.

Lower housing 514' contains target material 142' and reflective surface 500'. Reflective surface 500' may be formed directly upon lower housing 514' (e.g., a reflective coating) or may be formed on a separate component (e.g., a reflective panel) that is coupled to lower housing 514'. In the illustrated embodiment of FIG. 19, reflective surface 500' is located on bottom wall 516' of lower housing 514'. Unlike the contents of upper housing 512', which are separated from the vapors in fuel delivery system 10, the contents of lower housing 514', particularly target material 142', are exposed to the vapors in fuel delivery system 10. The illustrative lower housing 514' has bottom wall 516' with a plurality of bottom openings 517' and a side wall 518' with a plurality of side openings 519' to encourage the vapors in fuel delivery system 10 to enter lower housing 514' and interact with target material 142'. Openings 517', 519' may vary in shape, size, and location. In general, lower housing 514' should be designed to be sufficiently solid to support and protect its contents while being sufficiently open to expose its contents to the vapors in fuel delivery system 10. For example, the bottom openings 517' may be concentrated beneath target material 142'. Also, the side openings 519' adjacent to target material 142' may be relatively small, whereas the side openings 519' opposite from target material 142' may be relatively large.

In use, and as shown in FIG. 19, light source 140' directs a beam of light along the first axis $A_1$, through the transparent upper housing 512', and toward target material 142'. The L-shaped configuration of target material 142' may block any direct light pathways between light source 140' and reflective surface 500' to ensure that all of the light from light source 140' encounters target material 142' before reaching reflective surface 500'. The light that is able to pass through the pores 143' of target material 142' continues to reflective surface 500', which then reflects the light along the second axis $A_2$, back through the transparent upper housing 512', and to optical detector 144'. Optical detector 144' may signal a corrosive environment in fuel delivery system 10 when the transmitted light intensity through the corroding target material 142' reaches an undesirable level or changes at an undesirable rate, for example. After use, lower housing 514' may be detached (e.g., unsnapped) from upper housing 512' to facilitate removal and replacement of the corroded target material 142' and/or reflective surface 500' without disturbing the contents of upper housing 512'.

Optical monitor 104c' may be configured to detect one or more errors. If the light intensity detected by detector 144' is too high (e.g., at or near 100%), optical monitor 104c' may issue a "Target Material Error" to inform the operator that target material 142' may be missing or damaged. To avoid false alarms caused by exposure to ambient light, such as when opening turbine sump 32 (FIG. 2), optical monitor 104c' may only issue the "Target Material Error" when the high light intensity is detected for a predetermined period of time (e.g., 1 hour or more). On the other hand, if the light intensity detected by detector 144' is too low (e.g., at or near 0%), optical monitor 104c' may issue a "Light or Reflector Error" to inform the operator that light source 140' and/or reflective surface 500' may be missing or damaged. In this scenario, the entire lower housing 514', including reflective surface 500', may be missing or damaged.

Optical monitor 104c' may be combined with one or more other monitors of the present disclosure. For example, in the illustrated embodiment of FIG. 16, PCB 502' of optical monitor 104c' also supports a humidity sensor 520', which passes through upper housing 512' for exposure to the vapors in fuel delivery system 10 (FIG. 2). PCB 502' may also support a temperature sensor (not shown), which may be used to compensate for any temperature-related fluctuations in the performance of light source 140' and/or optical detector 144'.

In still yet another embodiment, monitor 104 collects spectroscopic data indicative of a corrosive environment in fuel delivery system 10. An exemplary spectrometer (not shown) operates by subjecting a liquid or vapor sample from fuel delivery system 10 to an energy source and measuring the radiative energy as a function of its wavelength and/or frequency. Suitable spectrometers include, for example, infrared (IR) electromagnetic spectrometers, ultraviolet (UV) electromagnetic spectrometers, gas chromatography-mass spectrometers (GC-MS), and nuclear magnetic resonance (NMR) spectrometers. Suitable spectrometers may detect absorption from a ground state to an excited state, and/or fluorescence from the excited state to the ground state. The spectroscopic data may be represented by a spectrum showing the radiative energy as a function of wavelength and/or frequency. It is within the scope of the present disclosure that the spectrum may be edited to hone in on certain impurities in the sample, such as acetate and acetic acid, which may cause corrosion in fuel delivery system 10, as well as sulfuric acid, which may cause odors in fuel delivery system 10. As the impurities develop in fuel delivery system 10, peaks corresponding to the impurities would form and/or grow on the spectrum. The spectrometer may share the collected data with controller 102 (FIG. 3) to signal a corrosive environment in fuel delivery system 10 when the impurity level reaches an undesirable level or changes at an undesirable rate, for example.

In still yet another embodiment, monitor 104 collects microbial data indicative of a corrosive environment in fuel delivery system 10. An exemplary microbial detector (not shown) operates by exposing a liquid or vapor sample from fuel delivery system 10 to a fluorogenic enzyme substrate, incubating the sample and allowing any bacteria in the sample to cleave the enzyme substrate, and measuring fluorescence produced by the cleaved enzyme substrate. The concentration of the fluorescent product may be directly related to the concentration of acetic acid producing bacteria (e.g., *Acetobacter, Gluconobacter, Gluconacetobacter*) in the sample. Suitable microbial detectors are commercially available from Mycometer, Inc. of Tampa, Fla. The microbial detector may share the collected data with controller 102 (FIG. 3) to signal a corrosive environment in fuel delivery system 10 when the fluorescent product concentration reaches an undesirable level or changes at an undesirable rate, for example.

To minimize the impact of other variables in monitor 104, a control sample may be provided in combination with the test sample. For example, monitor 104c of FIG. 6 may include a non-corrosive control material for comparison with the corrosive target material 142. This comparison would minimize the impact of other variables in monitor 104c, such as decreasing output from light source 140 over time.

As discussed above, control system 100 of FIG. 3 includes a remediation system 108 capable of taking at least one corrective action to remediate the corrosive environment in fuel delivery system 10. Controller 102 may activate remediation system 108 periodically (e.g., hourly, daily) in a preventative manner. Alternatively or additionally, controller 102 may activate remediation system 108 when the corrosive environment is detected by monitor 104. Various embodiments of remediation system 108 are described below with reference to FIG. 2.

In a first embodiment, remediation system 108 is configured to ventilate turbine sump 32 of fuel delivery system 10. In the illustrated embodiment of FIG. 2, remediation system 108 includes a first ventilation passageway 160 and a second ventilation or siphon passageway 170.

The first ventilation passageway 160 illustratively includes an inlet 162 in communication with the surrounding atmosphere and an outlet 164 in communication with the upper vapor space (i.e., top) of turbine sump 32. In FIG. 2, the first ventilation passageway 160 is positioned in lid 38 of turbine sump 32, but this position may vary. A control valve 166 (e.g., bulkhead-style vacuum breaker, check valve) may be provided along the first ventilation passageway 160. Control valve 166 may be biased closed and opened when a sufficient vacuum develops in turbine sump 32, which allows air from the surrounding atmosphere to enter turbine sump 32 through the first ventilation passageway 160.

The second ventilation or siphon passageway 170 is illustratively coupled to a siphon port 26 of pump 20 and includes an inlet 172 positioned in the lower vapor space (i.e., middle) of turbine sump 32 and an outlet 174 positioned in storage tank 16. A control valve 176 (e.g., automated valve, flow orifice, check valve, or combination thereof) may be provided in communication with controller 102 (FIG. 3) to selectively open and close the second ventilation passageway 170. Other features of the second ventilation passageway 170 not shown in FIG. 2 may include a restrictor, a filter, and/or one or more pressure sensors.

When pump 20 is active (i.e., turned on) to dispense fuel product 14, pump 20 generates a vacuum at siphon port 26. The vacuum from pump 20 draws vapor (e.g., fuel/air mixture) from turbine sump 32, directs the vapor to the manifold of pump 20 where it mixes with the circulating liquid fuel flow, and then discharges the vapor into storage tank 16 through the second ventilation passageway 170. As the vacuum in turbine sump 32 increases, control valve 166 may also open to draw fresh air from the surrounding atmosphere and into turbine sump 32 through the first ventilation passageway 160. When pump 20 is inactive (i.e., turned off), controller 102 (FIG. 3) may close control valve 176 to prevent back-flow through the second ventilation passageway 170. Additional information regarding the second ventilation passageway 170 is disclosed in U.S. Pat. No. 7,051,579, the disclosure of which is expressly incorporated herein by reference in its entirety.

The vapor pressure in turbine sump 32 and/or storage tank 16 may be monitored using the one or more pressure sensors (not shown) and controlled. To prevent over-pressurization of storage tank 16, for example, the vapor flow into storage tank 16 through the second ventilation passageway 170 may be controlled. More specifically, the amount and flow rate of vapor pulled into storage tank 16 through the second ventilation passageway 170 may be limited to be less than the amount and flow rate of fuel product 14 dispensed from storage tank 16. In one embodiment, control valve 176 may be used to control the vapor flow through the second ventilation passageway 170 by opening the second ventilation passageway 170 for limited durations and closing the second ventilation passageway 170 when the pressure sensor detects an elevated pressure in storage tank 16. In another embodiment, the restrictor (not shown) may be used to limit the vapor flow rate through the second ventilation passageway 170 to a level that will avoid an elevated pressure in storage tank 16.

Other embodiments of the first ventilation passageway 160 are also contemplated. In a first example, the first ventilation passageway 160 may be located in the interstitial space between a primary pipe and a secondary pipe (e.g., XP Flexible Piping available from Franklin Fueling Systems Inc. of Madison, Wis.) using a suitable valve (e.g., APT™ brand test boot valve stems available from Franklin Fueling Systems Inc. of Madison, Wis.). In a second example, the first ventilation passageway 160 may be a dedicated fresh air line into turbine sump 32. In a third example, the first ventilation passageway 160 may be incorporated into a pressure/vacuum (PV) valve system. Traditional PV valve systems communicate with storage tank 16 and the surrounding atmosphere to help maintain proper pressure differentials therebetween. One such PV valve system is disclosed in U.S. Pat. No. 8,141,577, the disclosure of which is expressly incorporated herein by reference in its entirety. In one embodiment, the PV valve system may be modified to pull fresh air through turbine sump 32 on its way into storage tank 16 when the atmospheric pressure exceeds the ullage pressure by a predetermined pressure differential (i.e., when a sufficient vacuum exists in storage tank 16). In another embodiment, the PV valve system may be modified to include a pair of tubes (e.g., coaxial tubes) in communication with the surrounding atmosphere, wherein one of the tubes communicates with storage tank 16 to serve as a traditional PV vent when the ullage pressure exceeds the atmospheric pressure by a predetermined pressure differential, and another of the tubes communicates with turbine sump 32 to introduce fresh air into turbine sump 32.

Other embodiments of the second ventilation passageway 170 are also contemplated. In a first example, instead of venting the fuel/air mixture from turbine sump 32 into storage tank 16 as shown in FIG. 2, the mixture may be directed through a filter and then released into the atmosphere. In a second example, instead of using siphon port 26 as the vacuum source for the second ventilation passageway 170 as shown in FIG. 2, the vacuum source may be an existing vacuum pump in fuel delivery system 10 (e.g., 9000 Mini-Jet available from Franklin Fueling Systems Inc. of Madison, Wis.), a supplemental and stand-alone vacuum pump, or a vacuum created by displaced fuel in storage tank 16 and/or fuel delivery line 18. In one embodiment, and as discussed above, the second ventilation passageway 170 may be incorporated into the PV valve system to pull fresh air through turbine sump 32 and then into storage tank 16 when fuel is displaced from storage tank 16. In another embodiment, the second ventilation passageway 170 may communicate with an in-line siphon port on fuel delivery line 18 to pull air from turbine sump 32 when fuel is displaced along fuel delivery line 18.

In a second embodiment, remediation system 108 is configured to irradiate bacteria in turbine sump 32 of fuel delivery system 10. In the illustrated embodiment of FIG. 2, a first radiation source 180 is positioned on an outer wall of turbine sump 32, and a second radiation source 180' is positioned in the ullage of storage tank 16. Exemplary radiation sources 180, 180' include ultraviolet-C (UV-C) light sources. When activated by controller 102 (FIG. 3), radiation sources 180, 180' may irradiate and destroy any bacteria in turbine sump 32 and/or storage tank 16, especially acetic acid producing bacteria (e.g., *Acetobacter, Gluconobacter, Gluconacetobacter*).

Figure 11:
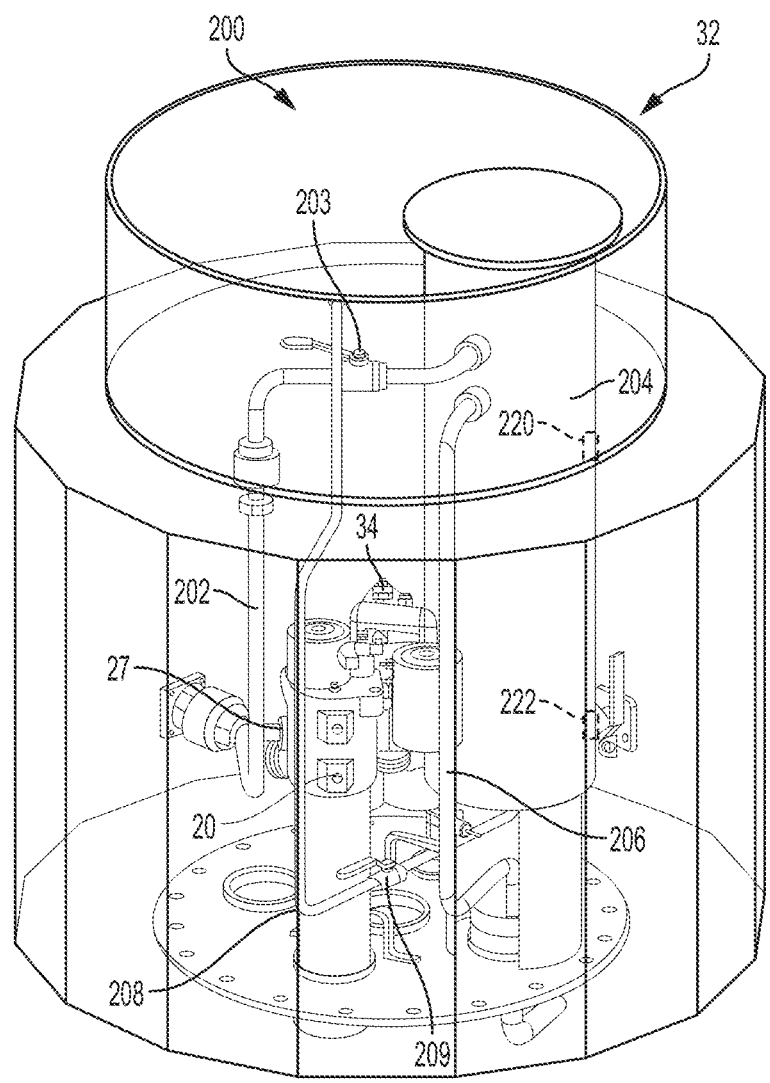
FIG. 11 is a perspective view of the turbine sump having a water filtration system.

In a third embodiment, remediation system 108 is configured to filter water from fuel product 14. An exemplary water filtration system 200 is shown in FIG. 11 and is located together with pump 20 in turbine sump 32 above storage tank 16 (FIG. 1). The illustrative water filtration system 200 includes a fuel inlet passageway 202 coupled to port 27 of pump 20, a water filter 204, a fuel return passageway 206 from the upper end of water filter 204, and a water removal passageway 208 from the lower end of water filter 204. The port 27 of pump 20 may be located upstream of leak detector 34 and its associated check valve (not shown) such that the water filtration system 200 avoids interfering with leak detector 34.

Water filter 204 is configured to separate water, including emulsified water and free water, from fuel product 14. Water filter 204 may also be configured to separate other impurities from fuel product 14. Water filter 204 may operate by coalescing the water into relatively heavy droplets that separate from the relatively light fuel product 14 and settle at the lower end of water filter 204. Incoming fuel pressure drives fuel radially outwardly through the sidewall of filter element 207 (FIG. 15), which is made from a porous filter substrate adapted to allow fuel to pass therethrough while preventing water passage therethrough. Any water that is separated from the fuel is driven downwardly through the bottom of filter element 207, which is made from a porous filter substrate that allows the passage of water therethrough. The separated water then falls by gravity to the bottom of the filter housing. Exemplary water filters 204 including filter element 207 are available from DieselPure Inc. Such water filters 204 may reduce the water content of fuel product 14 to 200 ppm or less, according to the SAE J1488 ver. 2010 test method.

Figure 14:
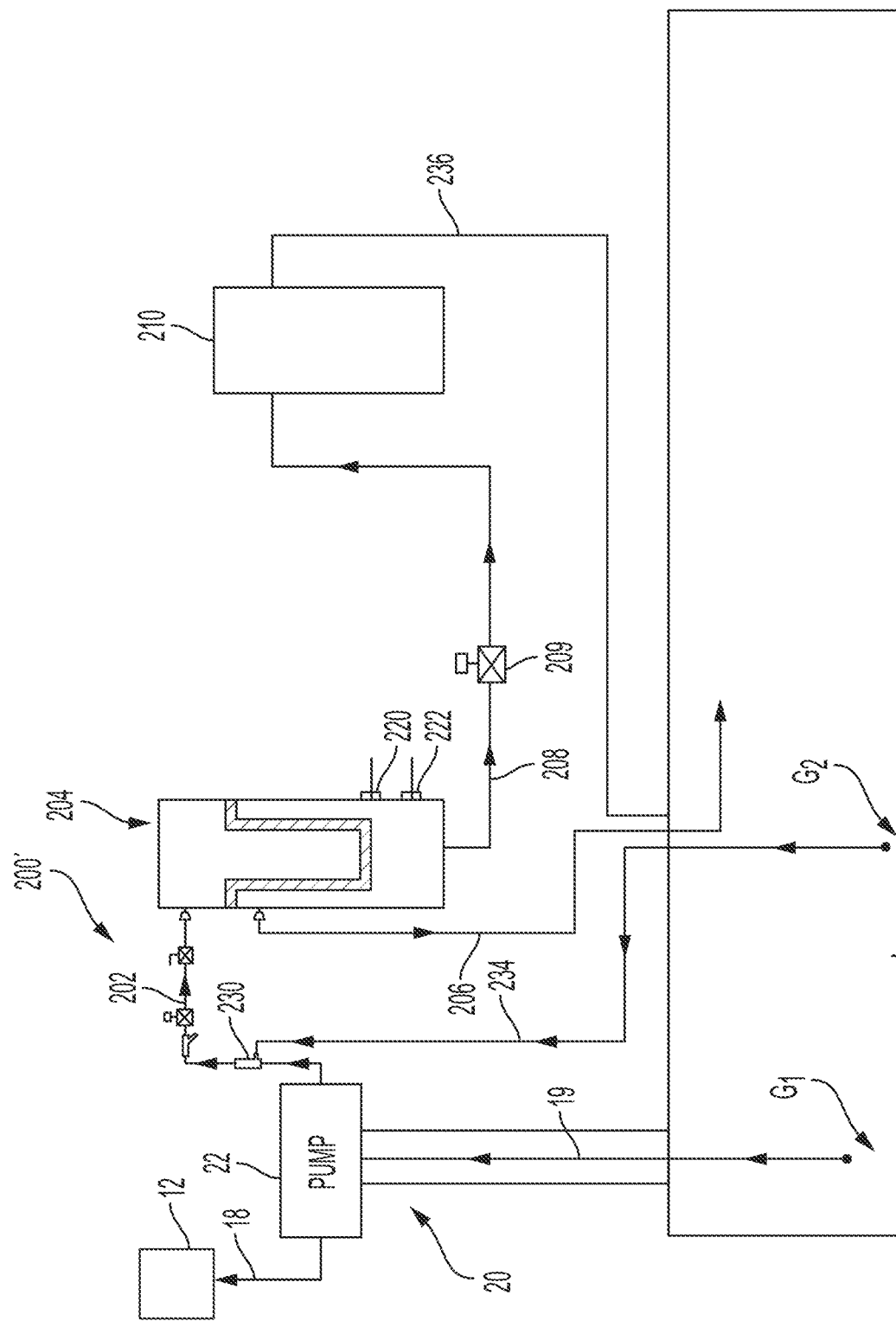
FIG. 14 is a schematic view of another exemplary water filtration system utilizing continuous filtration by eduction.
Figure 15:
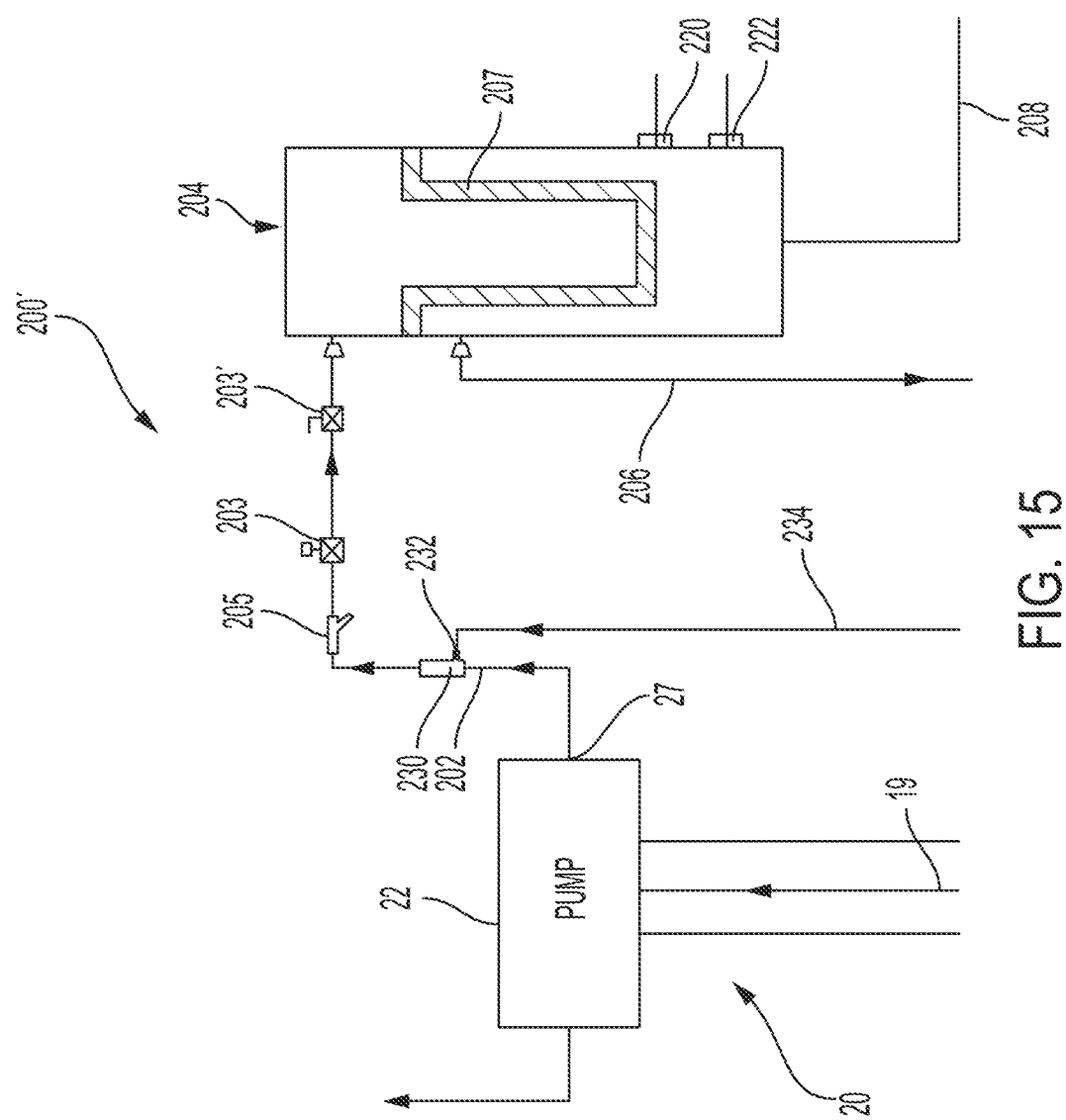
FIG. 15 is an enlarged portion of the schematic view of FIG. 14, illustrating the components of the water filtration system.
Figure 16:
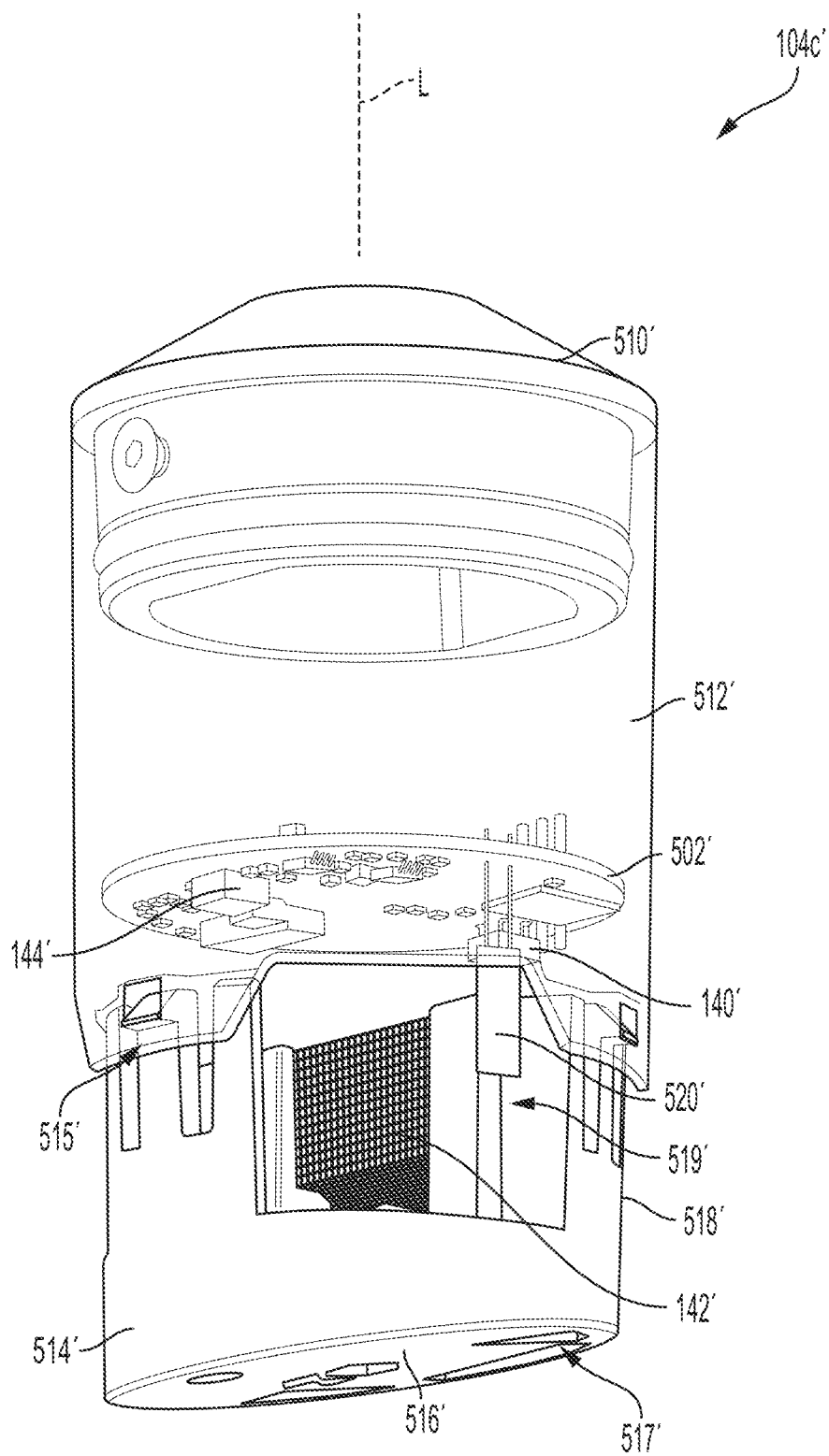
FIG. 16 is a perspective view of another exemplary optical monitor including an upper housing with a light source and an optical detector and a lower housing with a corrosive target material and a reflective surface.
Figure 18:
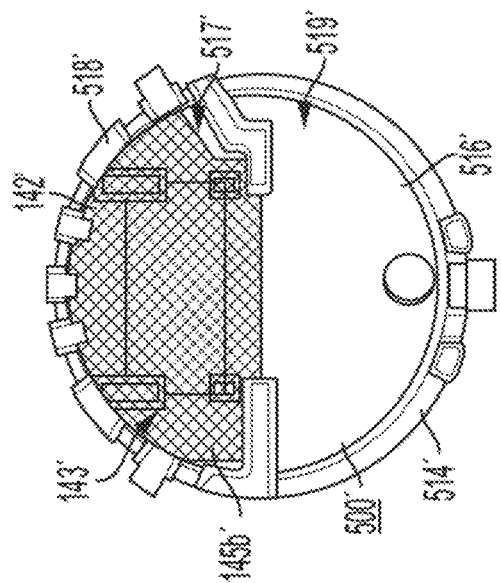
FIG. 18 is a top plan view of the lower housing and the corrosive target material of FIG. 16.
Figure 17:
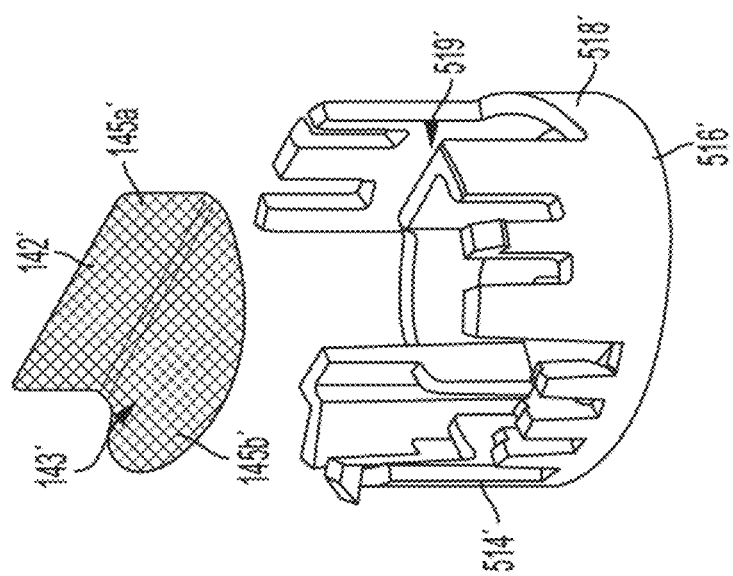
FIG. 17 is an exploded perspective view of the lower housing and the corrosive target material of FIG. 16.

The illustrative water filtration system 200 also includes one or more inlet valves 203 to selectively open and close the fuel inlet passageway 202 and one or more drain valves 209 to selectively open and close the water removal passageway 208. In certain embodiments, valves 203, 209 are solenoid valves that are controlled through controller 102. In other embodiments, valves 203, 209 are manual valves that are manually controlled by a user. In the embodiment of FIGS. 14-15, inlet solenoid valve 203 is provided downstream of strainer 205, which includes a mesh screen to protect valve 203 from exposure to solid sediment. A further manual ball valve 203' is provided downstream of solenoid valve 203 for manual on/off control of the illustrated filtration system 200', the details of which are further discussed below.

In operation, water filtration system 200 circulates fuel product 14 through water filter 204. Water filtration system 200 may operate at a rate of approximately 15 to 20 gallons per minute (GPM), for example. When pump 20 operates with inlet valve 203 open, pump 20 directs some or all of fuel product 14 from storage tank 16, through port 27 of pump 20, through the open fuel inlet passageway 202, and through water filter 204. If a customer is operating dispenser 12 (FIG. 1) during operation of water filtration system 200, pump 20 may direct a portion of the fuel product 14 to dispenser 12 via the delivery line 18 (FIG. 1) and another portion of the fuel product 14 to water filter 204 via the fuel inlet passageway 202. It is also within the scope of the present disclosure that the operation of water filtration system 200 may be interrupted during operation of dispenser 12 by temporarily closing inlet valve(s) 203 and/or 203' to water filter 204. As shown schematically in FIG. 14, water filter 204 may produce a clean or filtered fuel product 14 near the upper end of water filter 204 and a separated water product, which may be a water/oil mixture, near the lower end of water filter 204. Alternatively, water filter 204A shown in FIGS. 21 and 22 may utilize water/oil separation to product a clean or filtered fuel product 14, as described further below. For purposes of the present disclosure, "water filter 204" can interchangeably refer to water filter 204 shown in FIGS. 14 and 15 and described in detail herein, or to water filter 204A shown in FIGS. 21 and 22 and described in detail herein. As used herein, "oil" may refer to oil and oil-based products including motor fuel, such as gasoline and diesel.

The clean or filtered fuel product 14 that is discharged by water filter 204, such as rising to the upper end of water filter 204, may be returned continuously to storage tank 16 via the fuel return passageway 206. The filtered fuel product 14 may be returned to storage tank 16 in a dispersed and/or forceful manner that promotes circulation in storage tank 16, which prevents debris from settling in storage tank 16 and promotes filtration of such debris. By returning the filtered fuel product 14 to storage tank 16, water filtration system 200 may reduce the presence of water and avoid formation of a corrosive environment in fuel delivery system 10 (FIG. 1), including storage tank 16 and/or sump 32 of fuel delivery system 10. Water filtration system 200 may be distinguished from an in-line system that delivers a filtered fuel product to dispenser 12 (FIG. 1) solely to protect a consumer's vehicle.

Figure 12:
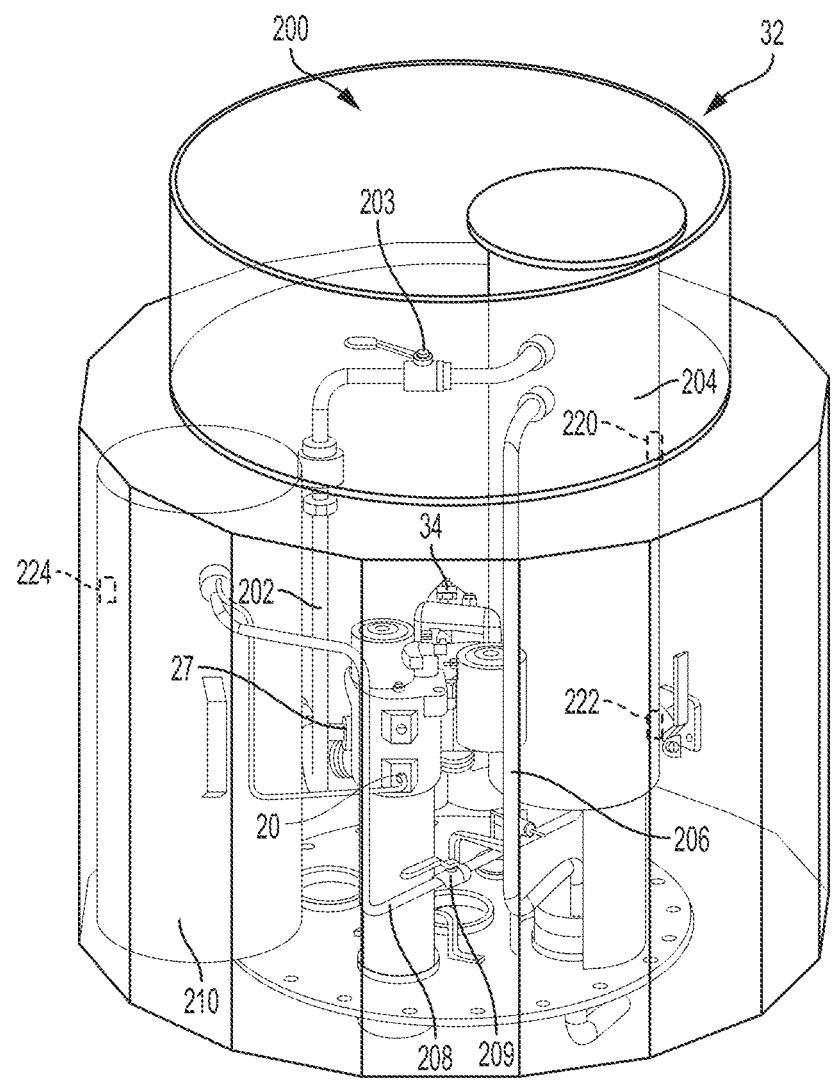
FIG. 12 is a perspective view of the turbine sump having a water filtration system similar to FIG. 11 and also including a water storage tank.
Figure 22:
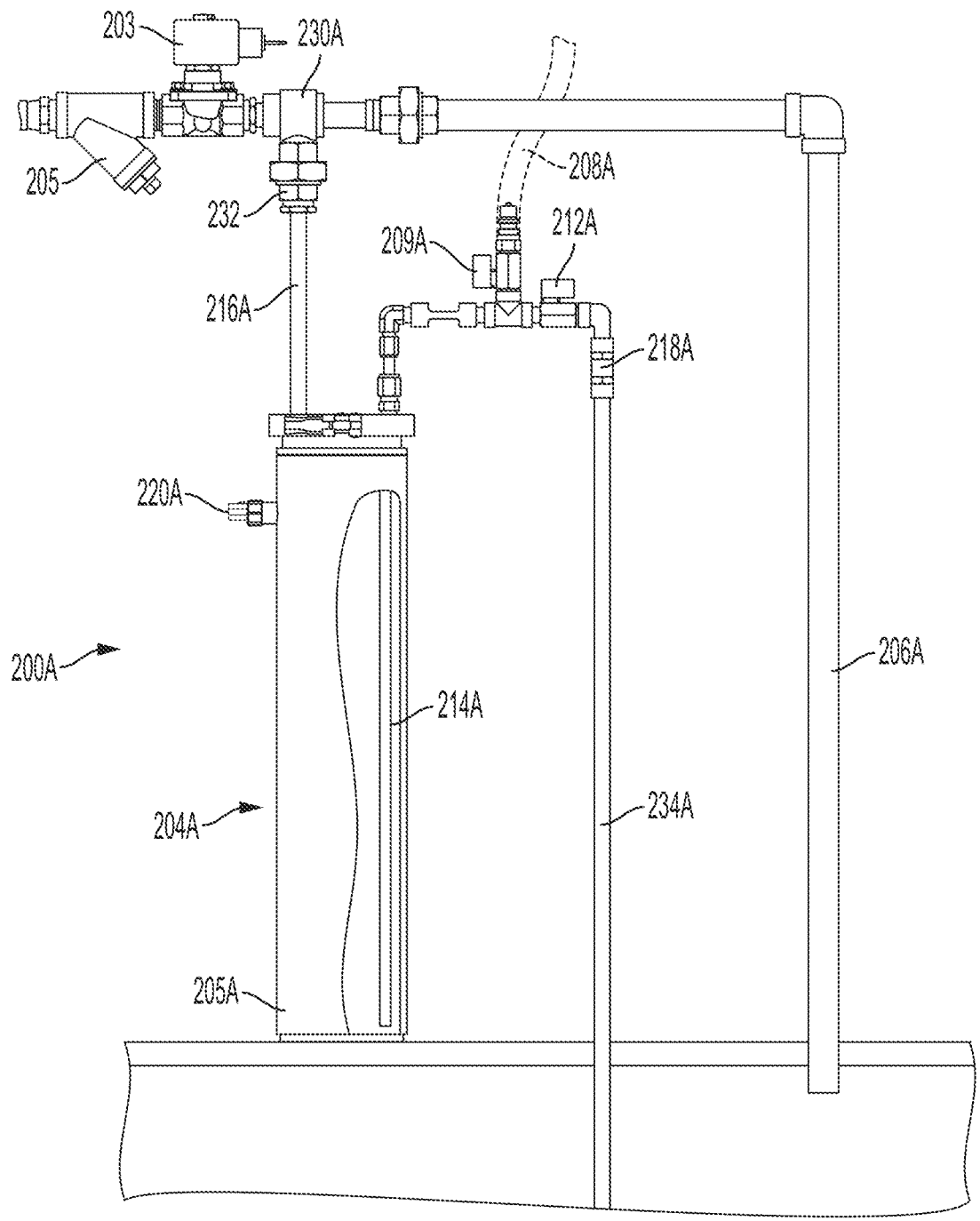
FIG. 22 is an enlarged portion of the schematic view of FIG. 21, illustrating the components of the water filtration system.

The separated water product that is discharged by water filter 204, such as by settling at the lower end of water filter 204, may be drained via the water removal passageway 208 when drain valve 209 is open. The separated water product may be directed out of turbine sump 32 and above grade for continuous removal, as shown in FIG. 11. Alternatively, the separated water product may be directed via passageway 208 to a storage tank 210 inside turbine sump 32 for batch removal when necessary, as shown in FIGS. 12, 14 and 22. If the separated water product is a water/oil mixture, the separated water product may be subjected to further processing to remove any oil from the remaining water. For example, a selective absorbent, such as the Smart Sponge® available from AbTech Industries Inc., may be used to absorb and remove any oil from the remaining water.

Referring to FIG. 14, storage tank 210 further includes a vent line 236 operable to vent the headspace above the separated water product as the level within tank 210 increases. In an exemplary embodiment, vent line 236 may be routed to the headspace above fuel product 14 within underground storage tank 16, such that any treatment or capture of the vapor within tank 210 may be routed through existing infrastructure used for treatment/capture of fuel vapor within tank 16. Alternatively, tank 210 may be vented to a dedicated space as required or desired for a particular application.

The illustrative water filtration systems 200, 200' of FIGS. 11, 12, 14 and 15 include a high-level water sensor 220 and a low-level water sensor 222 operably connected to water filter 204. The water sensors 220 and 222 may be capacitance sensors capable of distinguishing fuel product 14 from water. The high-level water sensor 220 may be located beneath the entry into fuel return passageway 206 to prevent water from entering fuel return passageway 206. The illustrative water filtration system 200 of FIG. 12 further includes a high-level water sensor 224 in storage tank 210. The high-level water sensor 224 may be an optical sensor capable of distinguishing the separated water product from air. Sensors 220, 222, and 224 may be low-power devices suitable for operation in turbine sump 32. In one exemplary embodiment, filter 204 may have a water capacity of about 2.75 liters (0.726 gallons) between the levels of sensors 220, 222.

Turning to FIG. 14, water filtration system 200' is shown. Water filtration system 200' is similar to filtration system 200 described above and includes several components and features in common with system 200 as indicated by the use of common reference numbers between systems 200, 200'. However, water filtration system 200' further includes eductor 230 in fuel inlet passageway 202 which operates to effect continuous fuel filtration during operation of pump 20, while also allowing for normal operation of fuel dispenser 12 served by pump 20 as further described below.

As fuel is withdrawn from tank 16 by operation of pump 20, a portion of the fuel which would otherwise be delivered to dispenser 12 via delivery line 18 is instead diverted to fuel inlet passageway 202. In an exemplary embodiment, this diverted flow may be less than 15 gallons/minute, such as between 10 and 12 gallons/minute. This diverted flow of pressurized fuel passes through eductor 230, as shown in FIGS. 14 and 15, which is a venturi device having a constriction in the cross-sectional area of the eductor flow path. As the flow of fuel passes through this construction, a negative pressure (i.e., a vacuum) is formed at vacuum port 232 (FIG. 15), which may be separate flow tube terminating in an aperture formed in the sidewall of eductor 230 downstream of the constriction.

Filtration uptake line 234 is connected to vacuum port 232 and extends downwardly into tank 16, such that filtration uptake line 234 draws fuel from the bottom of tank 16. In an exemplary embodiment, gap $G_2$ between the inlet of line 234 and the bottom surface of tank 16 is zero or near-zero, such that all or substantially all water or sediment which may be settled at the bottom of tank 16 is accessible to filtration uptake line 234. For example, line 234 may be a rigid or semi-rigid tube with an inlet having an angled surface formed, e.g., by a cut surface forming a 45-degree angle with the longitudinal axis of the tube. This angled surface forms a point at the inlet of line 234 which can be lowered into abutting contact with the lower surface of tank 16, while the open passageway exposed by the angled surface allows the free flow of fuel into line 234. Other inlet configuration may also be used for line 234, including traditional inlet openings close to, but not abutting, the lower surface of the tank.

By contrast to the zero or near-zero gap $G_2$ for filtration uptake line 234, a larger gap $G_1$ is formed between the intake of fuel uptake line 19 and the bottom surface of tank 16. For example, the intake opening to submersible pump 24 (FIG. 1) may be about 4-6 inches above the lower surface of tank 16. Where the pump is located above fuel product 14, the intake opening into fuel uptake line may instead be about 4-6 inches above the lower surface of tank 16. This elevation differential reflected by gaps $G_1$ and $G_2$ ensures that any water or contaminated fuel settled at the bottom of tank 16 will be taken up by filtration uptake line 234 rather than fuel uptake line 19. At the same time, the relatively high elevation of the intake opening serving delivery line 18 ensures that any accumulation of contaminated fuel will be safely within gap $G_1$, such that only clean fuel will be delivered to dispenser 12. In this way, filtration system 200' simultaneously remediates contamination and protects against uptake of any contaminated fuel that may exist in tank 16, thereby providing "double protection" against delivery of contaminated fuel to dispenser 12.

The illustrative filtration system 200' also achieves this dual mitigation/prevention functionality with low-maintenance operation, by using eductor 230 to convert the operation of pump 20 into the motive force for the operation of system 200'. In particular, a single only pump 20 used in conjunction with system 200' both provides clean fuel to dispenser(s) 12 via delivery line 18, while also ensuring that any accumulation of contaminated fuel at the bottom of tank 16 is remediated by uptake into filtration line 234 and subsequent delivery to filter 204. The lack of a requirement of extra pumping capacity lowers both initial cost and running costs. Moreover, the additional components of system 200', such as eductor 230, filter 204, valves 203, 209 and water tank 210, all require little to no regular maintenance.

Filtration system 200' also achieves its dual mitigation/prevention function in an economically efficient manner by using an existing pump to power the filtration process, while avoiding the need for large-capacity filters. As described in detail above, filtration system 200' is configured to operate in conjunction with the normal use of fuel delivery system 10 (FIG. 1), such that the filtration occurs whenever dispensers 12 are used to fuel vehicles. This ensures that filtration system 200' will operate with a frequency commensurate with the frequency of use of fuel delivery system 10. This high frequency of operation allows filter 204 to be specified with a relatively small filtration capacity for a given system size, while ensuring that filtration system 200' retains sufficient overall capacity to mitigate even substantial contamination. For example, a throughput of 10-12 gallons/minute through filter 204 may be sufficient to treat all the fuel contained in a tank 16 sized to serve 6-8 fuel dispensers 12 (FIG. 1) with each dispenser 12 capable of delivering 15-20 gallons of clean fuel per minute. In this system sizing example, eductor 230 may be sized to deliver 0.1-0.3 gallons per minute of fluid via filtration uptake line 234 with a maximum vertical lift of 15 feet, using a flow through fuel inlet passageway 202 of 10-12 gallons per minute at an inlet pressure of about 30 PSIG (resulting in a pressure of at least 5 PSIG at the outlet of eductor 230).

Figure 21:
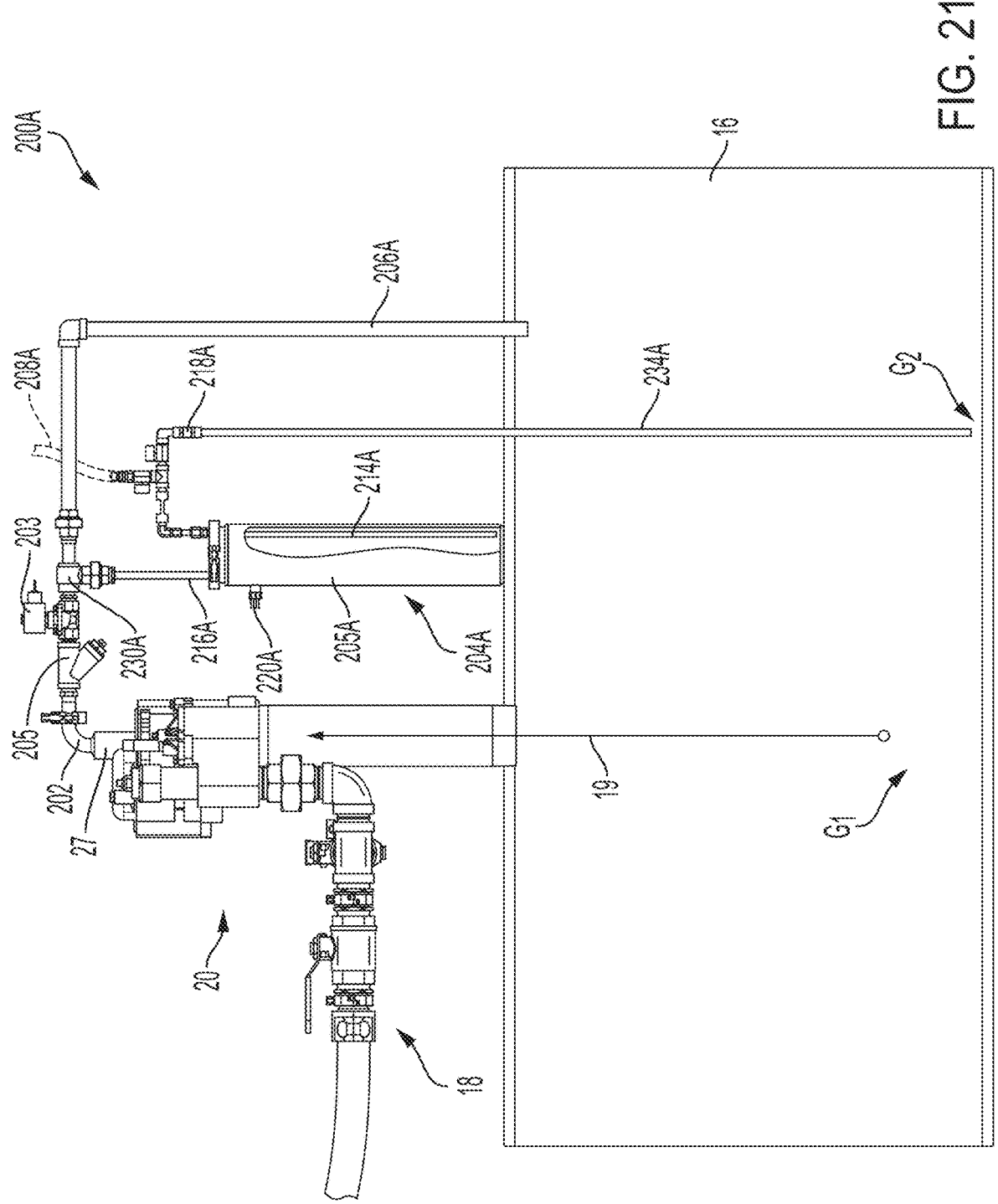
FIG. 21 is a schematic view of another exemplary water filtration system utilizing continuous filtration by eduction.

An alternative water filtration system 200A is shown in FIGS. 21 and 22. Water filtration system 200A is similar to filtration system 200' described above and includes several components and features in common with systems 200 and 200', as indicated by the use of common reference numbers between systems 200, 200' and 200A. Moreover, common reference numbers are used for common components of systems 200' and 200A, and structures of filtration system 200A have reference numbers which correspond to similar or identical structures of filtration system 200', except with "A" appended thereto as further described below. Filtration systems 200' and 200A may be used interchangeably in connection with fuel delivery system 10 and its associated systems.

However, filtration system 200A includes filter 204A utilizing an oil/water separation tank 205A to accomplish the primary removal of water from fuel product 14, rather than a filter element 207 as described above with respect to filtration system 200'. In addition, the routing of fuel flows and the use of eductor 230A in generating the motive force for fuel filtration contrasts with system 200', as described in further detail below.

Similar to system 200', filtration system 200A uses a diverted flow of fuel from submersible turbine pump 20 as the primary driver of fluid flows through eductor 230, such that pump 20 provides the primary motive force for filtration. In the illustrated embodiment of FIG. 22, eductor 230A receives the motive fuel flow from the outlet of pump 20, e.g., along a discharge fluid passageway. However, it is contemplated that eductor 230 can receive a diverted flow on the suction side of pump 20, including from fuel uptake line 19, for example. The diverted fuel flow passes through port 27 of pump 20, as shown in FIG. 21, and through inlet passageway 202, strainer 205 and inlet valve 203 in a similar fashion to system 200'. However, unlike system 200', filtration system 200A positions eductor 230 downstream of both valve 203, and the outlet fuel flow from eductor 230A is delivered directly to fuel return passageway 206 and then to storage tank 16. This is in contrast to the flow of fluid discharged from eductor 230 described above, which directs both the motive fuel flow from inlet passageway 202, and the filtration flow from uptake line 234, to filter 204 (FIG. 15).

As best seen in FIG. 22, filter 204A is functionally interposed between eductor 230A and fuel filtration uptake line 234A. As the motive fuel flow passes through eductor 230A from inlet passageway 202 to return passageway 206A, the vacuum created by eductor 230A is transmitted to the interior of filter 204A via filter return passageway 216A which extends from the vacuum port of eductor 230A to an aperture in the upper portion (e.g., the top wall) of filter 204A. This connection creates a vacuum pressure within filter 204A, which draws a flow of fluid (e.g., fuel or a fuel/water mixture) from the bottom of tank 16 via filtration uptake line 234A. This filtration flow enters filter 204A at its top portion, but is delivered to the bottom portion of filter 204A via dip tube 214A (FIG. 22).

In operation, filter 204A will operate in a steady state in which tank 205A is always filled with fluid drawn from tank 16. New fluid received from uptake line 234A is deposited at the bottom of filter 204A via dip tube 214A, and an equal flow of fluid is discharged from the top of filter 204A via return passageway 216. In an exemplary embodiment, the flow rate through filter 204A is slow enough, relative to the internal volume of filter 204A, to allow for natural separation and stratification of water and fuel within the volume of filter 204A, such that any water contained in the incoming fuel remains at the bottom of filter 204A and only clean fuel is present at the top of filter 204A.

In an exemplary embodiment, the flow rate through filter 204A is controlled with a combination of vacuum pressure from eductor 230A and the cross-sectional size of the channel defined by dip tube 214A. These two variables may be controlled to produce a nominal flow rate (i.e., throughput) through filter 204A, as well as a fluid velocity through dip tube 214A. In particular, the vacuum level produced by eductor 230A is positively correlated with both flow rate and fluid velocity, while the cross-section of dip tube 214A is positively correlated with flow rate but negatively correlated with fluid velocity. To preserve the ability for natural fluid stratification and avoid turbulence at the bottom of filter 204A, flow rate should be kept low enough to allow incoming fuel to remain coagulated as a volume of fuel separate from any surrounding water, rather than separating out into smaller droplets that would need to re-coagulate before "floating" out of the water layer. For example, an exemplary fluid velocity which produces such favorable fluid mechanics for filter 204A may be as high as 1.0, 2.0, 3.0 or 4.0 ft/second, such as about 3.3 ft/second.

In one exemplary arrangement, oil/water separation tank 205A has a nominal volume of 1.1 gallons, dip tube 214A defines a fluid flow cannula with an internal diameter of 0.25 inches, and vacuum level generated by eductor 230A is maintained between 12-15 inHg. This configuration produces a flow rate of about 0.50 gallons per minute (gpm) and an incoming fluid velocity (at the exit of dip tube 214A into the lower portion of filter 204A) of about 3.27 ft/sec. In this arrangement, throughput of filter 204A is maximized while preventing unfavorable fluid flow characteristics as described above. Moreover, if vacuum is increased to 18 inHg, aeration of the incoming fuel can create unfavorable effects, such as foaming of diesel fuel.

Additional elements may be provided create operator control (or control via controller 102, shown in FIG. 3) over one or more constituent elements of the fluid velocity. For example, an adjustable or restricting flow orifice, such a ball valve or flow orifice plate, may be provided in the motive flow to eductor 230A. In an exemplary embodiment, this restriction may be placed downstream of eductor 230A in fuel return passageway 206A for example. This adjustable flow orifice may constrict the flow through passageway 206A, which establishes a back pressure on eductor 230A and thereby limits or defines the nominal vacuum pressure generated by eductor 230A. Another control element may be a similar adjustable or restricting flow orifice placed in filtration uptake line 234A, which limits the uptake flow rate to ensure the nominal flow volume and speed is achieved. In the above-described example of 0.50 gpm, a flow orifice diameter of 0.0938 inches in uptake line 234A has been found to produce the target flow rate of 0.50 gpm and the target flow speed of about 3.3 ft/sec when the vacuum pressure on eductor 230A is set to a target range of 12-15 inHg.

The size of filter 204A may be scaled up or down to accommodate any desired filtration capacity, and the particular configuration of filtration system 200A can be modified in keeping with the principles articulated above. For example, increasing the cross-section of dip tube 214A decreases fluid velocity, such that the nominal flow rate through filtration uptake line 234A may be increased without producing an unfavorable fluid velocity. Similarly, the nominal volume of tank 205A may be decreased if no turbulence is experienced in the stratification of the contained fluids, or may be increased in order to accommodate a modest level of turbulence.

If water is present in the fluid drawn from the bottom of storage tank 16 through uptake line 234A (FIG. 21), the water will naturally separate from the fuel and settle to the bottom of filter 204A, where the water is collected and retained for later withdrawal (described below). The clean fuel 14, which floats to the top of the stratified fluids within filter 204A, will be drawn back through eductor 230 via filter return passageway 216A and allowed to mix with the motive flow of fuel to be discharged to tank 16 via fuel return passageway 206A. In this way, filter return passageway 216A combines with fuel return passageway 206A to form the fuel return passageway which returns filtered fuel product from filter 204A to the storage tank.

If sufficient water accumulates within filter 204A, the water reaches high-level water sensor 220A (FIG. 22) exposed to the interior of tank 205A and positioned above the lower portion of filter 204A. In the illustrated embodiment, high-level water sensor 22A is located on the upper portion of the filter 204A, at a height that results in a majority of the fluid in the filter 204A being below sensor 220A. In some embodiments, 60%, 70%, 80% or 90% of the internal volume of filter 204A may be below sensor 220A. This arrangement allows a significant amount of water to accumulate to avoid frequent draining procedures, while also using the remaining filter volume as a secure buffer of clean fuel above the water level to prevent accidental discharge of water or contaminated fuel from filter 204A to storage tank 16.

When contacted with water, sensor 220A activates and sends a signal to controller 102 (FIG. 3), which may then activate an alarm or initial a remediation protocol, or take other corrective action as described herein. For example, activation of water sensor 220A may issue a notification to prompt an operator to drain the water accumulated in tank 205A, or may initiate a similarly automated water removal process.

FIG. 22 illustrates water removal passageway 208A, which is functionally interposed between filtration uptake line 234A and dip tube 214A. To initiate a water removal procedure either by a human operator or by operation of controller 102 (FIG. 3), uptake valve 212A may first be closed to prevent any further uptake of fuel 14 from tank 16. Water outlet valve 209A may then be opened, and a pump (not shown) attached to water removal passageway 208A may be activated to draw water from the bottom of filter 204A via dip tube 214A. Where the water withdrawal is done by a human operator, a hand pump or manually operable electric pump may be used. Alternatively, an automated electric pump may be used by the operator, or controlled by controller 102 (FIG. 3) to automatically drain the water as part of a corrective action protocol.

In an exemplary embodiment, check valve 218A may be provided in uptake line 234 between tank 16 and uptake valve 212A, in order to provide additional insurance against a backflow of water into tank 16 during water withdrawal. Check valve 218A also guards against any potential siphoning of water from filter 204A, which may be located physically above tank 16, into tank 16 via dip tube 214A and filtration uptake line 234A.

The water withdrawal process may be calibrated, either by a human operator or controller 102 (FIG. 3), to withdraw a predetermined quantity of fluid upon initiation of a water removal protocol. The predetermined amount may be the volume of fluid calculated to exist below water sensor 220A and within water filter 204A, for example. Optionally, inlet valve 203 may be closed during the water removal process, in order to prevent a competing suction pressure from eductor 230. Alternatively, turbine pump 20 (FIG. 21) may be shut down and inlet valve 203 may be left open.

Figure 23:
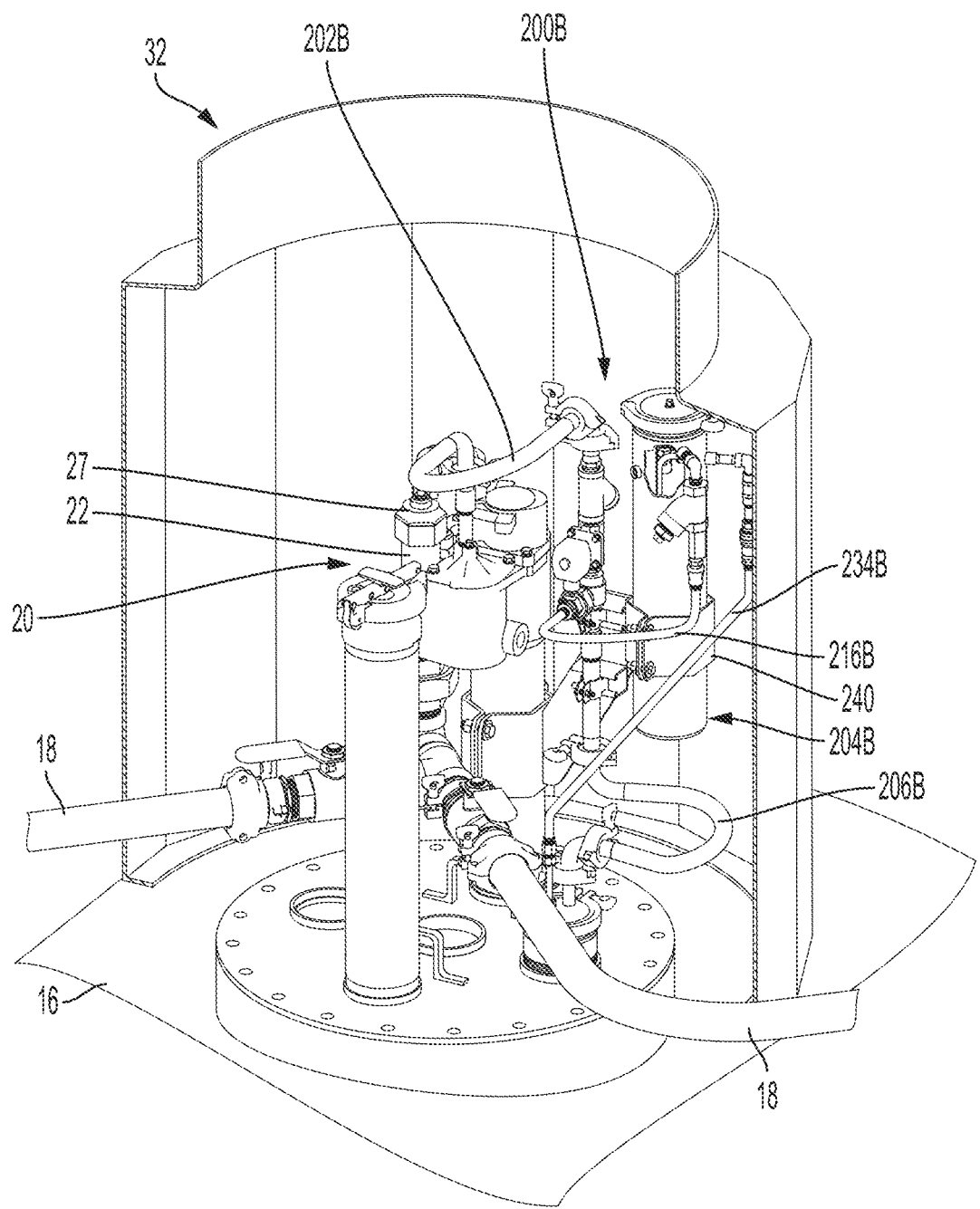
FIG. 23 is a perspective view of yet another exemplary water filtration system utilizing continuous filtration by eduction.

Turning now to FIG. 23, filtration system 200B includes another separator-type filter 204B and is otherwise similarly constructed to filtration system 200A described above. Common reference numbers are used for common components of systems 200', 200A and 200B, and structures of filtration system 200B have reference numbers which correspond to similar or identical structures of filtration systems 200' and 200A, except with "B" appended thereto as further described below. Filtration system 200B has all the same functions and features as filtration system 200A described above, except as noted below. Filtration systems 200', 200A and 200B may be used interchangeably in connection with fuel delivery system 10 and its associated systems.

However, filter 204B of filtration system 200B includes sensor valve assembly 244, shown in FIGS. 24B-27, which can be used in lieu of (or in addition to) high-level water sensor 220A (FIG. 22) to sense the presence of water near the top of tank 205B and, in conjunction with sensor 242 (FIG. 24B), issue a signal or alert indicative of this high-water condition.

As best seen in FIG. 23, the components of filtration system 200B are sized and configured to fit within sump 32, together with a typical set of existing components including turbine pump 22, delivery lines 18 and associated shutoff valves and ancillary structures. In the illustrative embodiment of FIGS. 24A and 24B, mounting bracket 240 is provided to provide structural support for tank 205B and associated structures from the flow lines between inlet passageway 202B and return passageway 206B.

Like filtration systems 200, 200' and 200A described above, filtration system 200B may also be applied to other sumps or parts of fuel delivery system 10, such as dispenser sump 30 (FIG. 1). Also similar to systems 200' and 200A, system 200B uses a diverted flow of fuel from submersible turbine pump 20 as the primary driver of fluid flows through eductor 230, via inlet passageway 202B and strainer 205 (FIG. 24A), such that pump 20 provides the primary motive force for filtration.

Figure 24A:
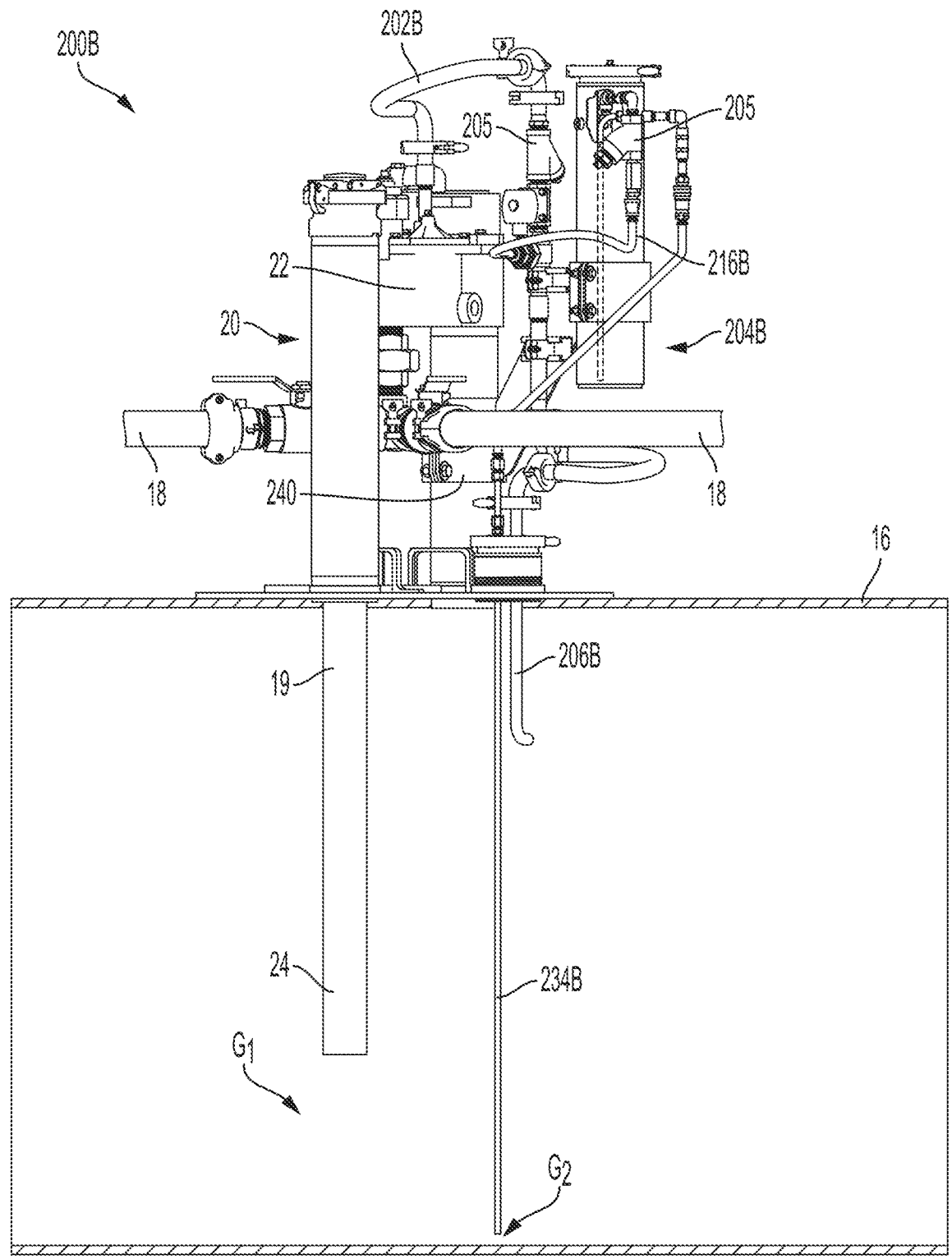
FIG. 24A is side elevation, section and partial cutaway view of the water filtration system of FIG. 23.

Fuel flows downstream to fuel return passageway 206B to return to the underground storage tank 16 (FIG. 24A), passing eductor 230 to create vacuum pressure in filter return passageway 216B, which in turn transmits the vacuum pressure to the interior of tank 205B via valve assembly 244 (as further described below). This vacuum pressure also within tank 205B is sufficient to draw fuel from UST 16 via filtration uptake line 234B, which extends to the bottom of UST 16 as seen in FIG. 24A and also described in detail herein with respect to other filtration system configurations. The fuel drawn through uptake line 234B provides a slow and steady flow into the bottom of tank 205B via dip tube 214B, also described in greater detail with respect to filtration system 200A. During steady-state operation, the vacuum in return passageway 216B draws fuel back to the primary return flow through fuel return passageway 206B. In the illustrated embodiment of FIGS. 24A and 24B, strainer 205 is provided between valve assembly 244 and eductor 230.

Figure 24B:
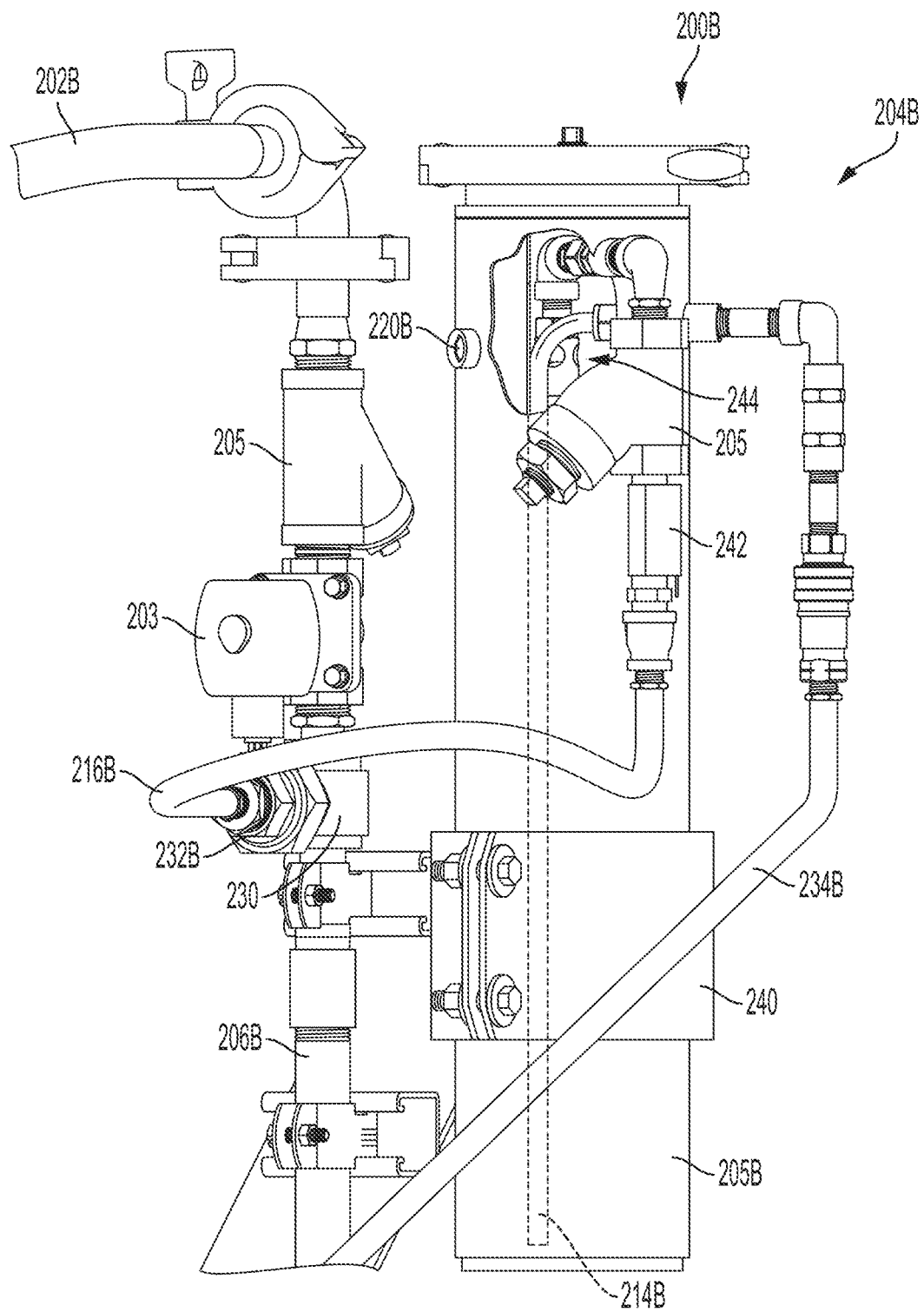
FIG. 24B is side elevation, enlarged view of a portion of the water filtration system of FIG. 24A.
Figure 25:
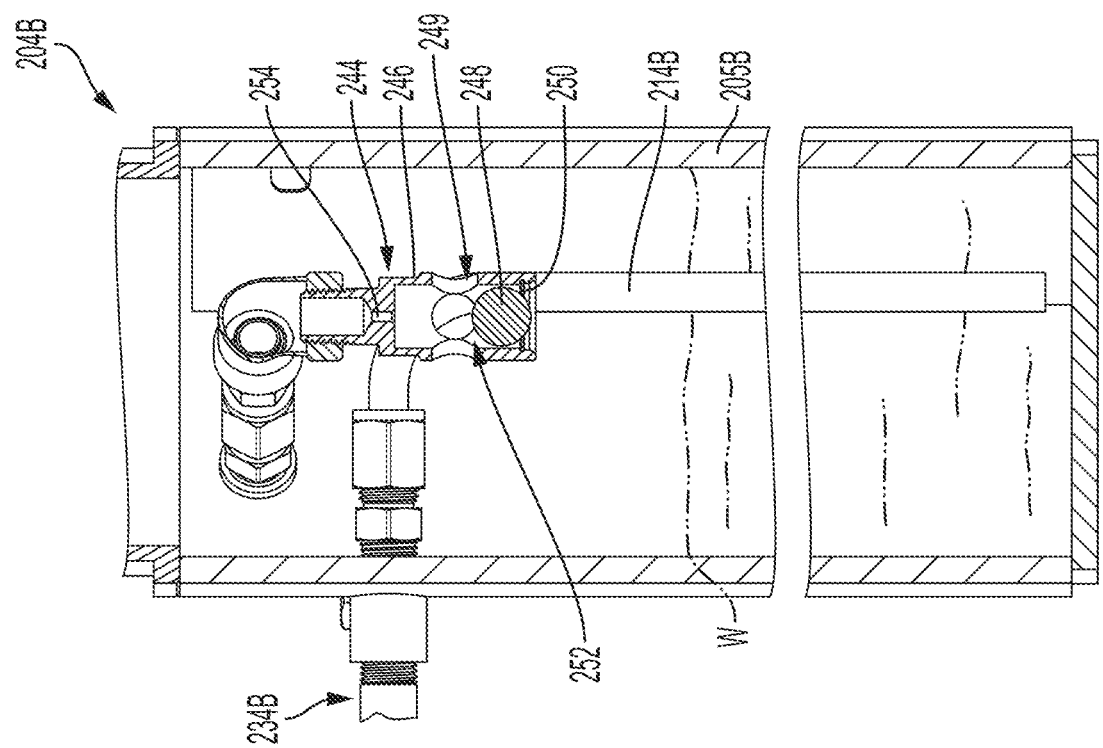
FIG. 25 is a side elevation, section view of a portion of the water filtration system of FIG. 23, illustrating the water filter at partial water capacity.
Figure 27:
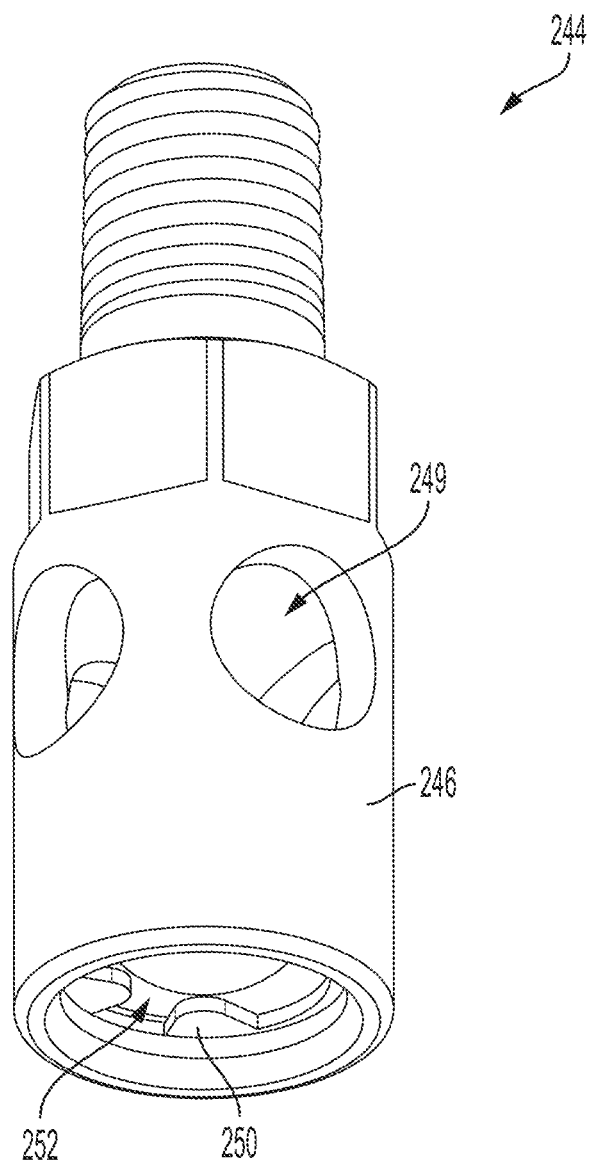
FIG. 27 is a perspective view of an automatic shutoff valve used in the water filter shown in FIGS. 23-26.
Figure 28:
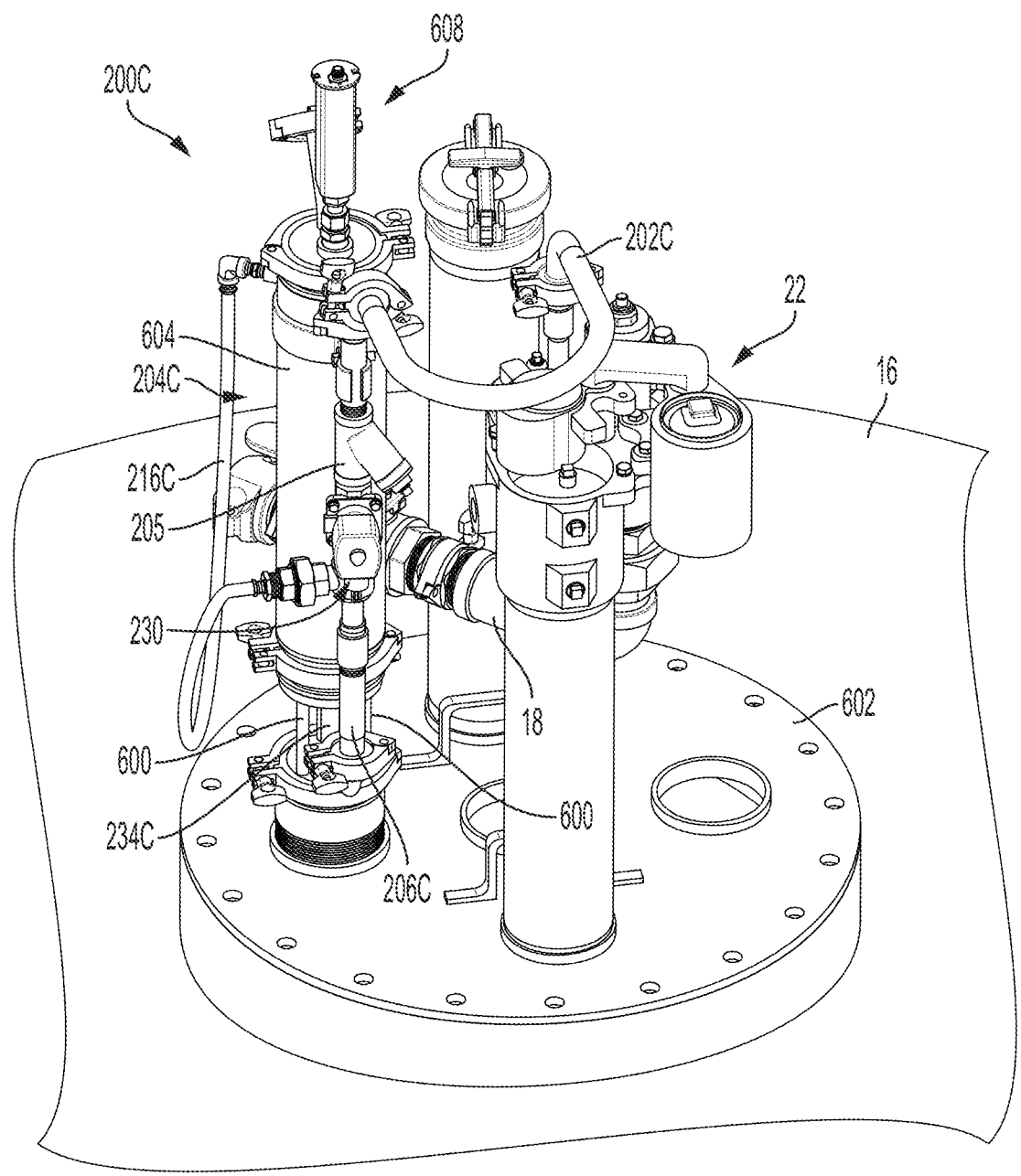
FIG. 28 is a perspective view of yet a further exemplary water filtration system.
Figure 29:
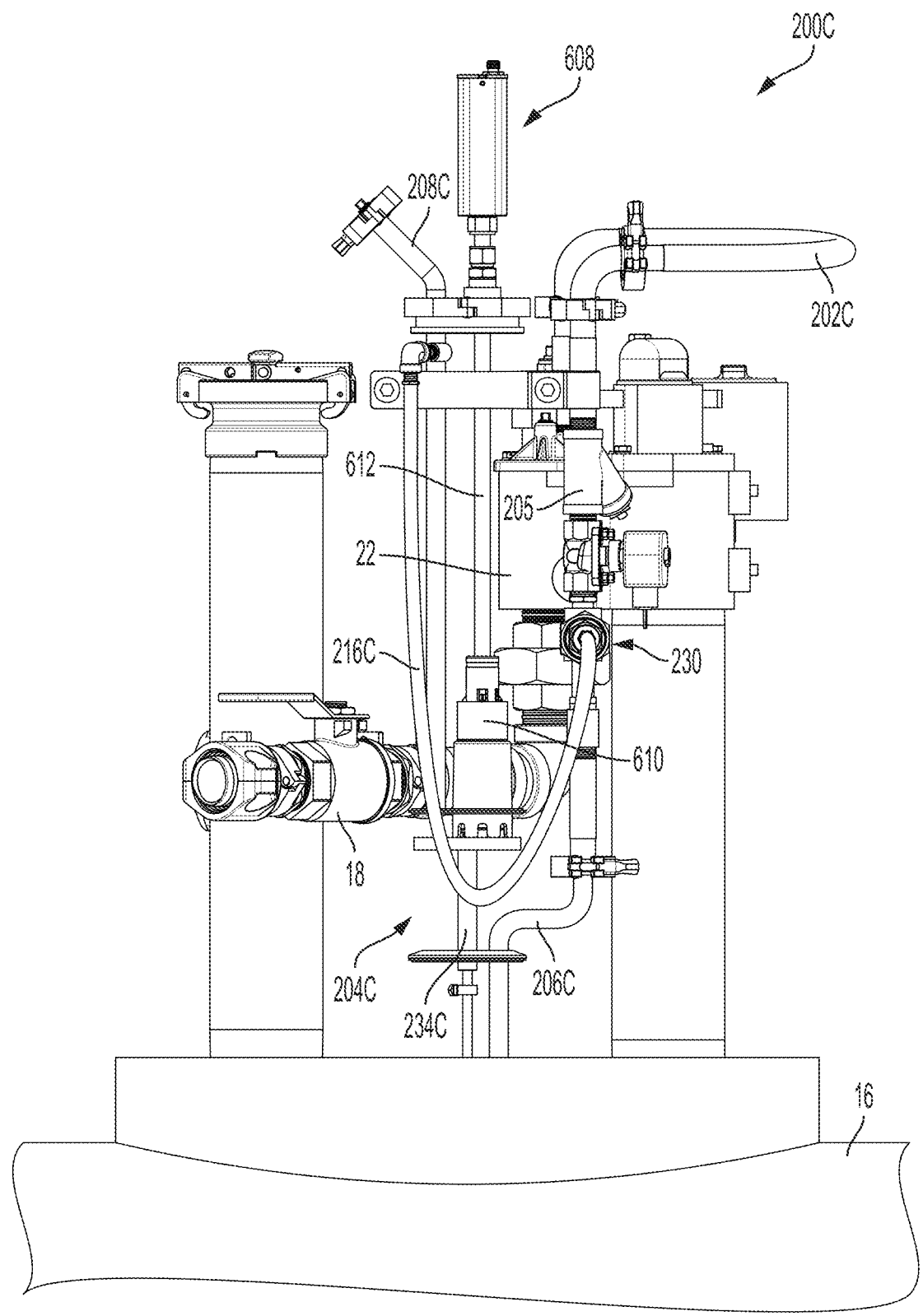
FIG. 29 is an elevational view of the water filtration system of FIG. 28 with the outer housing of the filter removed to reveal the internal components.

Turning now to FIG. 25, filter 204B is shown partially filled with water W and, during steady-state operation, the remainder of tank 205B is filled with fuel floating above water W. In this configuration, float 248 resides at the bottom of the interior cavity 252 of sensor valve body 246 of sensor assembly 244, retained by snap ring 250. Fuel deposited into tank 205B via dip tube 214B rises to float on the heavier water W, while any water contained in the deposited fuel stratifies to remain in water W. Because water W is well below float 248, pure fuel is continuously cycled through sensor valve assembly via ports 249 in valve body 246. This pure fuel is then drawn into vacuum port 254 to be returned to UST 16 via return passageway 216B (FIG. 24B).

During the steady-state, low-water operation depicted by FIG. 25, a vacuum is maintained throughout the components of water filtration system 200B as described herein. This vacuum maintains a steady flow of fuel through filter return passageway 216B via eductor 230, as shown in FIG. 24B. This flow is measured by flow sensor 242, which is in fluid communication with the suction port of eductor 230 and/or the interior flow path defined by passageway 216B. Sensor 242 detects the presence (and, optionally, the rate) of fluid flow through the suction port of eductor 230, and issues a signal (or a lack of a signal) indicative of such fluid flow. This signal may be received by controller 102, for example, or may simply be received by an operator via an indicator (light, siren, etc.).

Figure 26:
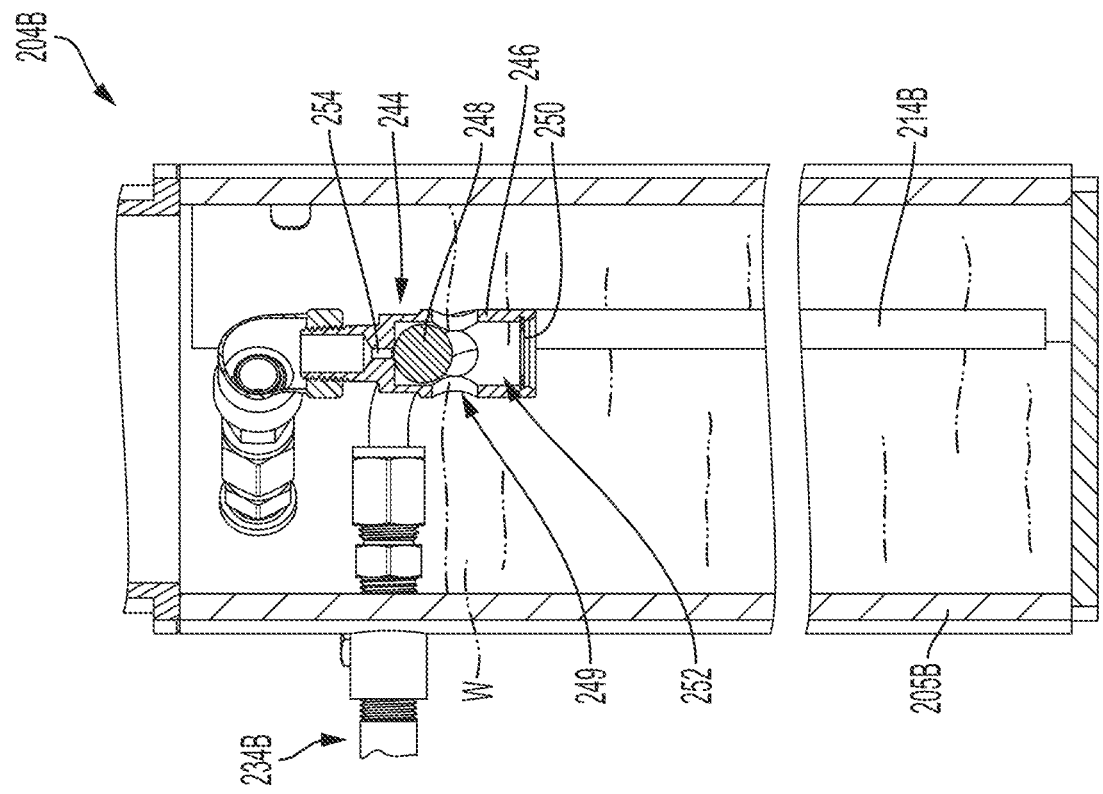
FIG. 26 is another side elevation, section view of a portion of the water filtration system of FIG. 23, illustrating the water filter at full water capacity.

In FIG. 26, the level of water W has risen such that a portion of sensor valve assembly 244 is submerged below the level of water W. Float 248 has a density below that of water W, but above that of the hydrocarbon fuel stratified above water W as described above. Details of an exemplary float 248 can be found in U.S. Pat. No. 8,878,682, entitled METHOD AND APPARATUS FOR DETECTION OF PHASE SEPARATION IN STORAGE TANKS USING A FLOAT SENSOR and filed Oct. 16, 2009, the entire disclosure of which is hereby expressly incorporated herein by reference. As the level of water W rises to engage float 248, float 248 rises within interior cavity 252, eventually approaching the top wall of cavity 252 and port 254. When float 248 get near enough to port 254, the concentration of vacuum pressure at port 254 draws float 248 into contact with the top wall of cavity 252 as illustrated in FIG. 26, shutting off (or substantially reducing) the flow of fluid. Because port 254 becomes blocked as a result of a high water level, shutting off the flow of fluid from filter 204B prevents any of water W from reentering UST 16.

The ceasing of fluid flow through passageway 216B also stops fluid flow at the vacuum port of eductor 230. In addition, the flow of fluid may reduce before ceasing completely. Sensor 242 detects the reduction and/or cessation of fluid flow, and issues a signal (or a lack of a signal) indicative of cessation of flow or of a reduction of flow below a predetermined threshold nominal value. Controller 102 may issue an alert and/or initiate remediation when sensor 242 indicates the high level of water W shown in FIG. 26. As described in detail above with respect to filtration system 200A, remediation may include draining of water W. To facilitate such draining, water filtration system 200B may be equipped with the same water removal passageway 208 and associated structures found in filtration system 200A, as shown in FIG. 22 and described in detail above. When water W is removed from tank 205B, float 248 falls away from port 254 toward its bottom-seated position shown in FIG. 25, once again allowing fluid to flow through the vacuum port of eductor 230.

As noted above, water filter 204B may be located within a sump (e.g., sump 32 shown in FIG. 23) and therefore near or above grade. Because water W may be allowed to accumulate within tank 205B, below-freezing weather has the potential to create ice within tank 205B. To address this potential in cold-weather installations, a temperature probe may be installed within or on the outside wall of tank 205B and configured to issue a signal to controller 102 or a system operator. When the temperature probe indicates temperatures near, at, or below freezing, the operator or controller 102 may initiate a flow of fuel from UST 16 through filter 204B, as described herein. Because the UST 16 is located underground and well below grade, the incoming fuel is reliably above freezing and can be used to maintain the internal temperature of tank 205B above freezing. This incoming flow may be maintained until the temperature probe reaches a threshold above-freezing temperature, regardless of whether controller 102 is calling for fuel flow for filtration purposes. Although this temperature-control system and method are described with respect to filtration system 200B, the same system may also be applied in the same way to other filtration systems made in accordance with the present disclosure, including systems 200, 200' and 200A.

Turning now to FIGS. 28-34, filtration system 200C includes another separator-type filter 204C and is otherwise similarly constructed to filtration systems 200A, 200B described above. Common reference numbers are used for common components of systems 200', 200A, 200B and 200C, and structures of filtration system 200C have reference numbers which correspond to similar or identical structures of filtration systems 200', 200A and 200B, except with "C" appended thereto as further described below. Filtration system 200C has all the same functions and features as filtration systems 200A, 200B described above, except as noted below. Filtration systems 200', 200A, 200B and 200C may be used interchangeably in connection with fuel delivery system 10 and its associated systems.

Like filtration system 200B, the components of filtration system 200C are sized and configured to fit within sump 32, together with a typical set of existing components including turbine pump 22, delivery lines 18 and associated shutoff valves and ancillary structures, although sump 32 is not illustrated with filtration system 200C. Unlike filtration system 200B, mounting bracket 240 is not needed, as filter 204C is directly supported atop cover 602 by rods 600 (see also, FIGS. 31, 32).

Like filtration systems 200, 200', 200A and 200B described above, filtration system 200C may also be applied to other sumps or parts of fuel delivery system 10, such as dispenser sump 30 (FIG. 1). Also similar to systems 200', 200A and 200B, system 200C uses a diverted flow of fuel from submersible turbine pump 20 as the primary driver of fluid flows through eductor 230 (although other motive devices, as described herein with respect to alternative filters may be utilized), via inlet passageway 202C and strainer 205 (FIGS. 28, 29), such that pump 20 provides the primary motive force for filtration.

Fuel flows downstream to fuel return passageway 206C to return to underground storage tank 16 (FIG. 24A, 28), passing eductor 230 to create vacuum pressure in filter return passageway 216C, which in turn transmits the vacuum pressure to the interior of tank 604. This vacuum pressure within tank 604 is sufficient to draw fuel from UST 16 via filtration uptake line 234C (FIGS. 28, 29, 31, 32, 34), which extends to the bottom of UST 16 as illustrated with respect to uptake line 234B shown in FIG. 24A and also described in detail herein with respect to other filtration system configurations. The fuel drawn through uptake line 234C provides a slow and steady flow into the bottom of tank 604 via inlet 606 (FIGS. 31, 32, 34) at the bottom of tank 604. Inlet 606 is utilized in lieu of dip tube 214B described herein with respect to filtration system 200A.

During steady-state operation, the vacuum in return passageway 216C draws fuel back to the primary return flow through fuel return passageway 206C.

Figure 30:
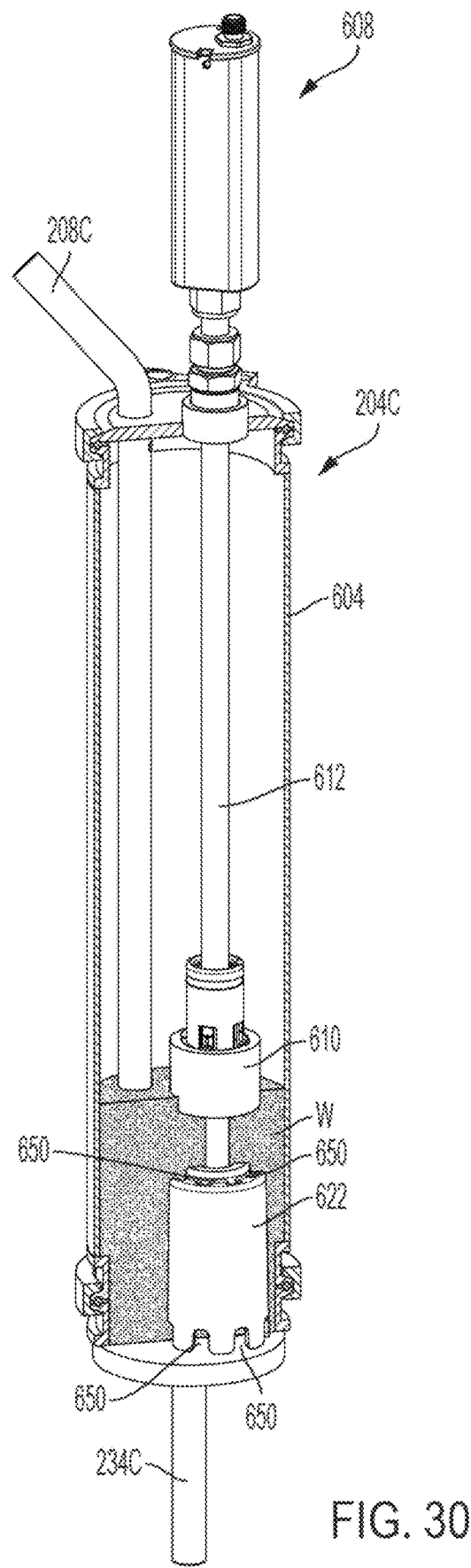
FIG. 30 is a partial sectional view of a filter of the present disclosure illustrating a water float buoyant on a quantity of water therein.

Turning now to FIG. 30, filter 204C is shown partially filled with water W and, during steady-state operation, the remainder of tank 205C is filled with fuel floating above water W, owing to the greater density of water W relative to fuel. Fuel drawn into tank 604 via inlet 606 rises to float on the heavier water W, while any water contained in the deposited fuel stratifies to remain in water W. Pure fuel is, at steady state, continuously drawn into return passageway 216C, which is in fluid communication with the top of tank 604, to be returned to UST 16.

In the embodiment of FIGS. 28-34, water filtration system 200C features flow/water level sensor subassembly 608 (more generally referred to herein as "probe 608"), which provides outputs indicative of whether a flow is being received into tank 604 via inlet 606 as well as the level of water W contained in tank 604 to allow planned/timely withdrawal thereof. Referring to FIGS. 29-33, flow/water level sensor subassembly 608 is provided to facilitate monitoring and/or controlling water filtration system 200C.

Flow/water level sensor subassembly 608 includes water float 610 which, similar to float 248 described with reference to water filtration system 200B, has a density below that of water W, but above that of the hydrocarbon fuel stratified above water W as described above. Like float 248, float 610 can be made in accordance with U.S. Pat. No. 8,878,682, the entire disclosure of which is incorporated by reference above. Water float 610 is buoyant on water W, as described above; therefore, water float 610 can be utilized to provide an output indicative of the level of water W in tank 604 to allow a fueling station manager to timely schedule removal of water W from tank 604. In certain exemplifications thereof, water float 610 including a two-piece plastic housing held together with a low density float material. The float assembly will house magnet 616 (described below) and ballast washers used to set the correct buoyancy.

In the embodiment illustrated in FIGS. 28-34, flow/water level sensor subassembly 608 includes probe shaft 612 including an elongated magnetostrictive transducer. Probe shaft 612 may be the shaft of an LL3 Magnetostrictive Probe available from Franklin Fueling Systems of Madison, Wis. Water float 610 includes central longitudinal aperture 614 therethrough. Central longitudinal aperture 614 of water float 610 is sized to receive probe shaft 612 such that water float 610 is freely reciprocatable along longitudinal axis L (FIG. 31) of probe shaft 612. Water float 610 carries magnet 616. In the exemplification illustrated, magnet 616 comprises a ring magnet surrounding probe shaft 612. The magnetostrictive transducer of probe shaft 612 is able to sense the position of water float 610 along probe shaft 612 via magnet 616 and provide the same in an output signal. This signal may be received by controller 102, for example, or may simply be received by an indicator such as bank of lights. Advantageously, the output can communicate water levels of varying degrees, e.g., ¼ full, ½ full, ¾ full, or any other increments. Float/transducer arrangements useable with flow/water level sensor subassembly 608 are disclosed in U.S. Pat. No. 7,278,311, issued Oct. 9, 2007 and entitled LIQUID LEVEL AND DENSITY MEASUREMENT DEVICE, the entire disclosure of which is hereby explicitly incorporated by reference herein.

The water level output from probe 608 may be provided to a tank gauge (e.g., controller 102), which can be programmed to provide an indication to a fuel station manager of the water level in tank 604. The tank gauge may also provide an alarm when tank 604 is full of water. Water can be removed from tank 604 via water removal passageway 208C. In certain embodiments, water removal passageway 208C is a capped metal tube. To remove water, the cap is removed and a length of flexible tubing is inserted through the internal diameter of the metal tube. The flexible tubing could be connected to a hand pump or other pumping device to remove the water from tank 604. The metal tube can feature a breather hole to allow air to enter the top of the separator vessel as the water is pumped out.

Figure 31:
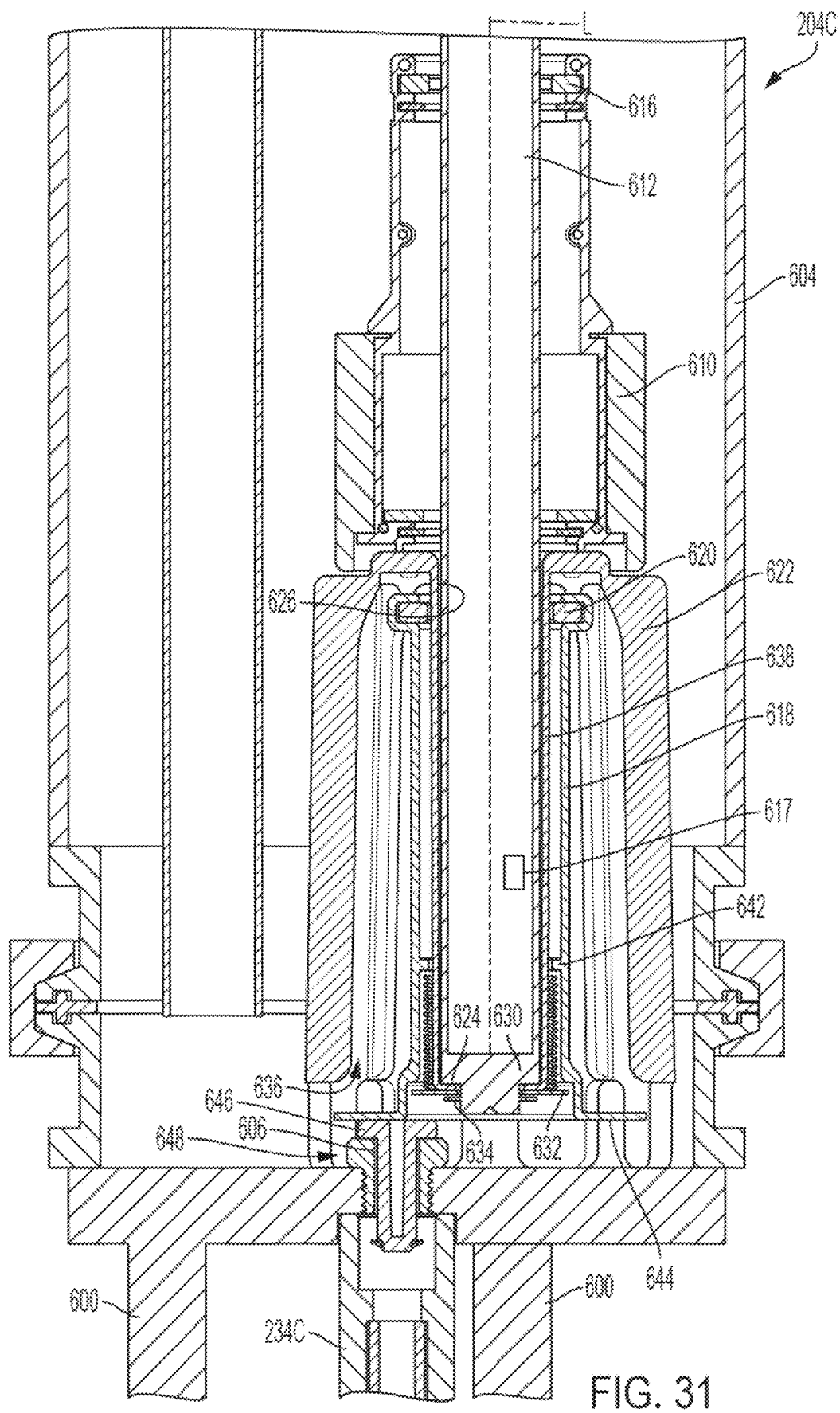
FIG. 31 is a partial, sectional view of a fuel/water level/flow sensor subassembly shown in a no-flow condition.
Figure 32:
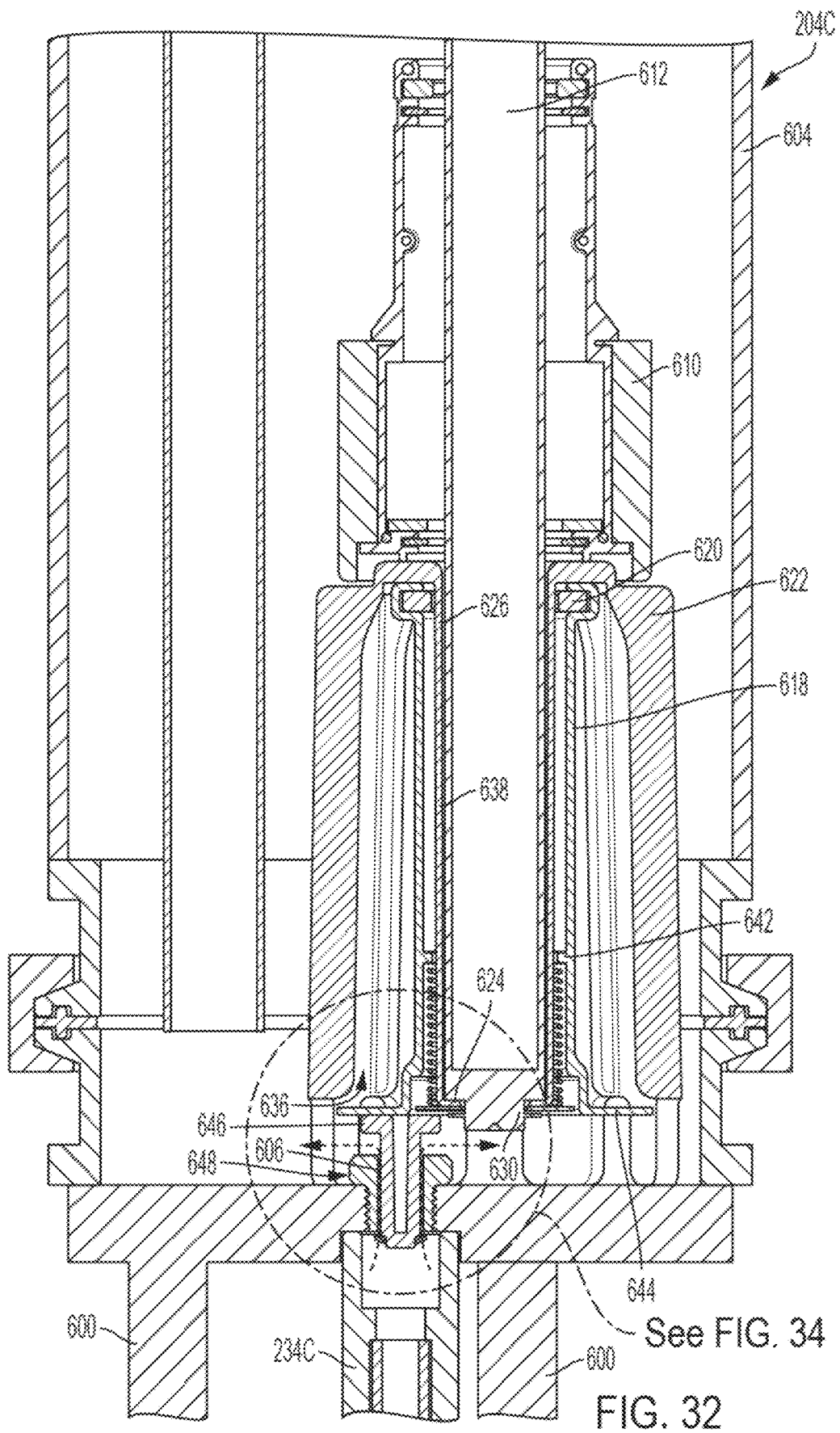
FIG. 32 is a partial, sectional view of a fuel/water levels/flow sensor subassembly shown in a flow condition.
Figure 33:
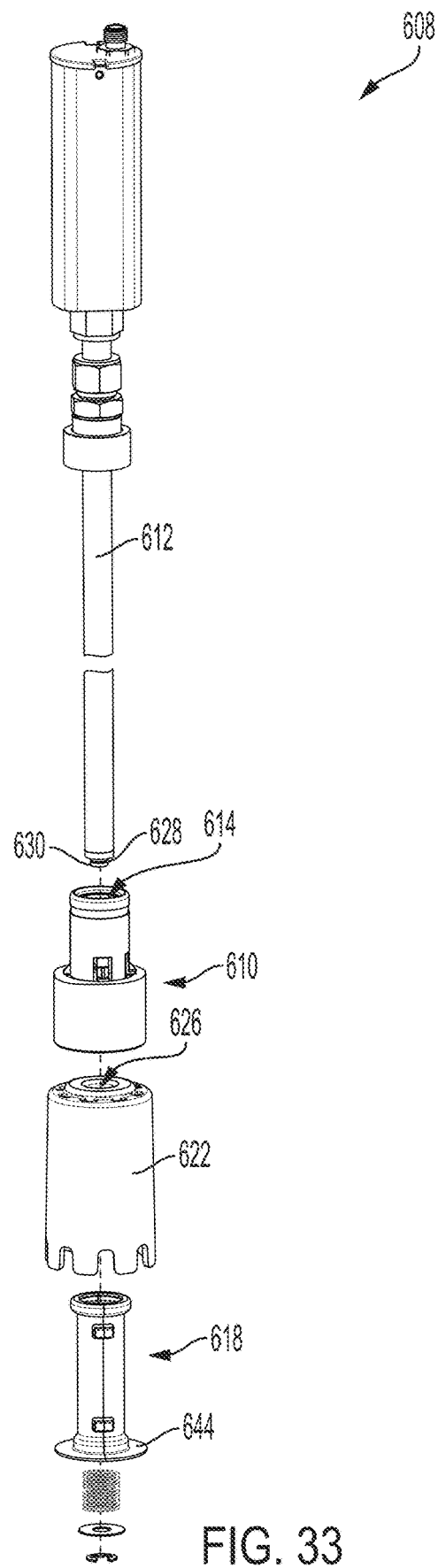
FIG. 33 is an exploded, perspective view of the fuel/water level/flow sensor subassembly shown in FIGS. 31 and 32.

In addition to providing an output indicative of the level of water W in tank 604, flow/water level sensor subassembly 608 is further operable to detect and report the presence or absence of flow through inlet 606. Specifically, flow/water level sensor subassembly 608 includes flow sensing shuttle 618 which cooperates with the magnetostrictive transducer of probe shaft 612 to alternatively signal flow and no-flow conditions through inlet 606. FIG. 31 illustrates flow sensing shuttle in a no-flow position indicative of no (or insufficient) flow through inlet 606, while FIG. 32 illustrates flow sensing shuttle raised to the flow position indicative of an operative flow through inlet 606. Operation of flow sensing shuttle will be further described hereinbelow.

Flow/water level sensor subassembly 608 includes isolator 622 fixed to probe shaft 612. Isolator 622 includes radially inward flange 624 (FIGS. 31, 32 and 34) secured against a distal end of probe shaft 612. Specifically, probe shaft 612 is inserted into central longitudinal aperture 626 of isolator 622 until distal end 628 (FIGS. 33, 34) of probe shaft 612 abuts radially inward flange 624 (this assembly step is effected with water float 610 already positioned about probe shaft 612, as described above). With isolator 622 maintaining this position, washer 632 is positioned as shown, e.g., in FIGS. 31, 32 and 34 and E-Clip 634 is secured in a fixed position along longitudinal axis L of probe shaft 612 to thereby fix the position of isolator 622 in a fixed position along longitudinal axis L of probe shaft 612. Isolator 622 functions to separate water float 610 from flow sensing shuttle 618 so that the position of water float 610 cannot influence the position of flow sensing shuttle 618 (and vice versa).

Prior to placing washer 632 and E-Clip 634 in fixed position, as described above, flow sensing shuttle 618 is inserted into central opening 636 of isolator 622. Particularly, flow sensing shuttle 618 is positioned over interior wall 638 of isolator 622 such that flow sensing shuttle 618 is freely reciprocatable along longitudinal axis L (FIG. 31) of probe shaft 612 along interior wall 638 of isolator 622. With flow sensing shuttle positioned about interior wall 638 of isolator 622, compression spring 34 (FIG. 34) is similarly positioned about interior wall 638 of isolator 622 before placement of washer 632 and securement of E-Clip 634, as described above. With assembly of flow/water level sensor subassembly 608 complete, compression spring 640 is sandwiched between washer 632 and radially inward flange 642 of flow sensing shuttle 618. In this, assembled position, flow sensing shuttle has travel limits defined by isolator 622 and a stop comprising washer 632 and/or E-Clip 634.

Figure 34:
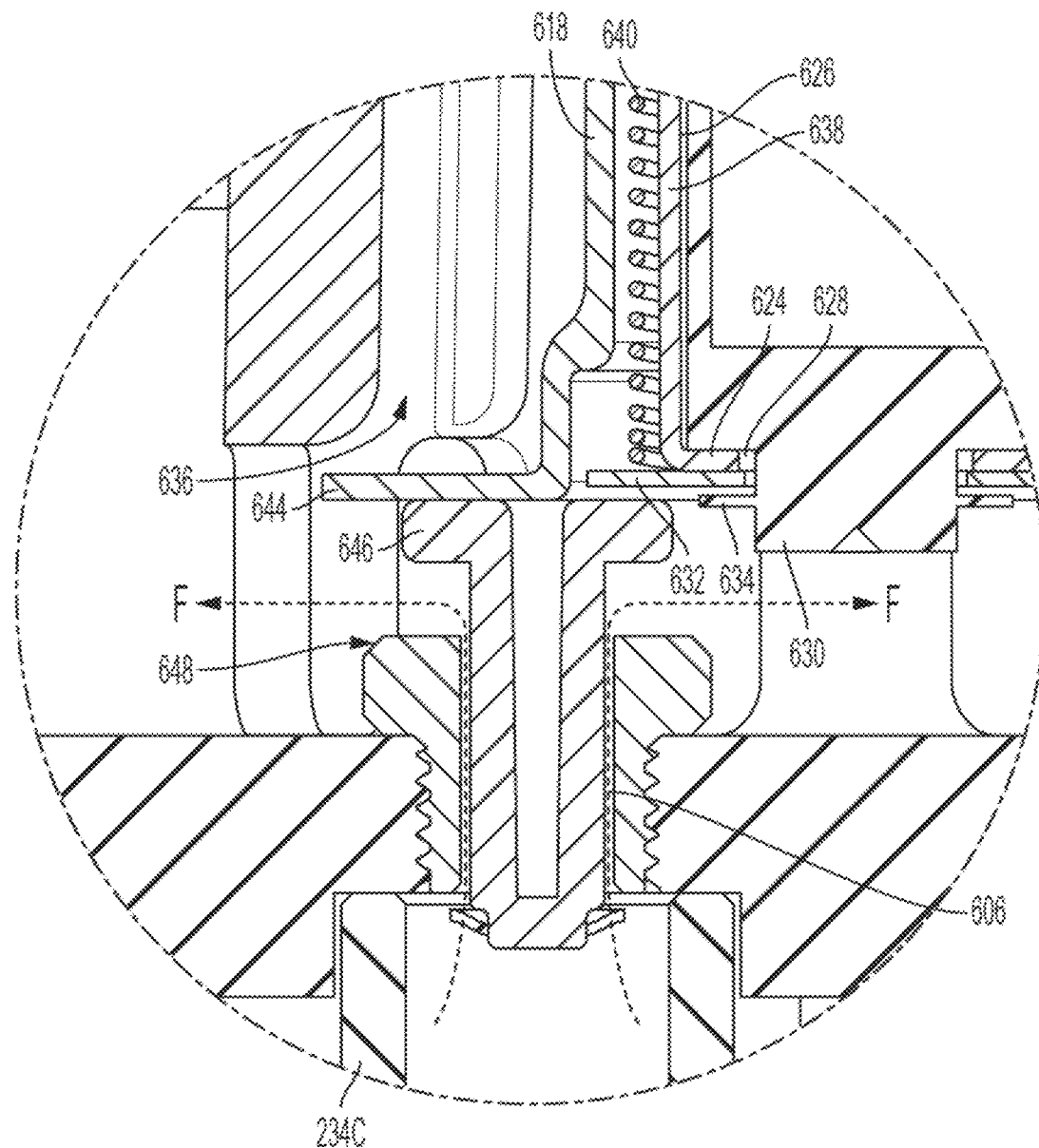
FIG. 34 is an exploded view illustrating actuation of a flow sensing shuttle of a probe in accordance with the present disclosure.

In the use position of flow/water level sensor subassembly 608 shown in FIGS. 31, 32 and 34, the weight of flow sensing shuttle 618 is sufficient to compress compression spring 640. This is also true when tank 604 contains fuel and/or water because flow sensing shuttle 618 is not buoyant on liquid fuel product 14 or water W. Flow sensing shuttle 618 is, in one exemplary embodiment, constructed with a density substantially greater than liquid fuel product 14 and/or water, e.g., a density twice that of liquid fuel product 14 and 60-75% more dense than water. With flow sensing shuttle 618 positioned for use, as illustrated in FIGS. 31, 32 and 34, compression spring 640 maintains a compressed, energy storage position in which compression spring 640 has sufficient stored energy to lift at least 25% of the weight of flow sensing shuttle 618. With compression spring 640 relieving a portion of the weight of flow sensing shuttle 618, flow sensing shuttle 618 is still not buoyant on liquid fuel product 14 or water W. In certain exemplifications, compression spring 640 may make flow sensing shuttle 618 neutrally buoyant in the fluid contained in tank 604, i.e., flow sensing shuttle 618 will have a buoyant force substantially balancing the force of gravity. In certain exemplifications this neutral buoyancy is keyed to water, i.e., flow sensing shuttle 618 will, owing to compression spring 640, be neutrally buoyant in water. In alternative forms of the disclosure, the shuttle may be made of material such that the shuttle alone would be buoyant on water; however, a spring or other elastically deformable member is utilized to bias the shuttle to a neutral buoyancy. For example, the shuttle could be spring biased to the no flow position by, e.g., a spring, and moveable to the flow position against the biasing force of the spring.

Flow/water level sensor subassembly 608 is positioned for use with the distal end of isolator 622 indexing probe 608 to filter 204C. Specifically, probe 608 is inserted into tank 604 until the distal end of isolator 622 rests atop the floor of tank 604. In this position, flow from the inside of isolator 622 to the exterior of isolator 622 is allowed by passages 650 (FIG. 30). With probe 608 positioned in this fashion, the proximal end thereof can be bung mounted to the lid of tank 604, with a proximal end of probe 608 extending from tank 604 to, e.g., facilitate easy electrical connection to controller 102 or an indicator. With probe 608 positioned for use, distal flange 644 of flow sensing shuttle 618 is positioned atop plunger 646 of plunger valve 648. When a vacuum is created in tank 604, as described above, plunger 646 is unseated from plunger valve 648 to allow a flow from UST 16 to tank 604 through inlet 606. This unseating of plunger 646 via the flow from UST 16 to tank 604 causes plunger 646 to cooperate with compression spring 640 to lift flow sensing shuttle 618 from the no-flow position illustrated in FIG. 31 to the flow position illustrated in FIG. 32. Specifically, as plunger 646 is moved upwardly by the fluid drag of flow F (FIG. 34), compression spring 640 is actuated to an energy release position in which the stored energy of compression spring 640 cooperates with fluid flow F to actuate flow sensing shuttle 618 to the flow position. Alternative biasing elements may be utilized in lieu of compression spring 640. For example a tension spring could be utilized.

Flow sensing shuttle 618 carries magnet 620. In the exemplification shown, magnet 620 comprises a ring magnet. The magnetostrictive transducer of probe shaft 612 is able to sense the position of flow sensing shuttle 618 along probe shaft 612 via magnet 620 and provide the same in an output signal. This signal may be received by controller 102, for example, or may simply be received by an indicator such as bank of lights. In an exemplary embodiment, flow sensing shuttle 618 has a travel of ⅛ inch between the flow and no-flow positions. Spring 640 not only facilitates actuation of flow sensing shuttle 618, but also facilitates proper operative placement of probe 608 without requiring exacting tolerances. Specifically, placement of flow sensing shuttle 618 atop plunger 646 may release some of the compression of compression spring 640 when probe 608 is operatively positioned. In certain exemplary embodiments, flow sensing shuttle will work together with a tank gauge (e.g., controller 102) to alert a fuel station manager if the filter flow is not operating properly. Specifically, if fuel is flowing from UST 16 for dispensing through dispensers 12 such that educator 230 should be drawing flow through tank 604 (or filtration system 200C is otherwise running) and flow sensing shuttle 618 should thereby be actuated to its flow sensing position, the tank gauge (e.g., controller 102) or an indicator will indicate a fault if probe 608 does not detect flow sensing shuttle 618 in the flow sensing position. The fault may be an advisement that maintenance needs to be performed on the system.

Probe shaft 612 may further incorporate a temperature sensor 617, such as one or more thermistors to combat freezing within tank 604. As noted above, water filter 204C may be located within a sump (e.g., sump 32 shown in FIG. 23) and therefore near or above grade. Because water W may be allowed to accumulate within tank 604, below-freezing weather has the potential to create ice within tank 604. To address this potential in cold-weather installations, the thermistors within probe shaft 612 may be configured to issue a signal to controller 102 or a system operator. When the temperature probe indicates temperatures near, at, or below freezing, the operator or controller 102 may initiate a flow of fuel from UST 16 through filter 204C, as described herein. Because the UST 16 is located underground and well below grade, the incoming fuel is reliably above freezing and can be used to maintain the internal temperature of tank 205B above freezing. This incoming flow may be maintained until the temperature probe reaches a threshold above-freezing temperature, regardless of whether controller 102 is calling for fuel flow for filtration purposes. Although this temperature-control system and method are described with respect to filtration system 200C, the same system may also be applied in the same way to other filtration systems made in accordance with the present disclosure, including systems 200, 200', 200A and 200B.

Probe 608 provides a single device (i.e., subassembly) capable of monitoring all relevant operational parameters of filtration system 200C.

Controller 102 (FIG. 3), or a human operator, may also use inlet valve 203 to selectively activate or deactivate the fuel filtration process enabled by filtration systems 200A or 200B (or, alternatively, systems 200 or 200', it being understood that systems 200, 200', 200A and 200B may be used interchangeably as noted herein). For example, controller 102 may be programmed with a pre-determined schedule for fuel filtration, and may open valve 203 to initiate a filtration cycle. After a predetermined amount of time during which the filtration cycle is active and filtration is occurring as described above, controller 102 may close valve 203 to stop the filtration cycle. After a predetermined amount of time during which the filtration cycle is not active, a new cycle may begin. Alternatively, in some embodiments, valve 203 may be omitted or left open, such that fuel filtration occurs any time pump 20 is active.

The use of the separator-type filters 204A, 204B allow filtration systems 200A, 200B to be virtually maintenance free, with the only regular maintenance task being the periodic removal of accumulated water from filter 204A, 204B. Even this maintenance task may be automated as noted above. In contrast to filtration system 200', which uses a substrate-type filter 207 as described in detail above, filtration systems 200A, 200B have no substrate filters which would require replacement or service.

The separator-type filters 204A, 204B may also be sized to fit existing or newly-installed sumps, such as turbine sump 32 of fuel delivery system 10 (FIG. 1). As noted above, a system designer has flexibility in sizing the volume of filters 204A, 204B by controlling the flow rate of fluid to be filtered. Therefore, where there is a requirement for a filtration system to accommodate a small space within a sump, filters 204A, 204B can be sized accordingly and the nominal filtration flow rate per can be set at an appropriate percentage of the filter volume as described in detail above.

However, it is contemplated that a filter substrate, such as filter 207, or any other coalescing filter element, particulate filter element, or a combination thereof may be used inside filters 204A, 204B, as required or desired for a particular application.

As discussed herein, filtration systems 200, 200', 200A and 200B utilize submersible pump 20, already existing as a component of fuel delivery system 10, as a motive fuel flow source to power a vacuum generating device, illustrated with respect to the various embodiments as eductor 230. Although the illustrative filtration systems 200', 200A, 200B use eductor 230 to draw the contaminated fuel from the bottom of tank 16, other equipment may be used to perform this operation, such as another type of venturi device or a supplemental pump (in addition to pump 20). For example, a flow from the pump 20, including a primary and/or diverted flow, may be used to drive an impeller which drives a separate pump for filtration, similar to the operation of a turbocharger system of an internal combustion engine, which uses exhaust gases to power an impeller. The dedicated filtration pump powered by the flow of the primary pump may then be used in place of eductor 230 to drive filtration flows as described herein.

Yet another alternative is to use a dedicated, electrically powered pump for filtration flows. This dedicated pump may be used in place of eductor 230 or 230A as shown in FIGS. 15 and 22, for example. In this configuration of filtration system 200, 200', 200A or 200B, fuel return passageway 206, 206A or 206B is used only for return of filtered fuel flows, with no need for a separate motive flow of fuel as described herein with respect to venturi-based systems. The dedicated filtration pump may have a low-flow configuration sufficient for only the filtration flow desired for the throughput of filter 204, 204A or 204B.

In still another alternative arrangement, pump 20 may be configured as a diaphragm-type pump, in which a primary stroke of the pump is used for delivery of fuel to dispenser 12 via delivery line 18 (FIG. 1), while the reverse stroke can be used to drive filtration flows as described herein. In this configuration, of filtration system 200, 200', 200A or 200B eductor 230 is omitted. If the flows resulting from the reverse stroke of the diaphragm pump 20 are commensurate with the desired filtration flows through filter 204, 204A or 204B, then fuel return passageway 206, 206A or 206B is again used only for filtration flows with no separate excess or motive flow. If the flows from the reverse stroke of diaphragm pump 20 are higher than the desired flows through filter 204, 204A or 204B, then fuel return passageway 206, 206A or 206B may be also be sized to discharge excess flows back to tank 16.

Figure 13:
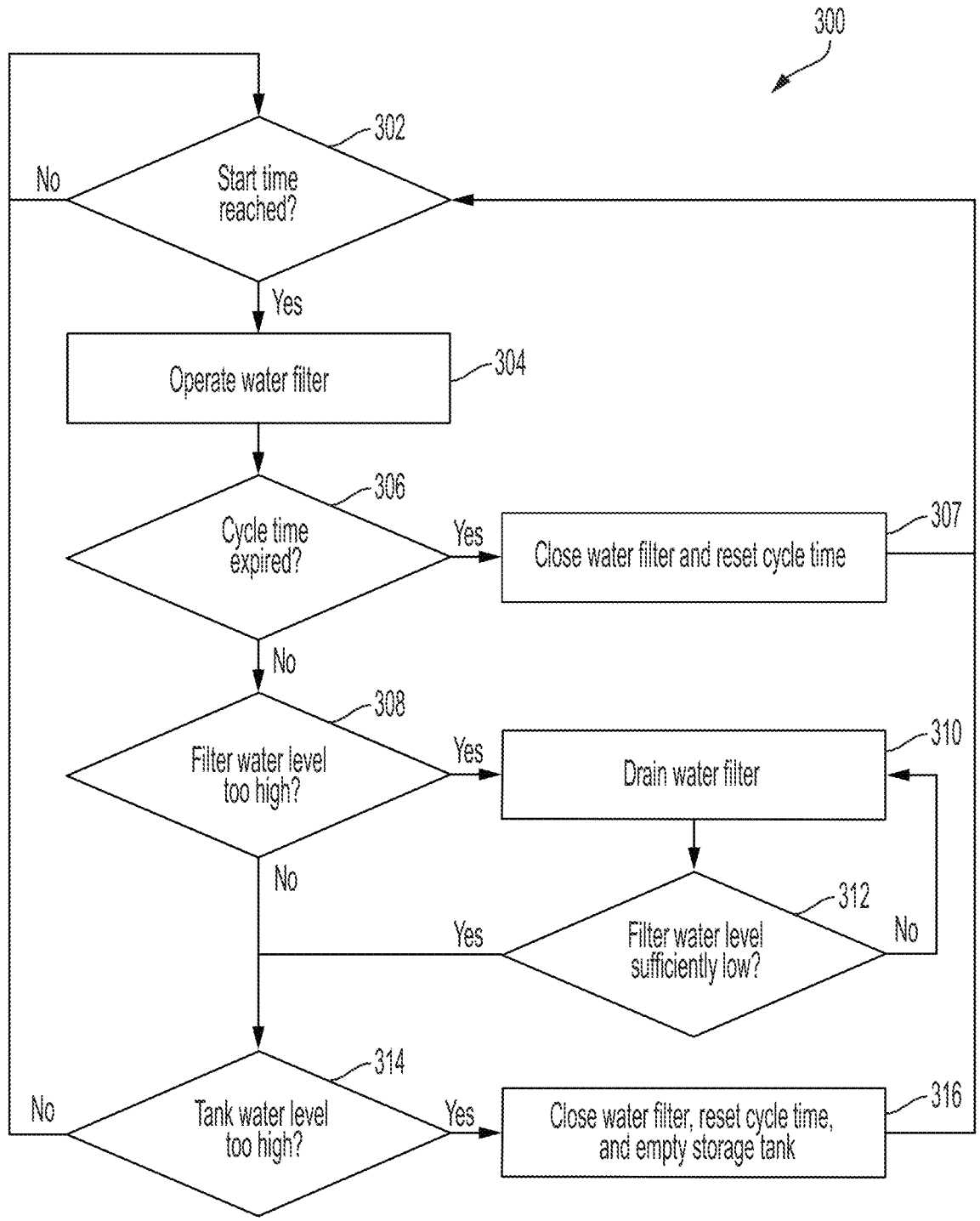
FIG. 13 shows an exemplary method for operating the water filtration system.

Referring next to FIG. 13, an exemplary method 300 is disclosed for operating water filtration systems 200, 200', 200A, 200B. Method 300 may be performed using controller 102 (FIG. 3). Method 300 is described below with reference to the illustrative water filtration system 200 of FIG. 12, though the disclosed method is also applicable to systems 200', 200A and 200B.

In step 302 of method 300, controller 102 determines whether a predetermined start time has been reached. The start time may occur at a desired time, preferably outside of high-demand fuel dispensing hours (e.g., 4:30 to 7:30 AM), and with a desired frequency. For example, the start time may occur daily at about 8:00 PM. When the start time of step 302 is reached, method 300 continues to step 304. It is also within the scope of the present disclosure that method 300 may be initiated based on an input from one or more monitors 104 (FIG. 3). It is further within the scope of the present disclosure that method 300 may be initiated only when a certain minimum level of fuel product 14 is present in storage tank 16, such as about 20 to 30 inches of fuel product 14, more specifically about 24 inches of fuel product 14.

In step 304 of method 300, controller 102 operates water filter 204 to filter fuel product 14. As discussed above, this filtering step 304 may involve opening inlet valve 203 of fuel inlet passageway 202 and activating pump 20. After passing through water filter 204, the filtered fuel product 14 may be returned continuously to storage tank 16 via fuel return passageway 206.

In step 306 of method 300, controller 102 determines whether a predetermined cycle time has expired. The cycle time may vary. For example, the cycle time may be about 1-10 hours, more specifically about 7-9 hours, and more specifically about 8 hours. If the cycle time has expired, method 300 continues to step 307, in which controller 102 closes inlet valve 203 of fuel inlet passageway 202 to water filter 204 and resets the cycle time before returning to step 302 to await a new start time. If the cycle time has not yet expired, method 300 continues to step 308.

In step 308 of method 300, controller 102 determines whether a water level in water filter 204 is too high. Step 308 may involve communicating with the high-level water sensor 220 in water filter 204. If the high-level water sensor 220 detects water (i.e., activates), method 300 continues to steps 310 and 312. If the high-level water sensor 220 does not detect water (i.e., deactivates), method 300 skips steps 310 and 312 and continues to step 314.

In step 310 of method 300, controller 102 drains the separated water product from water filter 204. As discussed above, this draining step 310 may involve opening drain valve 209 of water removal passageway 208. From step 310, method continues to step 312.

In step 312 of method 300, controller 102 determines whether a water level in water filter 204 is sufficiently low. Step 312 may involve communicating with the low-level water sensor 222 in water filter 204. If the low-level water sensor 222 still detects water (i.e., activates), method 300 returns to step 310 to continue draining water filter 204. Once the low-level water sensor 222 no longer detects water (i.e., deactivates), method 300 continues to step 314. Controller 102 may initiate an alarm if the draining step 310 is performed for a predetermined period of time without deactivating the low-level water sensor 222. Controller 102 may also initiate an alarm if a discrepancy exists between the high-level water sensor 220 and the low-level water sensor 222, specifically if the high-level water sensor 220 detects water (i.e., activates) but the low-level water sensor 222 does not detect water (i.e., deactivates).

In step 314 of method 300, controller 102 determines whether a water level in storage tank 210 is too high. Step 314 may involve communicating with the high-level water sensor 224 in storage tank 210. Step 314 may also involve calculating the volume of water contained in storage tank 210 based on prior draining steps 310 from water filter 204. This volume calculation may involve logging the number of draining steps 310 from water filter 204 triggered by the high water-level sensor 220 and determining the known volume of water drained between sensors 220 and 222 during each draining step 310. If the high-level water sensor 224 does not detect water (i.e., deactivates) or the calculated water volume inside storage tank 210 is lower than a predetermined limit, method 300 returns to step 304 to continue operating water filter 204. If the high-level water sensor 224 detects water (i.e., activates) or the calculated water volume inside storage tank 210 reaches the predetermined limit, method 300 continues to step 316.

In step 316 of method 300, controller 102 initiates an alarm or sends another communication requiring storage tank 210 to be emptied and replaced. Controller 102 also closes inlet valve 203 of fuel inlet passageway 202 and resets the cycle time. After storage tank 210 is emptied and replaced, controller 102 returns to step 302 to await a new start time.

In a fourth embodiment, remediation system 108 is configured to control the humidity in turbine sump 32 of fuel delivery system 10. In the illustrated embodiment of FIG. 2, remediation system 108 includes a desiccant 400 (e.g., calcium chloride, silica gel) that is configured to adsorb water from the atmosphere in turbine sump 32. Desiccant 400 may be removably coupled to turbine sump 32, such as being detachably suspended from lid 38 of turbine sump 32. In this embodiment, monitor 104"" may be a humidity sensor that is configured to measure the humidity in the vapor space of turbine sump 32. Monitor 104"" may also be configured to measure the temperature in the vapor space of turbine sump 32. The humidity and/or temperature data may be communicated to controller 102 (FIG. 3). When the humidity level increases above a predetermined level (e.g., 40%), output 106 may instruct the operator to inspect turbine sump 32 and/or to replace desiccant 400.

The above-described embodiments of remediation system 108 may be provided individually or in combination, as shown in FIG. 2. Thus, remediation system 108 may be configured to ventilate turbine sump 32 of fuel delivery system 10, irradiate bacteria in turbine sump 32 of fuel delivery system 10, operate water filtration system 200, and/or control the humidity in turbine sump 32 of fuel delivery system 10.

Corrosion mitigation/prevention can be implemented with a water level sensor providing a signal to controller 102 to activate water filtration systems 200, 200', 200A and/or 200B (e.g., implemented by method 300). Particularly, a threshold amount of water in storage tank 16 may trigger operation of a corrosion mitigation/prevention system such as one or more of the systems described in this document. Low level water sensors to trigger operation of a corrosion mitigation/prevention system are exemplified in FIGS. 35-50. Referring to FIG. 1, water sensor 700 may be utilized to sense a level of water in the bottom of storage tank 16. Because water is more dense than the oil (i.e., motor fuel, such as gasoline and diesel, as previously defined herein), it will stratify in storage tank 16 below liquid fuel product 14.

Water level sensors are sometimes used to prevent water from being pumped by pump 20 to a vehicle. In these circumstances, the water level sensor merely needs to signal a water level approaching the intake to pump 20. Typically, the pump intake is several inches above the floor of storage tank 16, allowing a relatively imprecise water sensor (for example one that is not triggered in less than 3 inches of water) to be used. So long as the water sensor triggers a shutdown of the system before the water can reach the pump intake, these systems successfully prevent transfer of water in storage tank 16 from entering a vehicle. Corrosion can be triggered by much less water, however.

Water level sensors implemented to prevent water from being taken-up by pump 20 cannot sense a water level in storage tank 16 of less than 1 inch; however, much lower levels can trigger acidic corrosion. The present disclosure provides embodiments of water sensor 700 capable of greater precision (i.e., able to sense lower water levels).

Figure 35A:
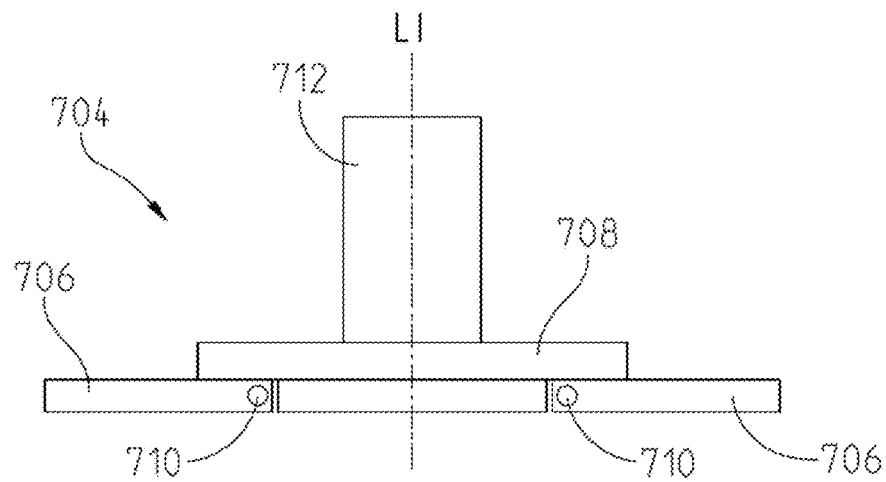
FIG. 35A is a radial elevational view of a water float having extendable wings in an extended position.
Figure 35B:
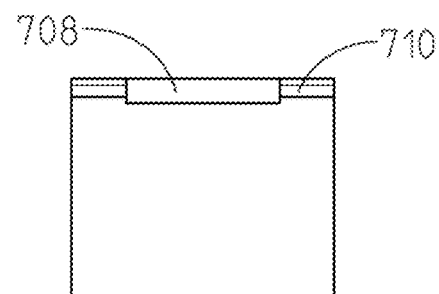
FIG. 35B is a plan view of a wing of the float of FIG. 35A.
Figure 36:
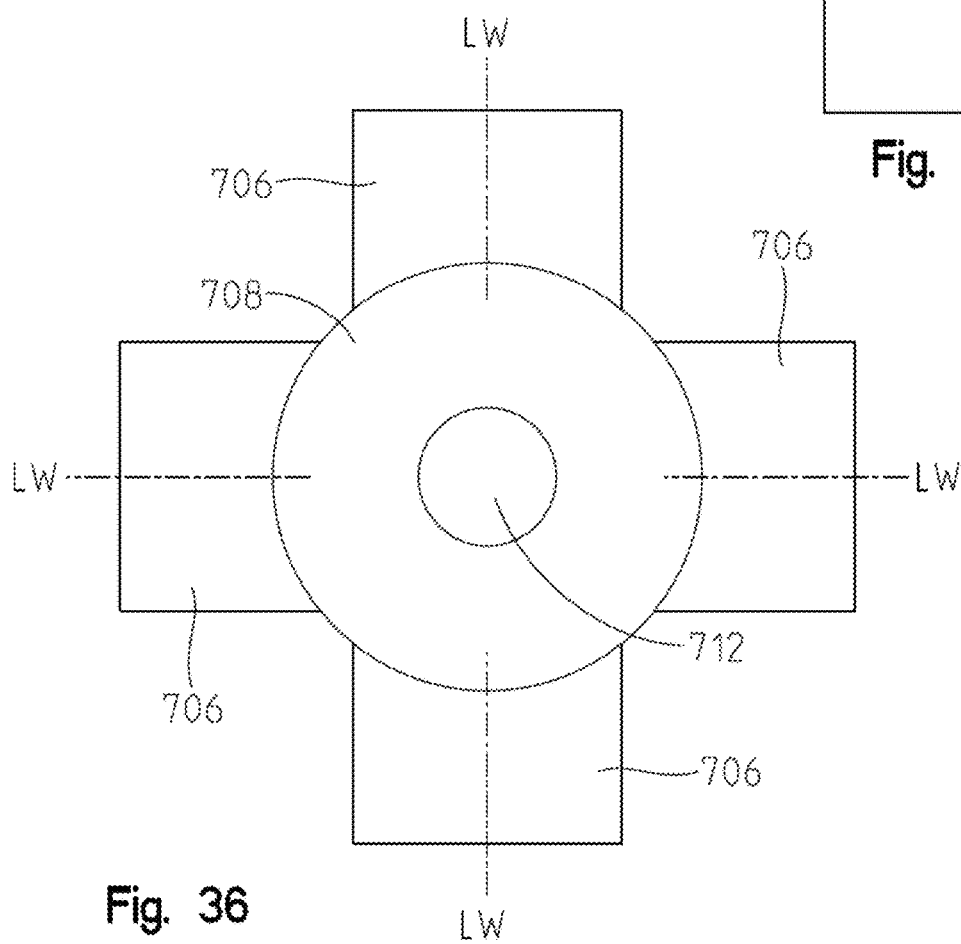
FIG. 36 is a top, plan view of the water float of FIG. 35, with the wings in the extended position.
Figure 37:
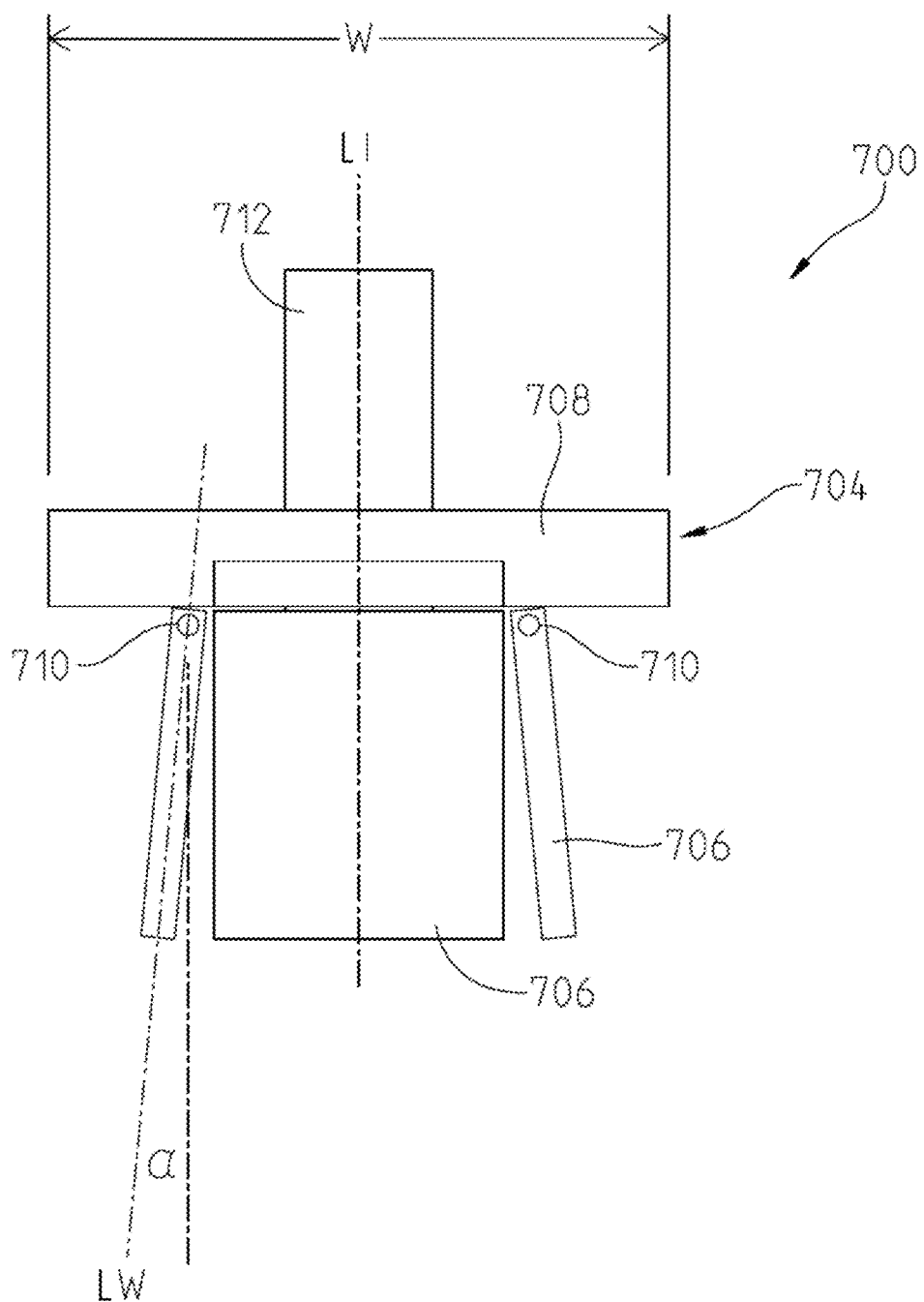
FIG. 37 is another radial elevational view of the water float of FIGS. 35 and 36, with the wings shown in a retracted position.

Referring to FIG. 35-37, water level sensor 700 is exemplified by float 704 including a central longitudinal aperture through which probe shaft 712 is positioned. Float 704 is freely reciprocatable along longitudinal axis L1 of probe shaft 712. Water float 704 carries a float magnet. Probe shaft 712 includes an elongated magnetostrictive transducer capable of sensing the position of water float 704 along the longitudinal axis of probe shaft 712 via the magnet carried by float 704 and providing the same in an output signal.

Magnetostrictive probes installed in fuel tanks work on the principle that sound, moving down a nichrome wire positioned nominally down the center of the probe shaft, maintains a constant velocity despite any encountered temperature differences. Magnetic forces can act on the nichrome wire to cause a sound wave reaching a magnet, e.g., in a float, to generate electricity in the nichrome wire. The time between the start of the sound pulse and the triggered electrical pulse is used to determine the position of the magnet (for example, a magnet in a product or water float).

When using a float riding along a probe shaft such as the embodiment of FIGS. 35-37, the displaced volume of the fluid on which the float is buoyant is key. In the case of a water float utilized in a fuel storage tank, the float is constructed to be buoyant on water, while sinking in oil, so that the float is capable of signaling the level of water in storage tank 16. A limitation on the geometry of a water float used in a fuel storage tank is found in the internal diameter of riser 702 (FIG. 1) through which the water float is introduced into the storage tank. Typical risers in the fueling industry have an internal diameter of 4 inches. With floats limited in their lateral dimensions (i.e., their extension orthogonal to longitudinal axis L1, that is, their width) by the internal diameter of the riser through which they are introduced to the tank, a relatively larger height of water can be needed to raise the float due to buoyancy, depending on other float variables. For example, a float having an appropriate density to sink in oil, but float on water and a diameter of less than 4" will many times require more than 1 inch of water to float. The embodiment of FIGS. 35-37 addresses this issue by providing more lateral volume in the form of actuatable wings 706.

Float 704 includes base 708, which, in an exemplification thereof, carries the float magnet previously described. Base 708 comprises a toroid having a central aperture through which probe shaft 712 is positioned. Each wing 706 is pivotally secured to base 708 by a pivot pin 710 displaced radially outwardly from the central aperture through which probe shaft 712 is positioned. Owing to this positioning of pivot pins 710 and the geometry of wings 706, wings 706 cannot interfere with the travel of float 704 along probe shaft 712.

Each wing 706 has an extended position as illustrated in FIGS. 35A and 36 and a retracted position as illustrated in FIGS. 35B and 37. In the retracted position, water sensor 700 extends a width W orthogonal to longitudinal axis L1 a distance less than 4 inches to accommodate introduction into storage tank 16 through riser 702 (FIG. 1) having an inner diameter of 4 inches. Water sensor 700 may, of course have a geometry compatible with risers of differing dimensions. For example, if riser 702 had an inner diameter of 6 inches, then water sensor 700 could be constructed with a width W approaching, but less than 6 inches.

Pivot pins 710 pivotally connect wings 706 to base 708 and allow wings 706 to rotate between the extended position of FIGS. 35A and 36 to the retracted position of FIG. 37. The travel of wings 706 may be limited to a position short of parallel to longitudinal axis L1 to create an angle α of 5-10 degrees when wings 706 maintain the retracted position (i.e., the position closest to parallel to longitudinal axis L1), with angle α being measured between the longitudinal axis LW of wing 706 and a line parallel to longitudinal axis L1 and intersecting the axis of rotation of pivot pin 710. At the other end of travel of wings 706, base 708 creates a stop positioning wings 706 nominally orthogonal to longitudinal axis L1 (i.e., with LW nominally orthogonal to L1) in the extended position. In the extended position illustrated in FIGS. 35A and 36, float 704 is capable to displacing a sufficient volume of water to float on a layer of water having a height of less than 1 inch from the bottom of storage tank 16. In certain exemplary embodiments, float 704 is buoyant on a layer of water having a height of no more than $^{15}/_{16}$ inch, $^{7}/_{8}$ inch, $^{13}/_{16}$ inch, $^{3}/_{4}$ inch, $^{11}/_{16}$ inch, $^{5}/_{8}$ inch, $^{9}/_{16}$ inch, $^{1}/_{2}$ inch, $^{7}/_{16}$ inch, $^{3}/_{8}$ inch, $^{5}/_{16}$ inch, $^{1}/_{4}$ inch, $^{3}/_{16}$ inch, $^{1}/_{8}$, or $^{1}/_{16}$ inch from the floor of storage tank 16.

Without a buoyant or other force acting on wings 706, gravity will position wings 706 in the retracted position illustrated in FIG. 37 when water sensor 700 is oriented as shown in FIG. 37. In this position, water sensor 700 can traverse the interior of riser 702 and be introduced into storage tank 16 or removed from storage tank 16. As water sensor 700 encounters fluid in storage tank 16, wings may be deployed to the extended position shown in FIGS. 35A and 36. To facilitate such deployment, water sensor 700 may be accelerated downwardly through the liquid contents of storage tank 16, with the resistance to such acceleration presented by the liquid contents of storage tank 16 causing wings 706 to rotate about pivot pins 710 from the retracted position of FIG. 37 to the extended position of FIGS. 35 and 36.

In the extended position of wings 706, float 704 is placed adjacent to or atop the floor of storage tank 16 in a use position. The use position may correspond to float 704 abutting, at least in part (e.g., the radially distal portions of wings 706), the floor of storage tank 16 or being spaced a distance of ¼ inch or less from the bottom of storage tank 16. For example, float 704 may be spaced no more than $^{1}/_{16}$, $^{1}/_{8}$, $^{3}/_{16}$ or ¼ inch from the floor of storage tank 16 in the use position, with these distances or any distances therebetween being considered to place float 704 "adjacent" to the floor of storage tank 16.

Referring to FIG. 1, storage tank 16 is exemplified as a cylindrical storage tank. Storage tank is, in certain exemplary embodiments, a cylindrical tank having a diameter of 8 or 10 feet. To account for the geometry of the floor of cylindrical storage tank 16, wings are, in certain alternative exemplifications, curved along longitudinal axis LW and curved along a line orthogonal to longitudinal axis LW. Float 704 is exemplified with four wings 706, but may implement any number of wings to achieve the needed buoyancy.

In use, probe shaft 712 is communicatively connected to controller 102 or an indicator to relay a water measurement and/or alarm to a user. A threshold measured water level may signal actuation of filtration systems 200, 200', 200A, or 200B. A threshold measured water level may also signal corrosion mitigation in the form of water removal from storage tank 16 by direct pumping from the floor of storage tank 16 or other mechanisms.

FIGS. 42-50 illustrate an alternative water sensor 1700. Water sensor 1700 includes water float 1704. FIGS. 51-55 illustrate an alternative water float 1704', which can replace water float 1704 in water sensor 1700. Water floats 1704, 1704' will be described together, it being understood that only one water float 1704, 1704' will be implemented in a particular water sensor 1700. Water float 1704, 1704' includes toroidal float base 1708, 1708' having an outer diameter measured orthogonal to longitudinal axis L1 of magnetostrictive probe shaft 1712 of 2.725 inches. Alternatively, any diameter of less than the 4 inch riser diameter may be used for float base 1708, 1708'. This outer diameter defines the lateral maximum extent of water float 1704, 1704'. Attached to float base 1708, 1708' is frame 1701, 1701'. Frame 1701, 1701' carries water float magnet 1703, 1703', which cooperates with magnetostrictive probe shaft 1712 as described above to provide the position of water float 1704, 1704' relative to the bottom of UST 16 in the form of an output signal receivable, e.g., by controller 102 or an indicator such as an alarm.

The embodiments of water float 1704, 1704' illustrated in FIGS. 42-50 and 51-55 are useful with a magnetostrictive probe shaft 1712 that includes a datum magnet at distal end 1705 of magnetostrictive probe shaft 1712. This arrangement is common with magnetostrictive probes used with fuel storage tanks and; therefore, these embodiments of the present disclosure find particular applicability in their ability to be retrofit to existing magnetostrictive probes. Datum magnets are useful in establishing the low point of the probe shaft and a datum against which float position can be measured.

Water float 1704, 1704' is particularly useful with a datum magnet at distal end 1705 of magnetostrictive probe shaft 1712 because frame 1701, 1701' ensures that water float magnet 1703, 1703' is always spaced a minimum of about 3.0 inches from the datum magnet at distal end 1705 of magnetostrictive probe shaft 1712. If 2 magnets are closer than about 3.0 inches along magnetostrictive probe shaft 1712, then the probe will not be able to function properly by identifying the position of the 2 magnets. Frame 1701, 1701' acts as a spacer to space water float magnet 1703, 1703' from toroidal float base 1708, 1708' to allow for measuring low levels of water (as that term is further described herein) in UST 16.

Figure 44A:
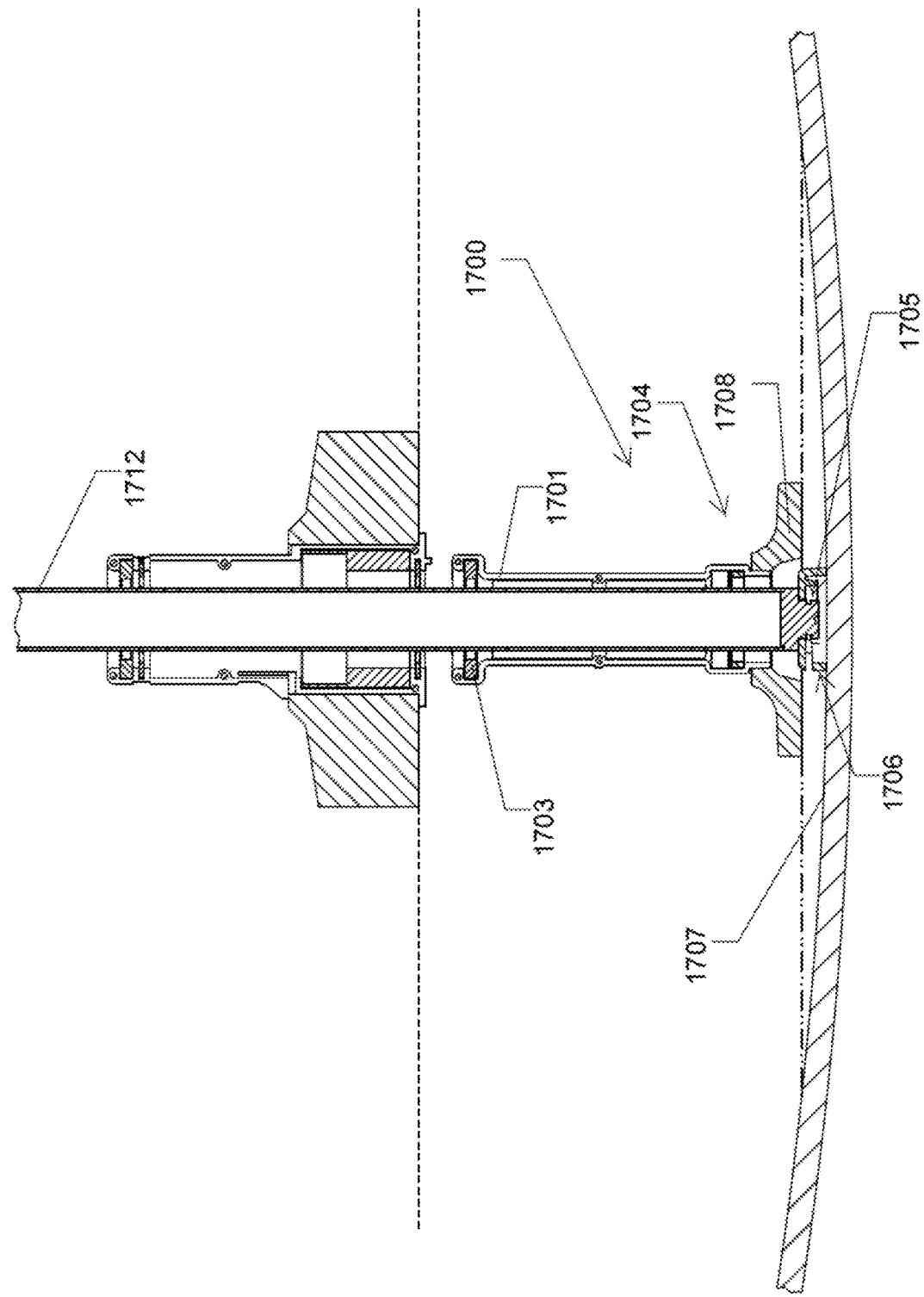
FIG. 44A is a sectional view of the combination of FIG. 43.
Figure 44B:
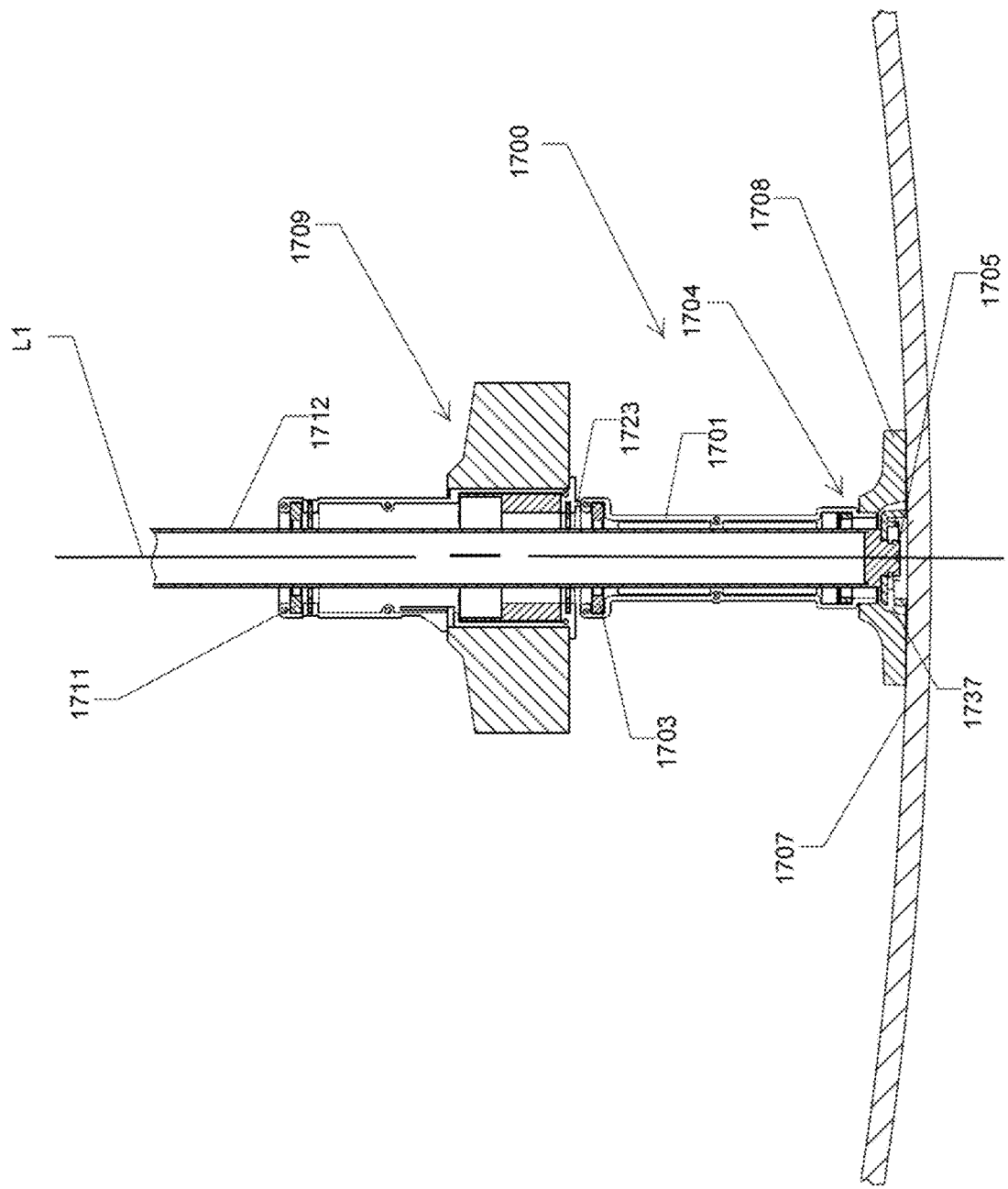
FIG. 44B is a sectional view like FIG. 44A, but without any water or fuel.
Figure 45:
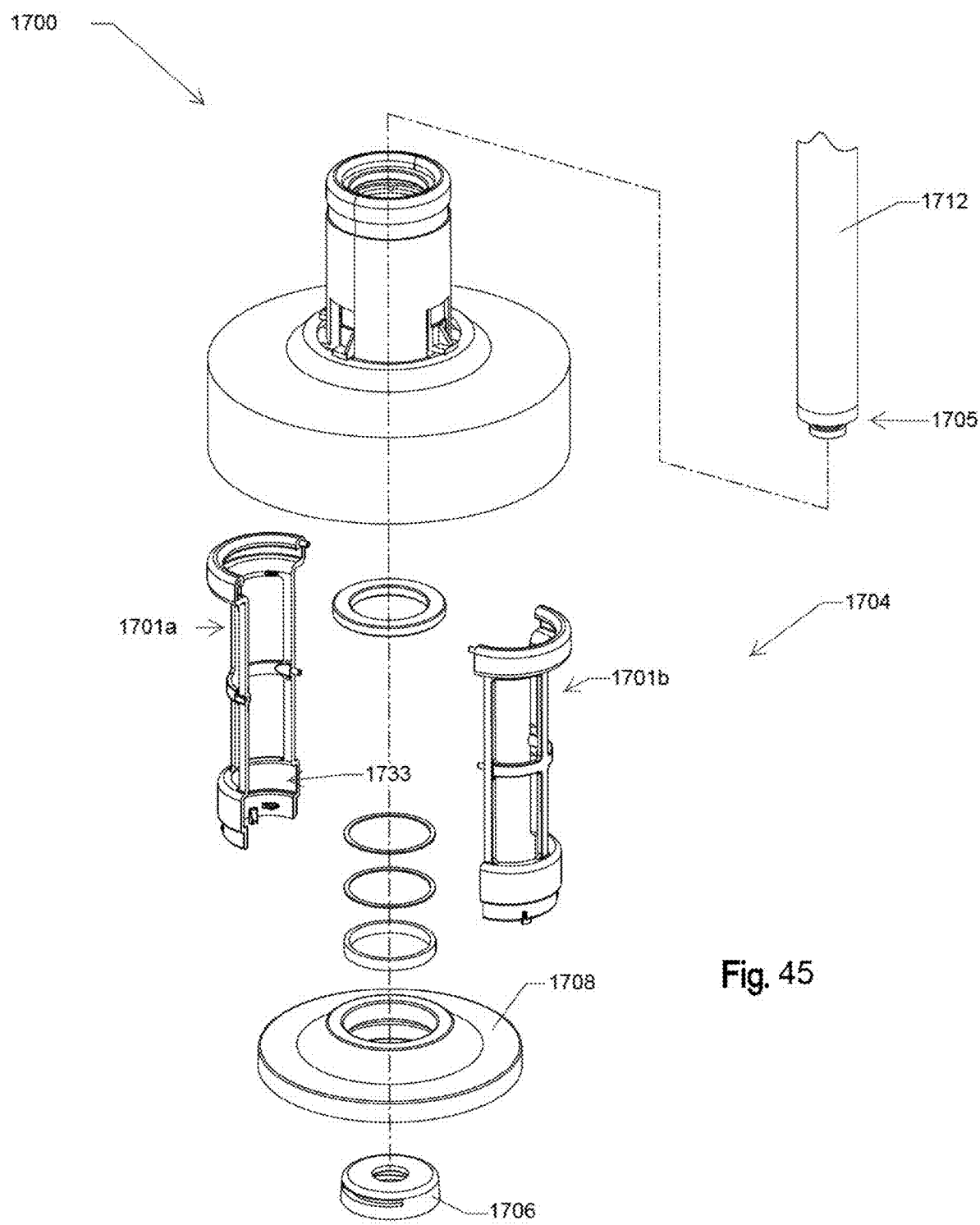
FIG. 45 is an exploded, perspective view of the tank probe of FIGS. 42-44.
Figure 46:
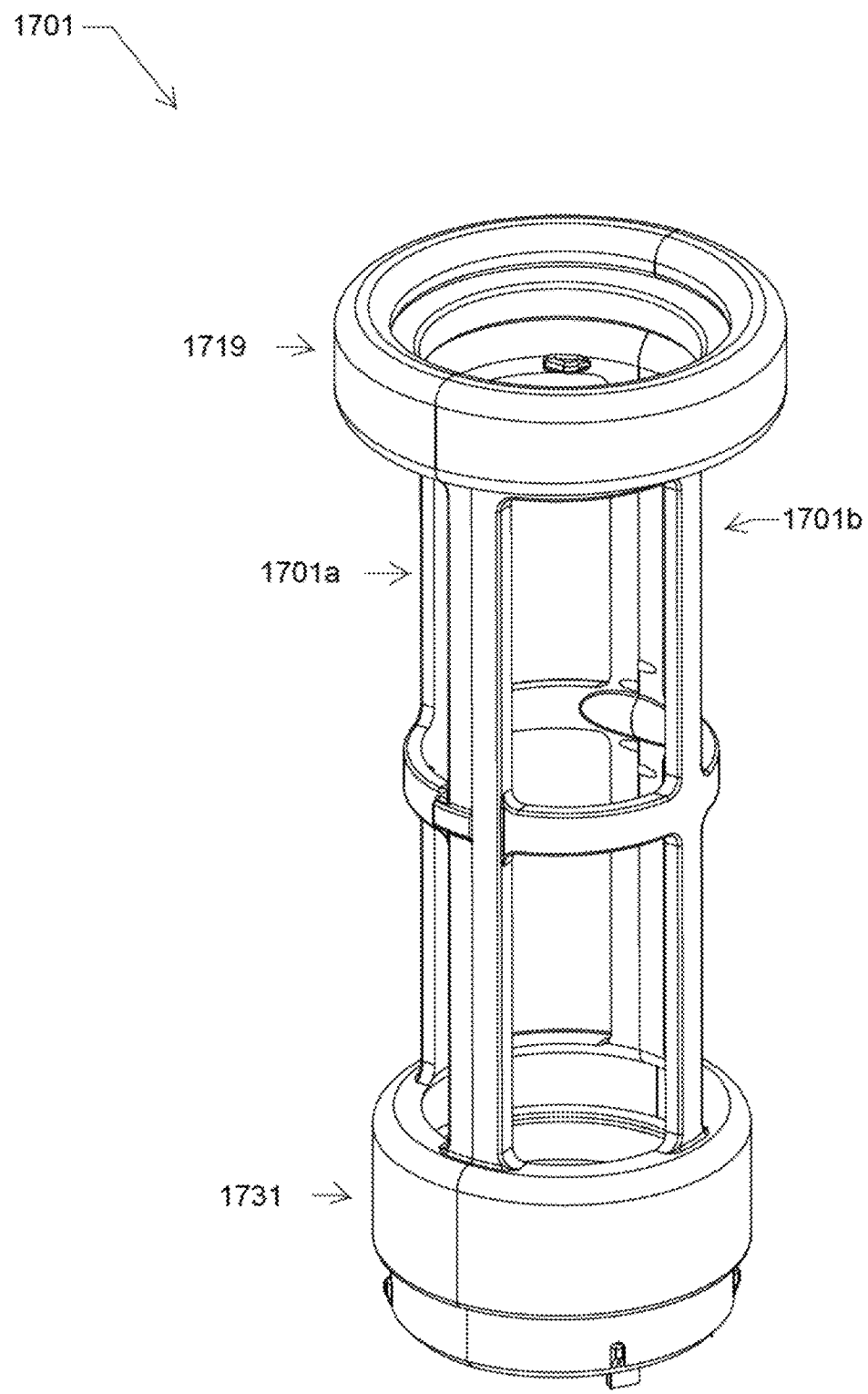
FIG. 46 is a perspective view of the frame forming a part of the low-level water float of FIGS. 42-45.
Figure 47:
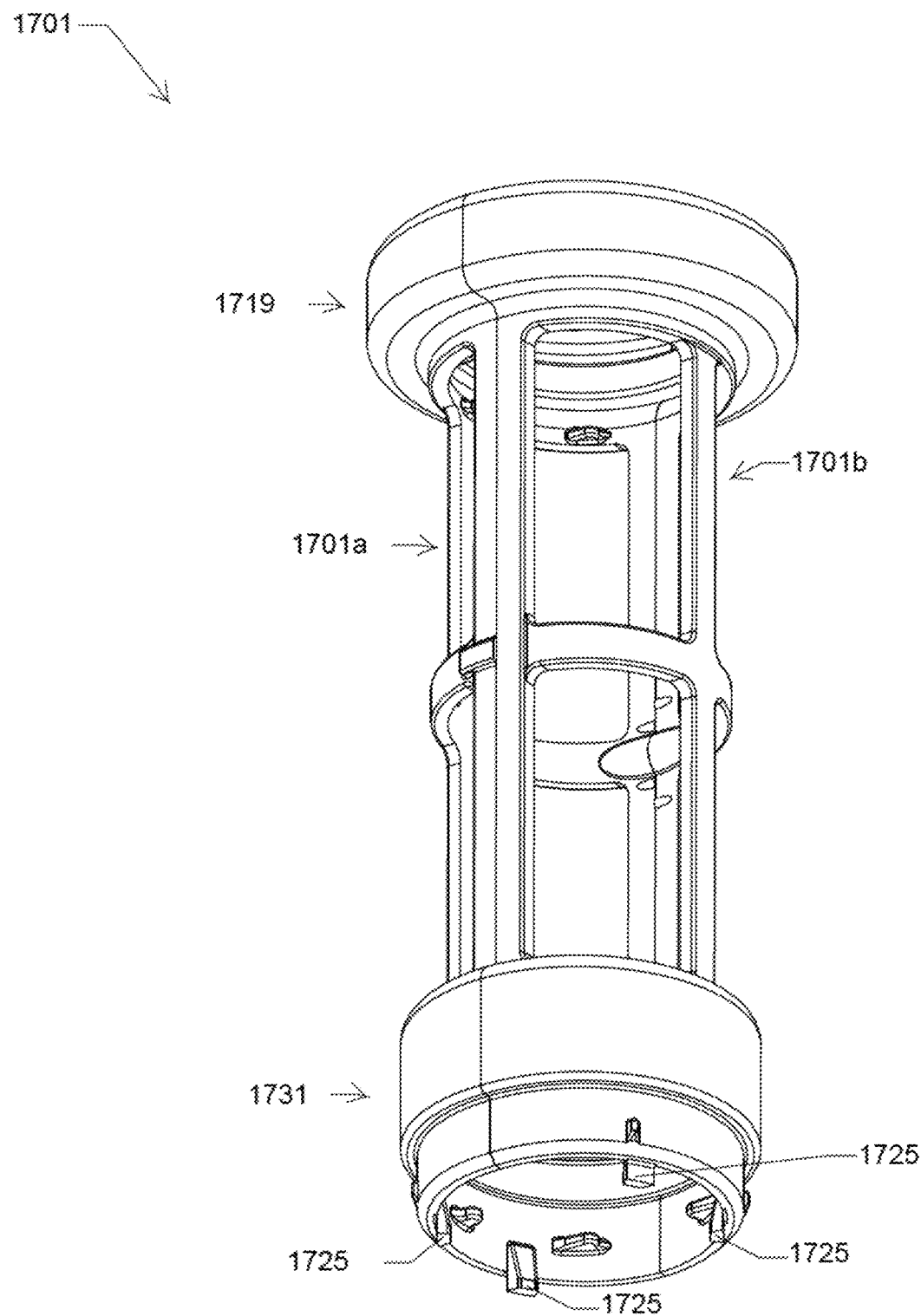
FIG. 47 is another perspective view of the frame forming a part of the low-level water float of FIGS. 42-45.
Figure 48:
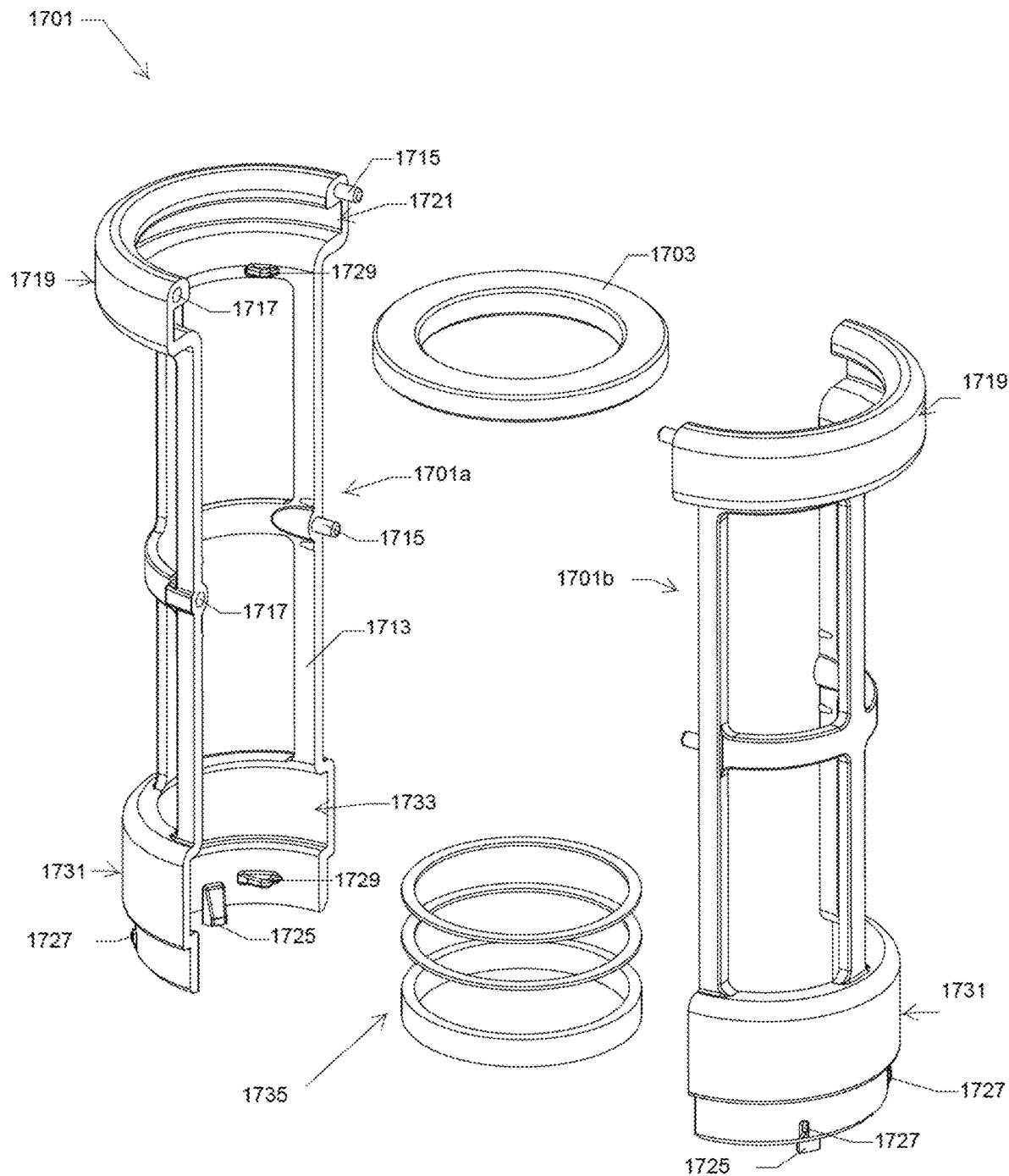
FIG. 48 is a perspective, exploded view of the frame of FIGS. 46 and 47.
Figure 49:
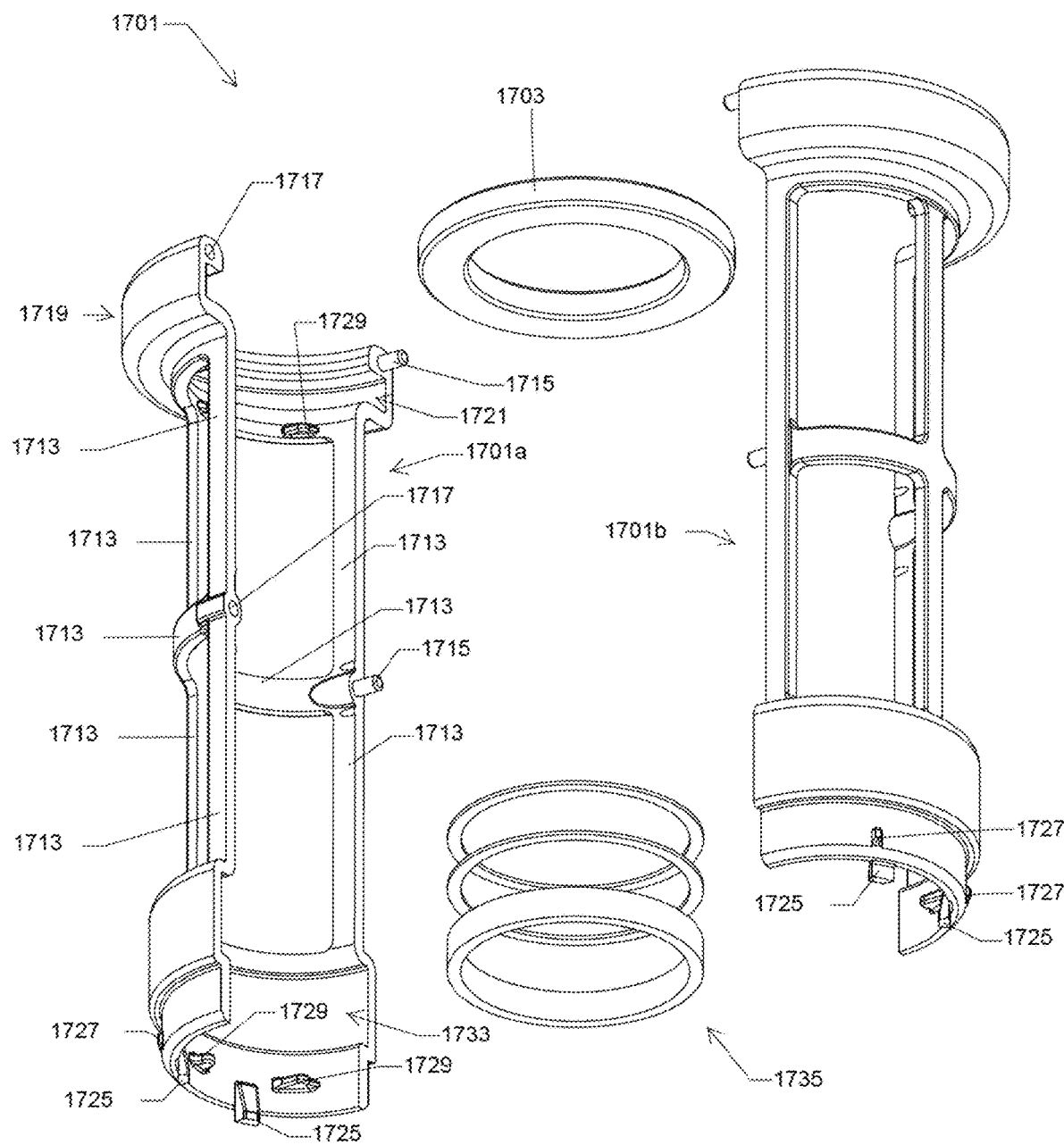
FIG. 49 is another perspective, exploded view of the frame of FIGS. 46 and 47.
Figure 50:
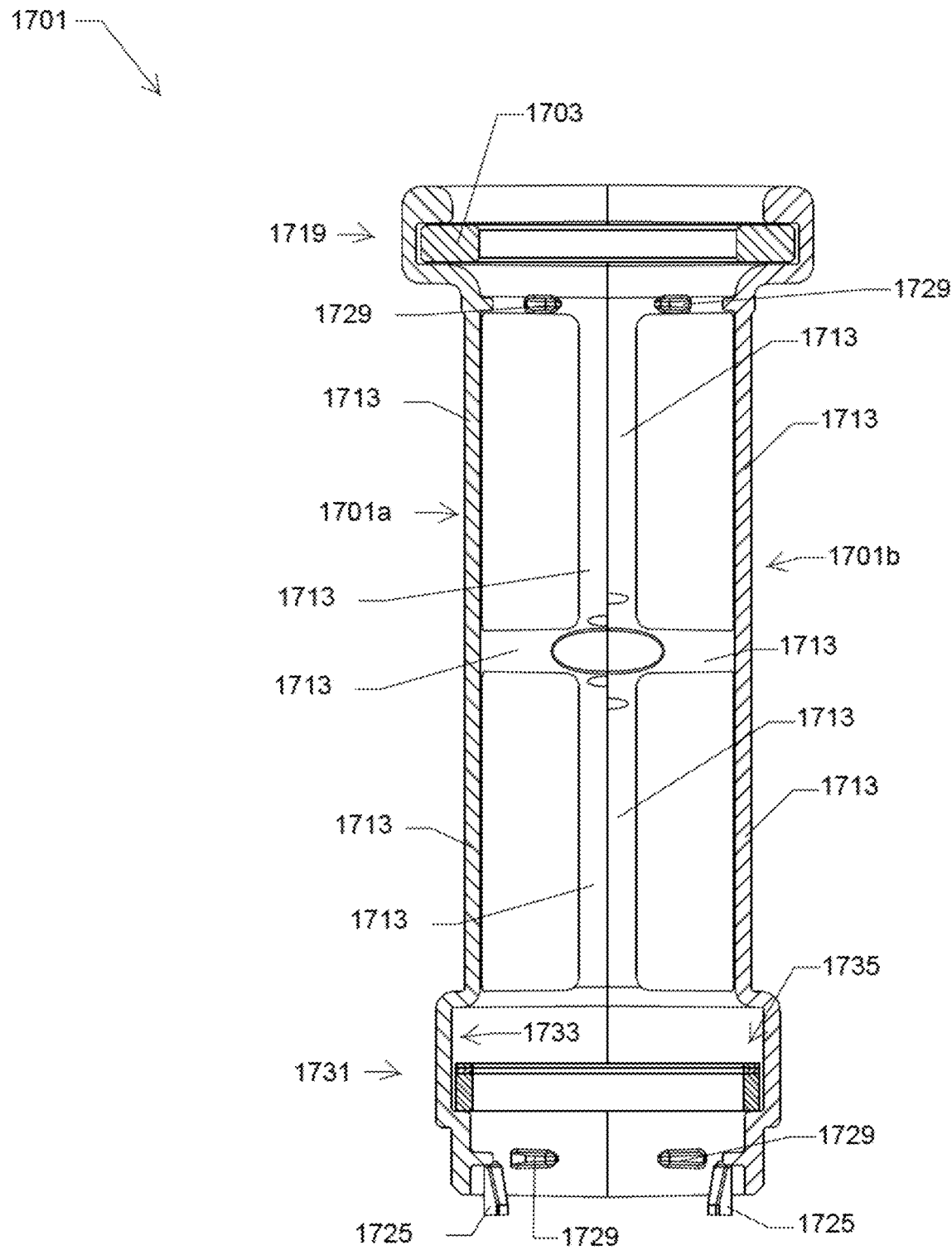
FIG. 50 is a sectional view of the frame of FIGS. 46-49.
Figure 51:
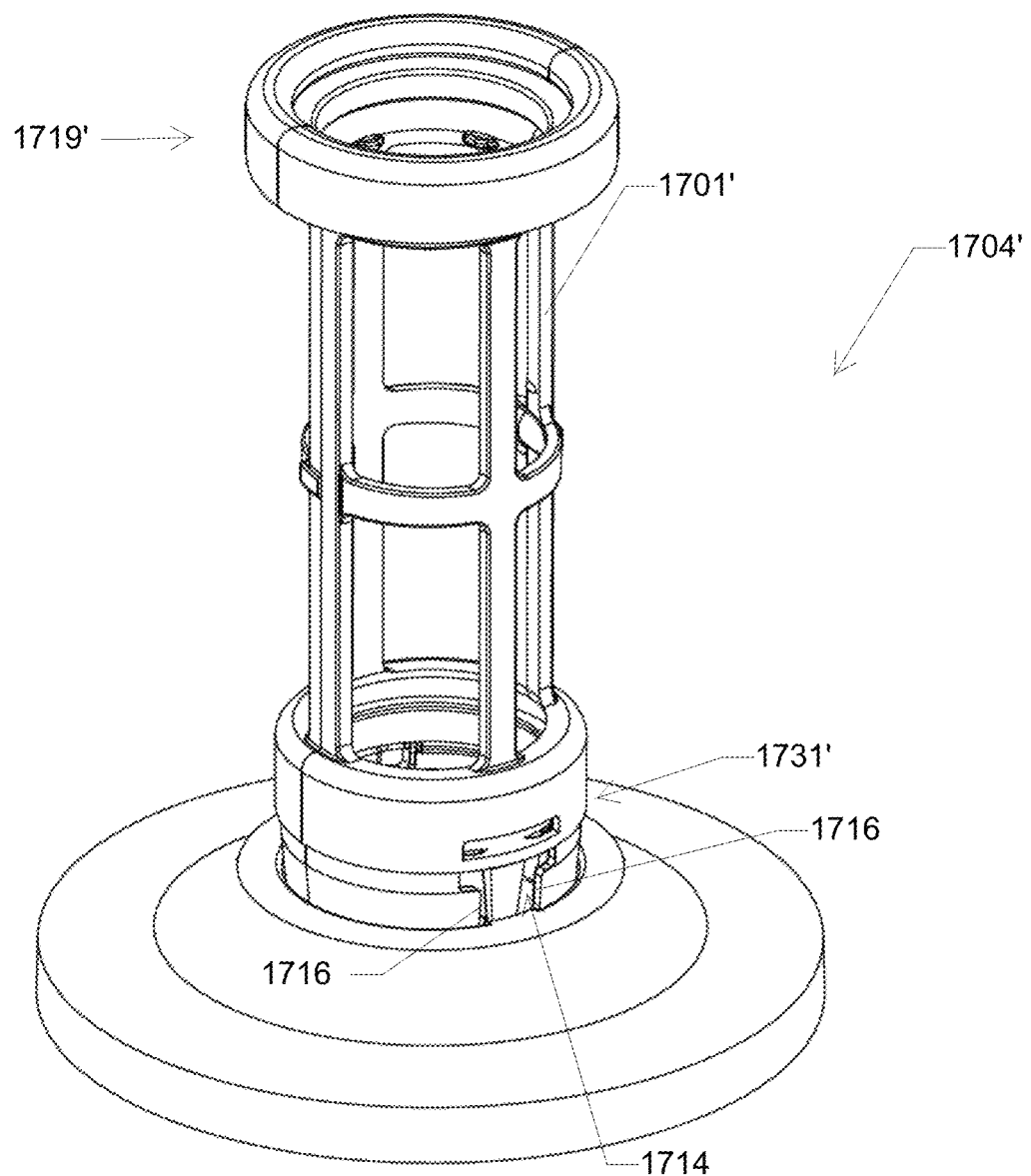
FIG. 51 is a perspective view of an alternative embodiment water float of the present disclosure.
Figure 52:
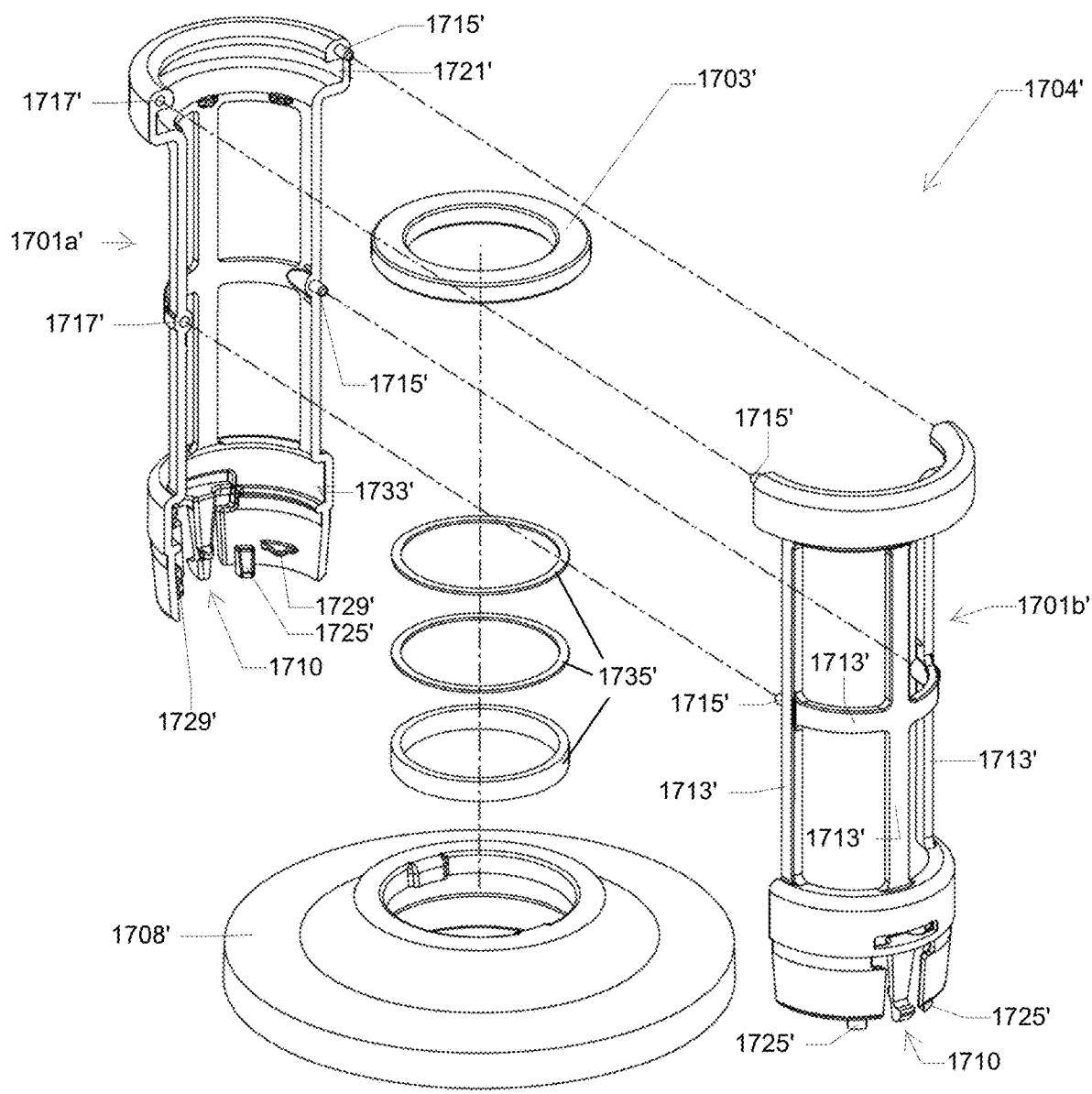
FIG. 52 is an exploded view of the water float of FIG. 51.

FIG. 44B shows float base 1708 positioned atop floor 1707 of UST 16. The position of FIG. 44B would be achieved if UST 16 did not contain enough water to buoy water float 1704 from its fully lowered position atop floor 1707 of UST 16. Fuel float 1709 is shown in FIG. 44B resting atop frame 1701 of water float 1704. This position of fuel float 1709 would be achieved if UST 16 did not contain enough fuel to buoy fuel float 1709 from its fully lowered position atop water float 1704. In the position of fuel float 1709 and water float 1704 illustrated in FIG. 44B, fuel float magnet 1711 is distanced from water float magnet 1703 about 3.0 inches to ensure the height of both water float 1704 and fuel float 1709 can be read and communicated by mangetostrictive probe shaft 1712. Water float 1704' is exchangeable with water float 1704 shown in FIG. 44B, as described above.

Both fuel float 1709 and water float 1704, 1704' have features to facilitate ease in movement away from the positions illustrated in FIG. 44B. Particularly, both fuel float 1709 and water float 1704, 1704' include features that create minimal contact area between the floats and the support surfaces below. Referring to FIG. 44B, fuel float 1709 features fuel float feet 1723 extending downwardly therefrom. Fuel float feet 1723 are evenly spaced about longitudinal axis L1 of magnetostrictive probe shaft 1712. In one exemplary embodiment, fuel float feet 1723 are spaced at 120 degree intervals about axis L1. Each fuel float foot 1723 creates nominal point contact with the surface below, which, in the embodiment of FIG. 44B is frame 1701 of water float 1704, but which could also be frame 1701' of water float 1704'.

Water float 1704, 1704' similarly features water float feet 1725, 1725' as illustrated in FIGS. 45-50 and 51-55. Frame 1701 of water float 1704 is secured to float base 1708 by positioning the distal end of frame 1701 into the central aperture through float base 1708 such that friction connectors 1727 of frame 1701 frictionally engage the wall forming the central aperture through water float 1704. In certain embodiments, an adhesive can also be positioned at the juncture of frame 1701 and float base 1708.

Figure 53:
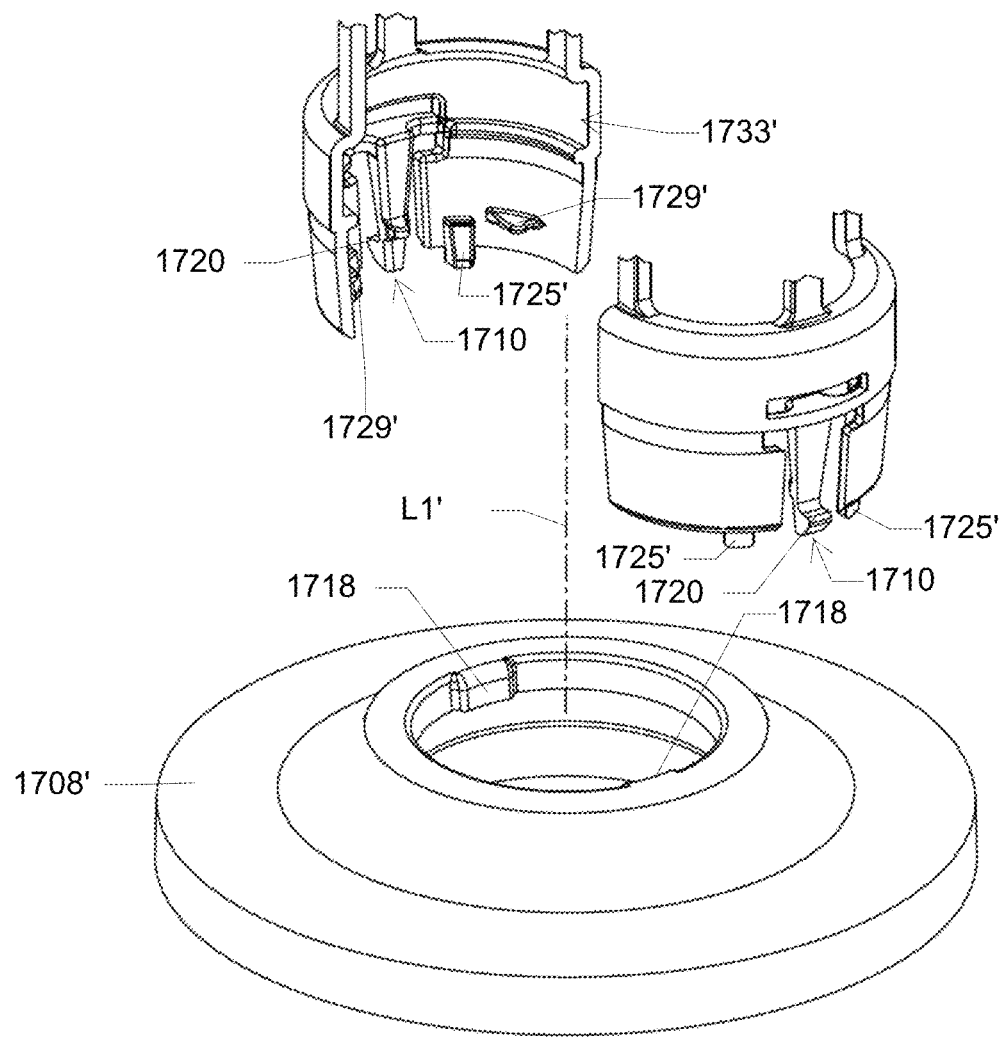
FIG. 53 is a partial, exploded view of the water float of FIG. 51.
Figure 54:
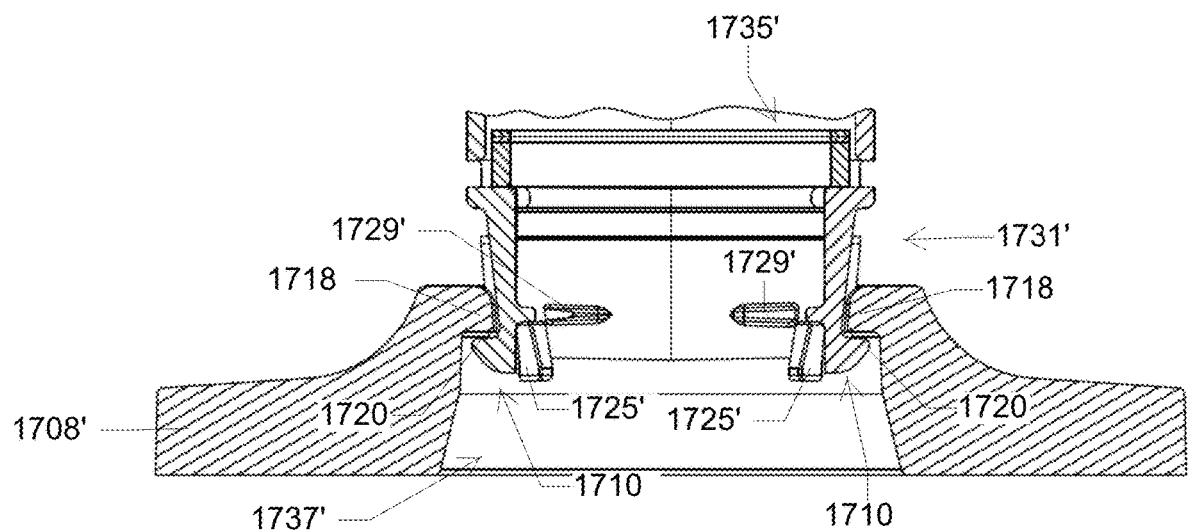
FIG. 54 is a partial, sectional view of the float of FIG. 51.
Figure 55:
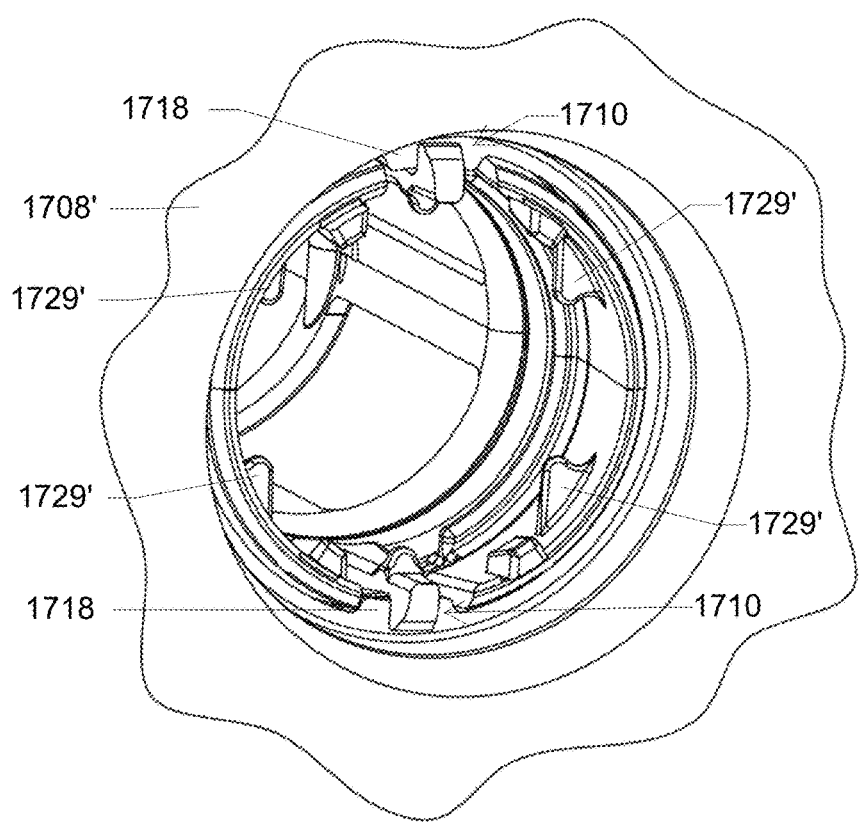
FIG. 55 is a partial perspective view of the float of FIG. 51.

In the embodiment of water float 1704' illustrated in FIGS. 51-55, frame 1701' features snap connectors 1710 to secure frame 1701' to float base 1708'. Each frame half 1701a', 1701b' includes a snap connector 1710, as illustrated, e.g., in FIG. 52. Each snap connector 1710 is cantilevered from the frame half 1701a', 1701b' from which it extends. Each frame half 1701a', 1701b' includes channel 1714 (FIG. 51) in which a snap connector 710 is positioned. Sidewalls 1716 define channel 1714 and provide for indexing assembled frame 1701' to float base 1708'. Referring to FIG. 53, float base 1708' includes two stops 1718 extending radially inwardly into the central aperture through float base 1708'. Stops 1718 fit within channels 1714 (see FIG. 51), with sidewalls 1716 flanking stop 1718 and defining the positioning of frame 1701' relative to float base 1708'. To connect frame 1701' to float base 1708', each stop 1718 is positioned between sidewalls 1716 defining a channel 1714 and the ramped distal end of each snap connector 1710 contacts the ramped proximal end of each stop 1718. Application of further force bringing frame 1701' and float base 1708' together along longitudinal axis L1' (FIG. 53) causes each snap connector 1710 to elastically flex radially inwardly toward longitudinal axis L1' and ride over stop 1718, until shoulder 1720 passes stop 1718 and each snap connector 1710 moves to a lower energy position, i.e., a position that is less elastically flexed radially inwardly (e.g., a position in which each snap connector is not flexed). In this position, shoulder 1720 engages stop 1718 to block withdrawal of frame 1701' from float base 1708' along longitudinal axis L1'. As shown in FIG. 54, each snap connector 1710 tapers radially outwardly from shoulder 1720 to the opposing end of snap connector 1710. This taper resists movement of float base 1708' upwardly (in the view of FIG. 54) relative to frame 1701'.

With frame 1701, 1701' secured to float base 1708, 1708', water float feet 1725, 1725' extend distally (along longitudinal axis L1, L1') from float base 1708, 1708' and each nominally present point contact with foot 1706. Foot 1706 can be positioned atop floor 1707 of UST 16 as illustrated, e.g., in FIG. 44A. In this position, foot 1706 serves as a datum for the probe. With foot 1706 positioned atop floor 1707 of UST 16, water float feet 1725, 1725' will contact foot 1706 just before water float 1704, 1704' can touch floor 1707. In the embodiment illustrated, frame 1701, 1701' includes four water float feet 1725, 1725'.

Frame 1701, 1701' also includes frame spacers 1729, 1729' extending radially inward therefrom. Frame spacers 1729, 1729' nominally present point contact with magnetostrictive probe shaft 1712 to decrease friction between frame 1701, 1701' and magnetostrictive probe shaft 1712. With each frame half 1701a, 1701b or 1701a', 1701b' presenting four frame spacers 1729, 1729', frame 1701, 1701' nominally contacts magnetostrictive probe shaft 1712 at four points during reciprocation along its travel.

Fuel float 1709 is designed to be buoyant in fuel, such as diesel fuel having a specific gravity of about 0.8 to 0.9. Water float 1704, 1704' is designed to be buoyant in water, which has a specific gravity of 1.0, by definition. More specifically, the density of water float 1704 is such that is will sink in diesel fuel (and, of course, lower specific gravity motor fuel products such as gasoline), but will be buoyant in a low level of water, e.g., no more than 0.25 inches of water and, more particularly, in as little as 0.060 inches of water collected at the bottom of UST 16. In exemplary embodiments, UST 16 is a cylindrical tank, as illustrated in FIG. 1, with a diameter of 6.5 feet or 8 feet on the low end. In the case of a cylindrical tank of radius 6.5 feet, a 2.75-inch diameter float can be nominally spaced no more than 0.03 inches from floor 1707 of UST 16. In the case of a cylindrical tank of radius 8.0 feet, a 2.75-inch diameter float can be nominally spaced no more than 0.01 inches from floor 1707 of UST 16. In certain embodiments, foot 1706 extends 0.032 inches from the bottom of water float 1704, 1704' in the lowest position of water float 1704, 1704'. In such embodiments, this 0.032 inches gap sets the minimum distance of water float 1704, 1704' from the bottom of UST 16.

To space water float magnet 1703, 1703' about 3.0 inches from the datum magnet at distal end 1705 of mangetostrictive probe shaft 1712 and maintain the density necessary to be buoyant on no more than 0.25 inches of water, frame 1701, 1701' is constructed of a low density material. In one exemplary embodiment, frame 1701 is constructed of Zytel HTN51G35HSL BK083 available from Dupont and described in detail on the spec sheet filed in an IDS on even date herewith, the entire contents of which are hereby expressly incorporated by reference herein. As illustrated in the FIGS. 42-50 and 51-55, frame 1701, 1701' is formed by a plurality of slender frame segments 1713, 1713' surrounding open spaces significantly larger than the frame segments 1713, 1713'.

In an exemplification of the present disclosure, frame 1701, 1701' has a total height of about 3.2 inches, with top end 1719, 1719' and bottom end 1731, 1731' each being about 0.32 inches and 0.44 inches high, respectively, with frame segments 1713, 1713' spanning top end 1719, 1719' and bottom end 1731, 1731' and having a length of about 2.4 inches. Frame segments 1713, 1713' extend about longitudinal axis L1, L1' to a diameter of about 0.92 inches or about 1 inch. This diameter defines the lateral maximum extent of frame 1701, 1701'.

Frame 1701, 1701' comprises two nominally identical frame halves 1701a, 1701b or 1701a', 1701b'. Each frame half 1701a, 1701b or 1701a', 1701b' includes a central vertical frame segment 1713, 1713' having a width of about 0.115 inches and a depth of about 0.1 inches. Each frame half 1701a, 1701b or 1701a', 1701b' also includes and a central horizontal frame segment 1713, 1713' having a height of about 0.125 inches and a depth of about 0.1 inches. Each frame half 1701a, 1701b or 1701a', 1701b' also includes a pair of vertical segments 1713, 1713', each accommodating one of attachment aperture 1717, 1717' (described in more detail below) or attachment boss 1715, 1715' (described in more detail below). The vertical segments 1713, 1713', each have a width of about 0.09 inches and a depth of about 0.1 inches.

Each frame half 1701a, 1701b or 1701a', 1701b' includes a pair of attachment bosses 1715, 1715' and corresponding attachment apertures 1717, 1717'. The attachment bosses 1715, 1715' of frame half 1701a, 1701a' are positioned to be received in the attachment apertures 1717, 1717' of frame half 1701b, 1701b', while the attachment bosses 1715, 1715' of frame half 1701b, 1701b' are simultaneously received in the attachments apertures 1717, 1717' of frame half 1701a, 1701a'. In one exemplary embodiment, attachment bosses 1715, 1715' form an interference fit with the walls forming attachment apertures 1717, 1717'.

Top end 1719 of each frame half 1701a, 1701b or 1701a', 1701b' includes magnet carrier 1721, 1721' comprising an annular channel sized to receive water float magnet 1703, 1703'. Water float magnet 1703, 1703' is an annular ring having an inner diameter sized larger than the outer diameter of magnetostrictive probe shaft 1712. The outer diameter of water float magnet 1703, 1703' is sized nominally congruent to the annular channel formed by magnet carriers 1721, 1721' of frame halves 1701a, 1701b or 1701a', 1701b'. Frame halves 1701a, 1701b or 1701a', 1701b' are assembled one to the other as described above, with water float magnet 1703, 1703' positioned to be received by magnet carriers 1721, 1721'. When frame halves 1701a, 1701b or 1701a', 1701b' are assembled as illustrated, e.g., in FIGS. 46 and 47 or FIG. 51, water float magnet 1703, 1703' is frictionally held by magnet carriers 1721, 1721' such that axial movement of water float magnet 1703, 1703' relative to frame 1701, 1701' is prohibited.

Bottom end 1731, 1731' of each frame half 1701a, 701b or 1701a', 1701b' includes ballast receiver 1733, 1733' sized to receive one or more of ballast rings 1735. Ballast receivers 1733, 1733' cooperate to define an annular groove when frame halves 1701a, 1701b or 1701a', 1701b' are joined together to form frame 1701, 1701'. "Ballast receiver" is used herein to described the combined structure formed by the cooperation of both ballast receivers 1733, 1733' identified in the illustrations. Ballast receiver 1733, 1733' defines an inner diameter sized to accommodate one or more ballast rings 1735, 1735'. The outer diameter of each ballast ring 1735, 1735' is nominally congruent to the inner diameter of ballast receiver 1733, 1733', but just undersized enough to allow for easy insertion of ballast rings 1735, 1735' into ballast receiver 1733, 1733' in a radial direction. The inner diameters of ballast rings 1735, 1735' are nominally equal in size, but each ballast ring may have a different height to impart a different mass of ballast.

Ballast receiver 1733, 1733' also defines a height along longitudinal axis L1, L1'. The height of ballast receiver 1733, 1733' is sufficient to accommodate a plurality of ballast rings 1735, 1735'. Because the specific gravity of certain motor fuels, e.g., light diesel, is close to 1.0 (the specific gravity of water), water float 1704 must have a very precise density to sink in the motor fuel above and be buoyant on the water below. Common manufacturing practices make this tightrope even more difficult to walk.

To ensure that water float 1704, 1704' is sufficiently dense to sink in the motor fuel contained in UST 16, one or more ballast rings 1735, 1735' can be added to frame 1701, 1701'. The chosen ballast rings are inserted into a ballast receiver on one of frame halves 1701a, 1701b or 1701a', 1701b' prior to joining the frame halves to form frame 1701, 1701'. Because ballast rings 1735, 1735' have an outer diameter complementary to the inner diameter of ballast receiver 1733, 1733', i.e., nominally substantially congruent—that is, of congruent shape, but with the outer diameter of ballast rings 1735, 1735' undersized enough to allow for radial (orthogonal to longitudinal axis L1) insertion of ballast rings 1735, 1735' into ballast receiver 1733, 1733' and nominally the same inner diameter, only the necessary cumulative height of ballast rings 1735, 1735' needs to be determined. The needed height of ballast rings 1735, 1735' can be determined through trial and error. Alternatively, the needed height of ballast rings 1735, 1735' can be calculated. After the required ballast height is determined, a plurality of ballast rings having a total height substantially equal (i.e., as close as the available ballast ring sizes will allow) to the determined ballast height can be chosen. An exemplary computation of the needed ballast ring height is shown below.

List of Variables:
$V_f$=Volume of Float
$V_I$=Volume of Frame
$V_M$=Volume of Magnet
$P_D$=Density of Diesel
$P_f$=Density of Float
$P_I$=Density of Frame
$V_M$=Density of Magnet
$F_{B\ Diesel}$=Buoyant force from Diesel
$M_f$=Mass of Float
$M_I$=Volume of Frame
$M_M$=Mass of Magnet
$V_{Ball}$=Volume of Ballast
$P_{Ball}$=Density of Ballast
$F_{Ball\ Diesel}$=Buoyant force from Diesel
$A_{Ball\ CS}$=Cross Section Area of Ballast
$H_{Ball}$=Height of Ballast The below table shows the specific gravity ranges that each part will have. The specific gravity of water is 1. All references to "density" in these calculations are in units of specific gravity.

|  | volume (cm3) | | | Density (g/cm3) | |
| --- | --- | --- | --- | --- | --- |
|  | max | min | range | max | min |
| stem | 6.631943 | 4.991467 | 1.640476 | 1.48 | 1.46 |
| diesel |  |  |  | 0.90 | 0.80 |
| magnet | 1.237482 | 0.87249 | 0.364992 | 4.96 | 4.56 |
| float | 24.66302 | 21.20109 | 3.461931 | 0.495 | 0.465 |

Calculations below are what we will use to calculate the "height" of ballast needed for each float.

Float assembly without ballast buoyancy in diesel. (Float, Frame #=*2, Magnet)

Float assembly without ballast buoyancy in diesel. (Float, Frame #=*2, Magnet)

$$\underbrace{(V_F + V_I + V_M)P_D}_{\text{Buoyancy from Diesel}} - \underbrace{(P_F V_F + P_I V_I + P_M V_M)}_{\text{Mass of Components}} =$$

$F_{BDiesel}$ Gravity disregarded $$(P_D - P_F)V_F + (P_D - P_I)V_I + (P_D - P_M)V_M = F_{BDiesel}$$

$$\frac{(P_D - P_F)*M_F}{P_F} + \frac{(P_D - P_I)*M_I}{P_I} + \frac{(P_D - P_M)*M_M}{P_M} = F_{BDiesel}$$

$$\left(\frac{P_D}{P_F} - 1\right)M_F + \left(\frac{P_D}{P_I} - 1\right)M_I + \left(\frac{P_D}{P_M} - 1\right)M_M = F_{BDiesel}$$

(−) Ballast buoyancy in diesel must be equal to or greater than the float assembly buoyancy above.

$$F_{BDiesel} = -F_{BallDiesel} = -V_{Ball}(P_D - P_{Ball})$$

$$F_{BDiesel} = V_{Ball}(P_{Ball} - P_D)$$

$$\frac{F_{BDiesel}}{(P_{Ball} - P_D)} = V_{Ball} = A_{BallCS} * H_{Ball}$$

$$\frac{H_{Ball}}{(cm)} = \frac{\left(\frac{F_{BDiesel}}{(P_{Ball} - P_D)}\right)}{A_{BallCS}} = \frac{F_{BDiesel}}{(P_{Ball} - P_D) * A_{BallCS}}$$

$$\frac{H_{Ball}}{(in)} = \frac{F_{BDiesel}}{(P_{Ball} - P_D) * A_{BallCS}} * 2.54$$

After determining the necessary ballast rings 1735, 1735' and assembling frame halves 1701a, 1701b or 1701a', 1701b', with water float magnet 1703, 1703' and ballast rings 1735, 1735' secured in magnet carrier 1721, 1721' and ballast receiver 1733, 1733', respectively, frame 1701, 1701' is secured to float base 1708, 1708' as described above. Water float 1704, 1704' can then receive magnetostrictive probe shaft 1712 through its central opening (and the central openings of magnet 1703, 1703' and ballast rings 1735, 1735') so that frame spacers 1729, 1729' contact magnetostrictive probe shaft 1712 through the travel of water float 1704, 1704' along magnetostrictive probe shaft 712. With fuel float 1709 and water float 1704, 1704' positioned about magnetostricitve probe shaft 1712, foot 1706 can be secured to the distal end of magnetostrictive probe shaft 1712 with a snap ring.

When the probe is fully assembled, foot 1706 is positionable within foot recess 1737, 1737' of float base 1708, 1708' such that float base 1708, 1708' can be positioned very close to floor 1707 of UST 16. In certain embodiments, float base 1708, 1708' is spaced 0.0060 inches or less from floor 1707 of UST 16. Foot recess 1737, 1737' has an inner diameter larger than the outer diameter of foot 1706.

In use, probe shaft 1712 is communicatively connected to controller 102 or an indicator to relay a water measurement and/or alarm to a user. A threshold measured water level may signal actuation of filtration systems 200, 200', 200A, or 200B. A threshold measured water level may also signal corrosion mitigation in the form of water removal from storage tank 16 by direct pumping from the floor of storage tank 16 or other mechanisms.

Figure 38A:
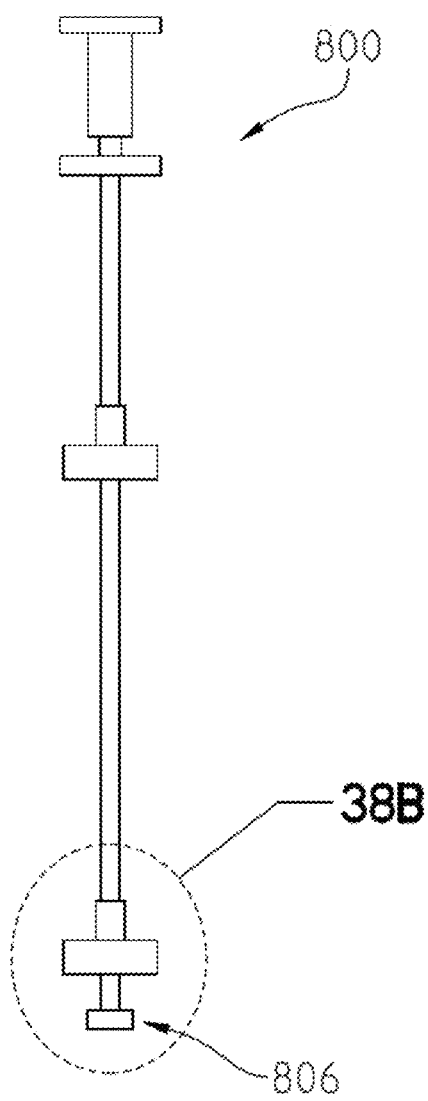
FIG. 38 includes a radial elevational view (FIG. 38A) of a probe including a water sensor in accordance with an alternative embodiment of the present disclosure and an enlarged partial sectional view (FIG. 38B) of the probe foot of the probe of FIG. 38A.
Figure 38B:
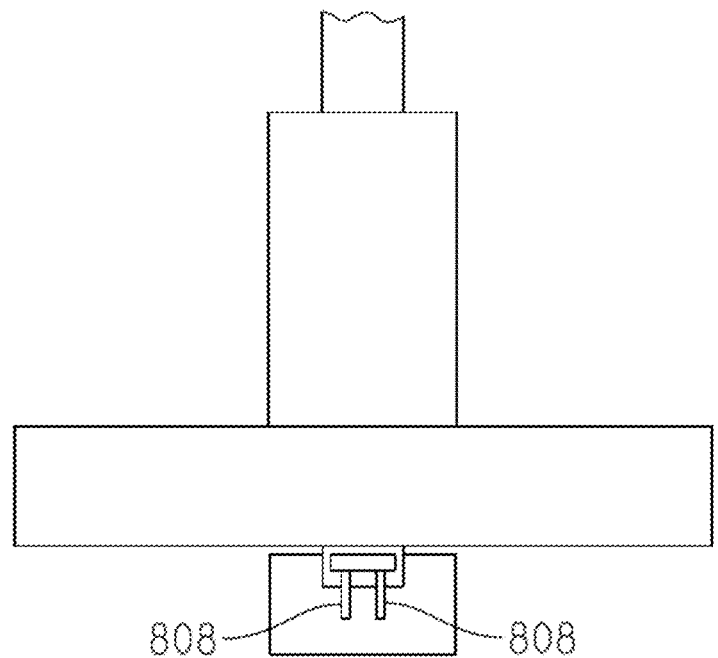
Figure 39:
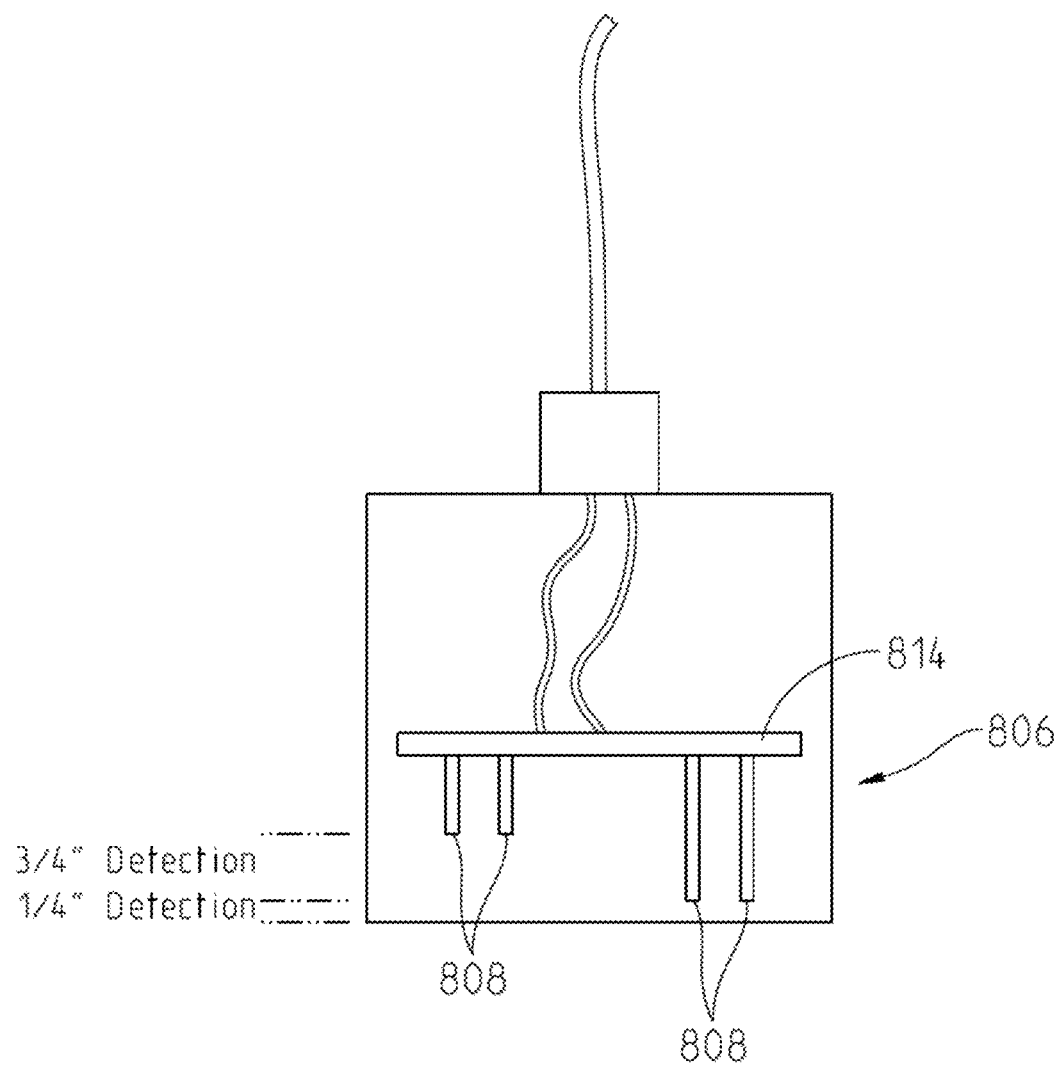
FIG. 39 is a schematic view of a water sensor useable with the probe of FIG. 38.

FIGS. 38 and 39 illustrate exemplary water sensor 800. Water sensor 800 is communicatively connected to controller 102 or an indicator to relay a water measurement and/or alarm to a user. A threshold measured water level may signal actuation of filtration systems 200, 200', 200A, or 200B. A threshold measured water level may also signal corrosion mitigation in the form of water removal from storage tank 16 by direct pumping from the floor of storage tank 16 or other mechanisms.

Water sensor 800 may include standard water and fuel product floats as shown in FIG. 38A (which, in use, would be positioned as illustrated in FIG. 1 with respect to sensor 700) together with low level water sensor 804. Water sensor 804 includes foot 806 for placement atop the floor of storage tank 16. Within foot 806 are conductivity pins 808 arranged in pairs. An operative pair of conductivity pins 808 terminate at the same height from distal end 810 of foot 806 which, in use, will establish a datum coincident with the floor of storage tank 16. A current is able to be conducted between an operative pair of conductivity pins 808 when the conductivity pins are immersed at their distal ends in a conductive fluid such as water. The current is not able to be conducted between the operative pair of conductivity pins 808 when the conductivity pins are immersed at their distal ends in a insulative fluid such as oil (i.e., motor fuel, such as gasoline and diesel, as previously defined herein). Conductivity pins 808 are operatively connected to PCB 814 to communicate conductivity as a measure of water through probe shaft 812. Referring to FIG. 39, a first pair of conductivity pins 808 are spaced ¼ inch above distal end 810 of foot 806. If a current is conducted between these conductivity pins 808, then PCB 814 can signal controller 102 or an indicator that storage tank 16 contains ¼ inch of water. A second pair of conductivity pins 808 are spaced ⅞ inch above distal end 810 of foot 806. If a current is conducted between these conductivity pins 808, then PCB 814 can signal controller 102 or an indicator that storage tank 16 contains ⅞ inch of water. Operative pairs of conductivity pins can be spaced above distal end 80 of foot 806 15/16 inch, ⅞ inch, 13/16 inch, ⅞ inch, 11/16 inch, ⅝ inch, 9/16 inch, ½ inch, 7/16 inch, ⅜ inch, 5/16 inch, ¼ inch, 3/16 inch, ⅛, or 1/16 to enable sensing or corresponding levels of water above the floor of storage tank 16.

Figure 40A:
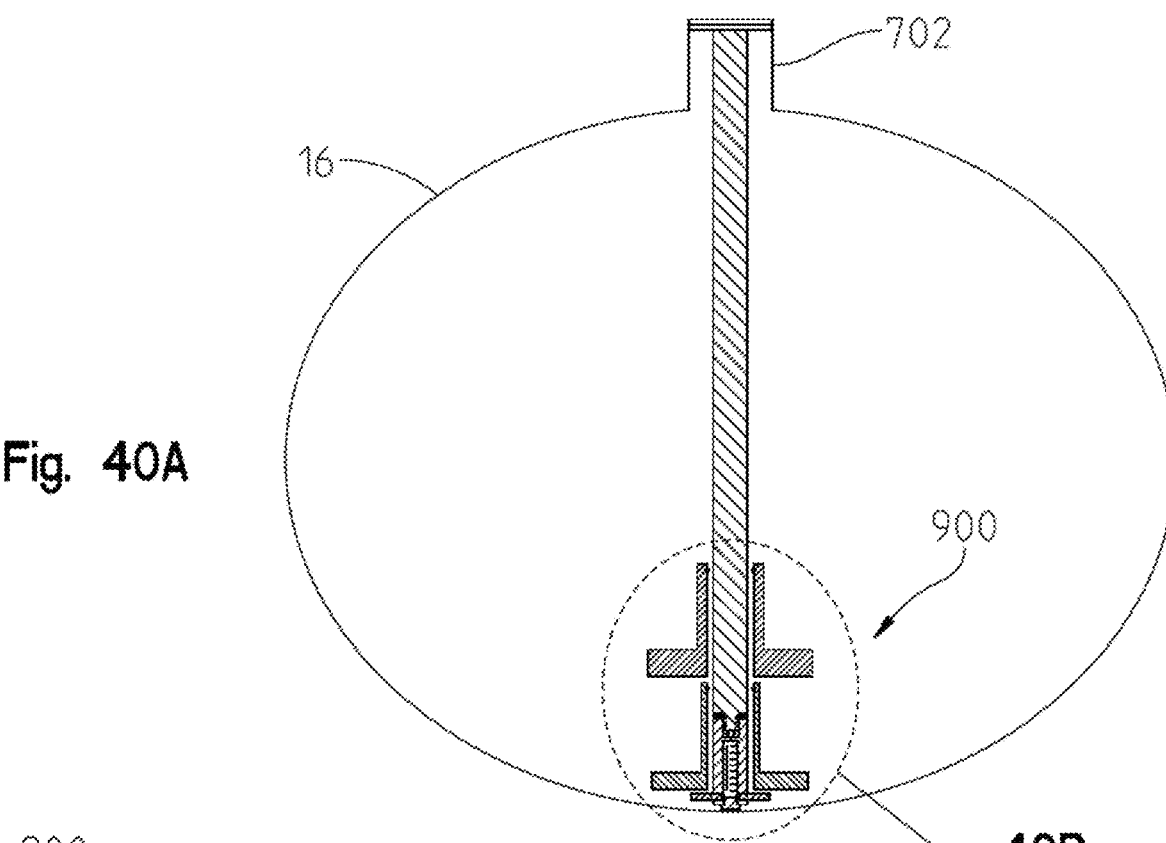
FIG. 40A is a schematic view of an alternative water sensor arrangement.
Figure 40B:
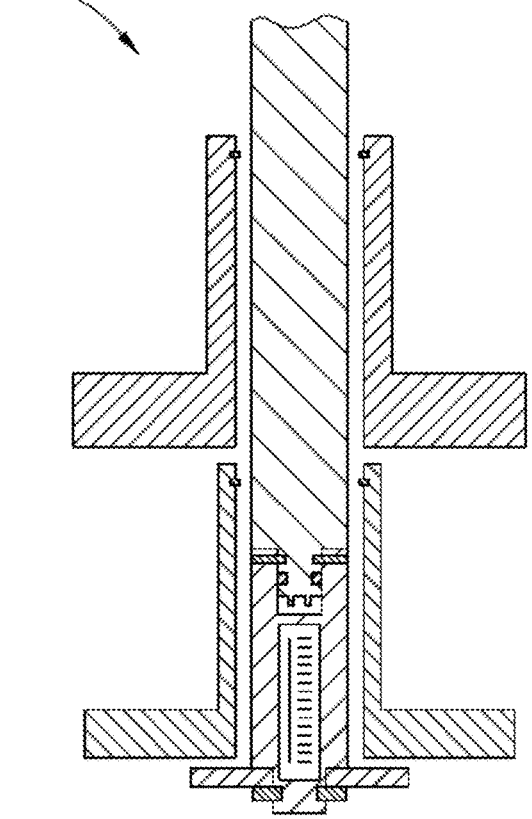
FIG. 40B is an enlarged partial view of the arrangement of FIG. 40A.
Figure 41:
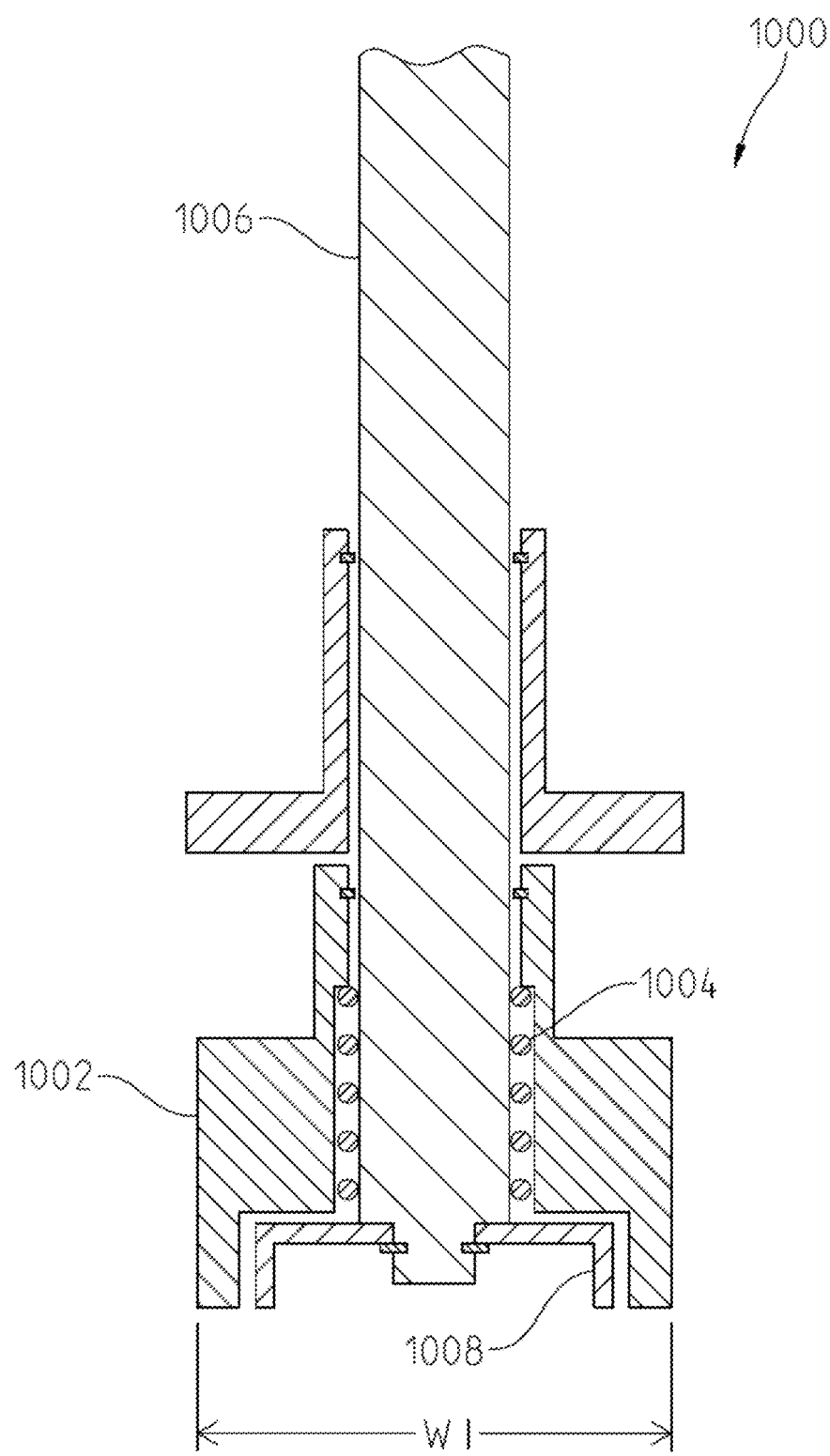
FIG. 41 is schematic view of another alternative water sensor arrangement.
Figure 42:
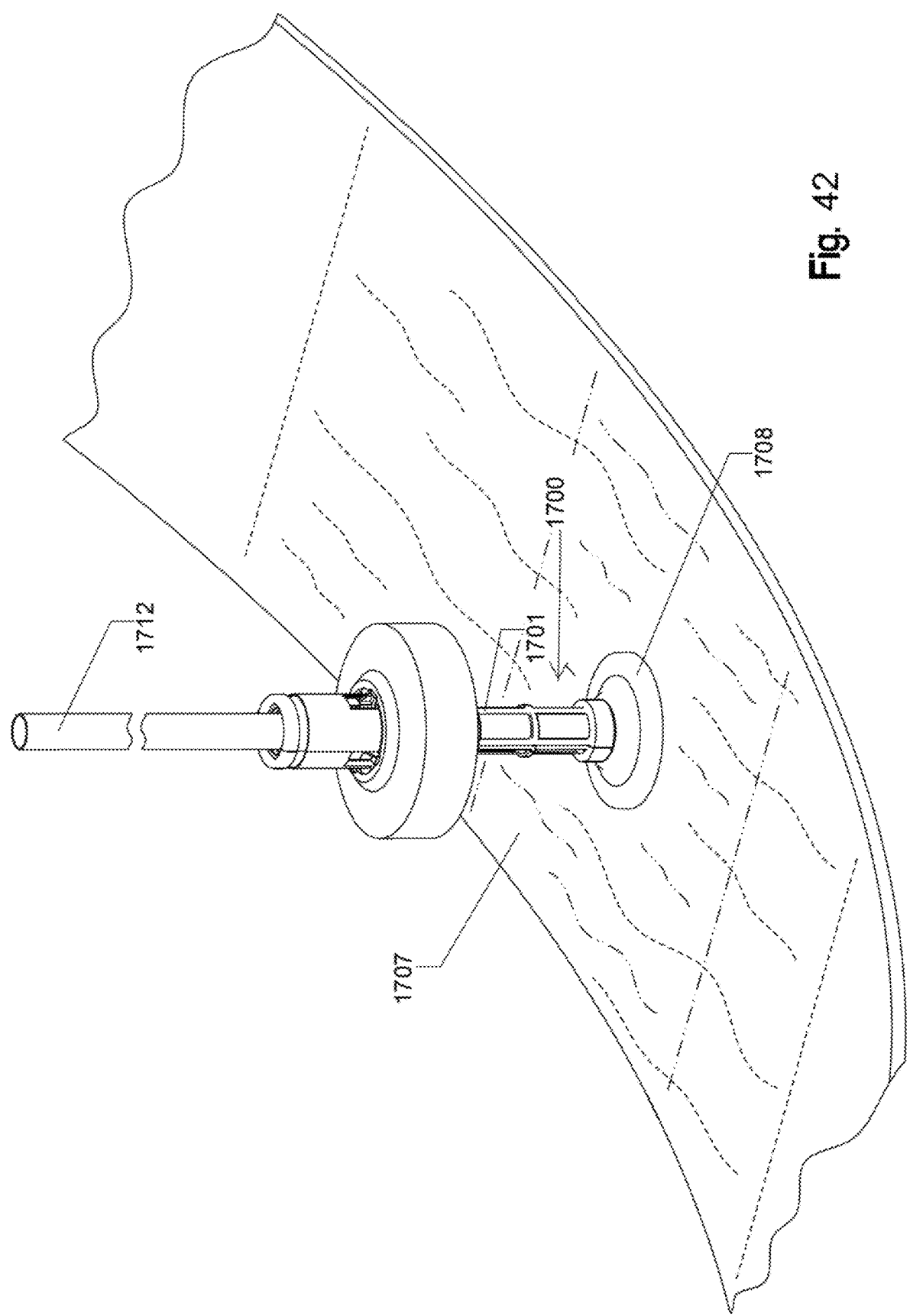
FIG. 42 is a partial perspective view of a portion of underground storage tank ("UST") 16 shown in FIG. 1 together with a tank probe featuring a low-level water sensor of the present disclosure.
Figure 43:
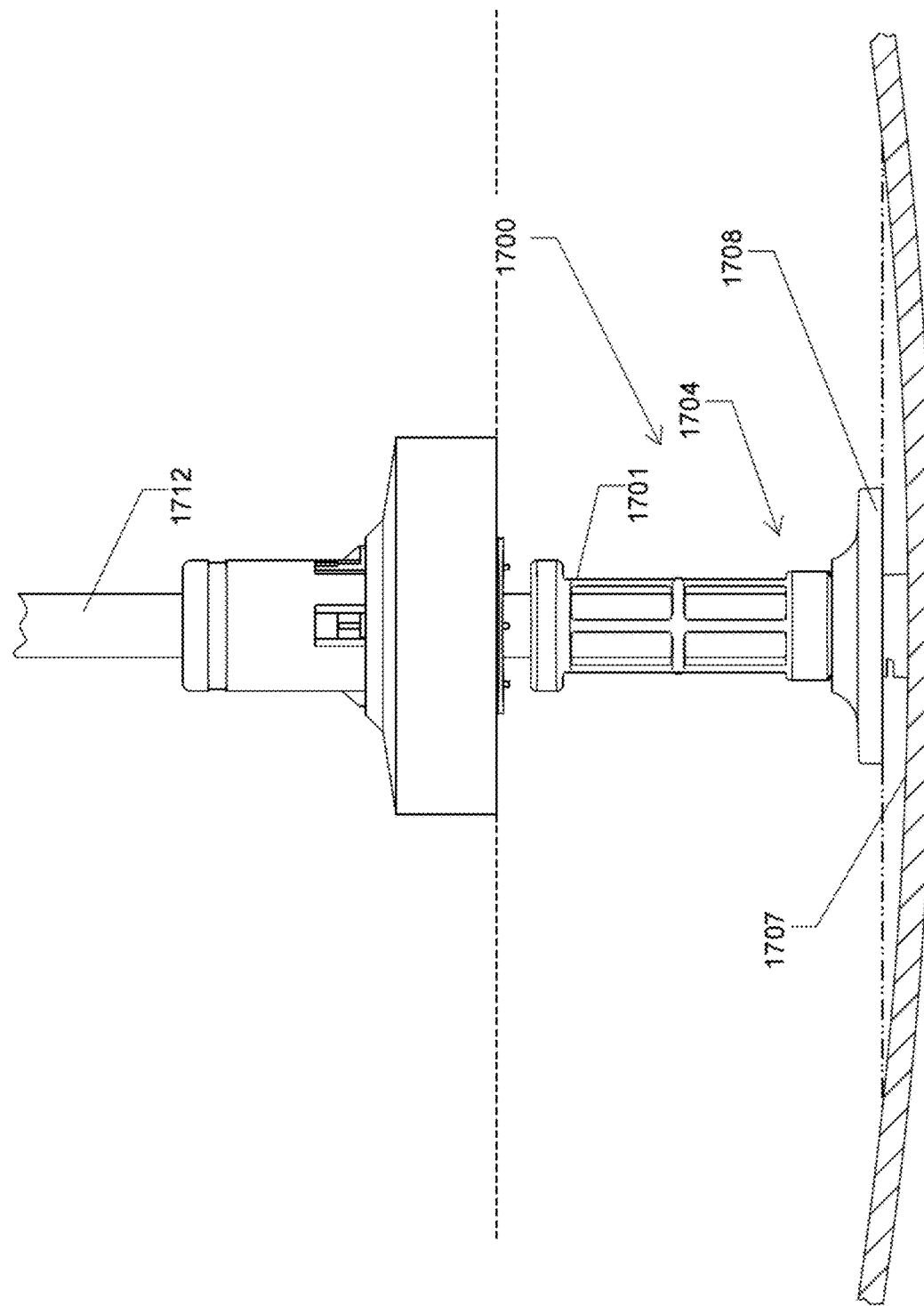
FIG. 43 is a radial elevation of the combination of FIG. 42 showing the low-level water sensor floating on a quantity of water and a product float floating on a quantity of fuel.

FIGS. 40 and 41 illustrate two further exemplary low level water sensor arrangements capable to providing outputs to, e.g., controller 102 to actuate filtration systems 200, 200', 200A, or 200B. Water sensor 900 illustrated in FIG. 40 incorporates a resistive or capacitive sensor into the bottom of a standard water/product float sensor such as the digital inventory and leak detection probes available from Franklin Fueling Systems of Madison, Wis. Water sensor 1000 shown in FIG. 41 addresses the problem of making a water float 1002 with a width W2 sufficient to pass through riser 702 but still be buoyant on a layer of water having a height of no more than 15/16 inch, ⅞ inch, 13/16 inch, ⅞ inch, 11/16 inch, ⅝ inch, 9/16 inch, ½ inch, 7/16 inch, ⅜ inch, 5/16 inch, ¼ inch, 3/16 inch, ⅛, or 1/16, or less by supporting float 1002 on spring 1004 at the distal most end of probe shaft 1006. Probe shaft 1006 includes an elongated magnetostrictive transducer capable of sensing the position of water float 1002 along the longitudinal axis of probe shaft 1006 via a magnet carried by float 1002 and providing the same in an output signal as described herein with respect to alternative embodiment low level water sensors, as described with alternative low level water sensor embodiments herein. Spring 1004 is arranged to compress only at the very end of travel of float 1002, i.e., only over a small distance (15/16 inch, ⅞ inch, 13/16 inch, ⅞ inch, 11/16 inch, ⅝ inch, 9/16 inch, ½ inch, 7/16 inch, ⅜ inch, 5/16 inch, ¼ inch, 3/16 inch, ⅛, or 1/16, or less) before reaching distal stop 1008, which defines a lower datum for water float 1002. Water float 1002 is a toroid with a central aperture to accommodate probe shaft 1006 and can, in use, be positioned as illustrated in FIG. 1 with respect to sensor 700.

EXAMPLES

1. Example 1: Degradation of Transmitted Light Intensity in Corrosive Environment Various plain steel samples were prepared as summarized in Table 1 below. Each sample was cut into a 1-inch square.

TABLE 1

| No. | Description | Dimensions |
| --- | --- | --- |
| 1 | Fine wire mesh | 60 × 60 mesh, 0.0075" wire diameter |
| 2 | Thick wire mesh | 14 × 14 mesh, 0.035" wire diameter |
| 3 | Perforated sheet | 0.033" hole diameter |

TABLE 1-continued

| No. | Description | Dimensions |
|---|---|---|
| 4 | Fine wire mesh | 30 × 30 mesh, 0.012" wire diameter |
| 5 | Perforated sheet | 0.024" hole diameter |

The samples were placed in a sealed glass container together with a 5% acetic acid solution. The samples were suspended on a non-corrosive, stainless steel platform over the acetic acid solution for exposure to the acetic acid vapor in the container. Select samples were removed from the container after about 23, 80, and 130 hours. Other samples were reserved as control samples.

Figure 8:
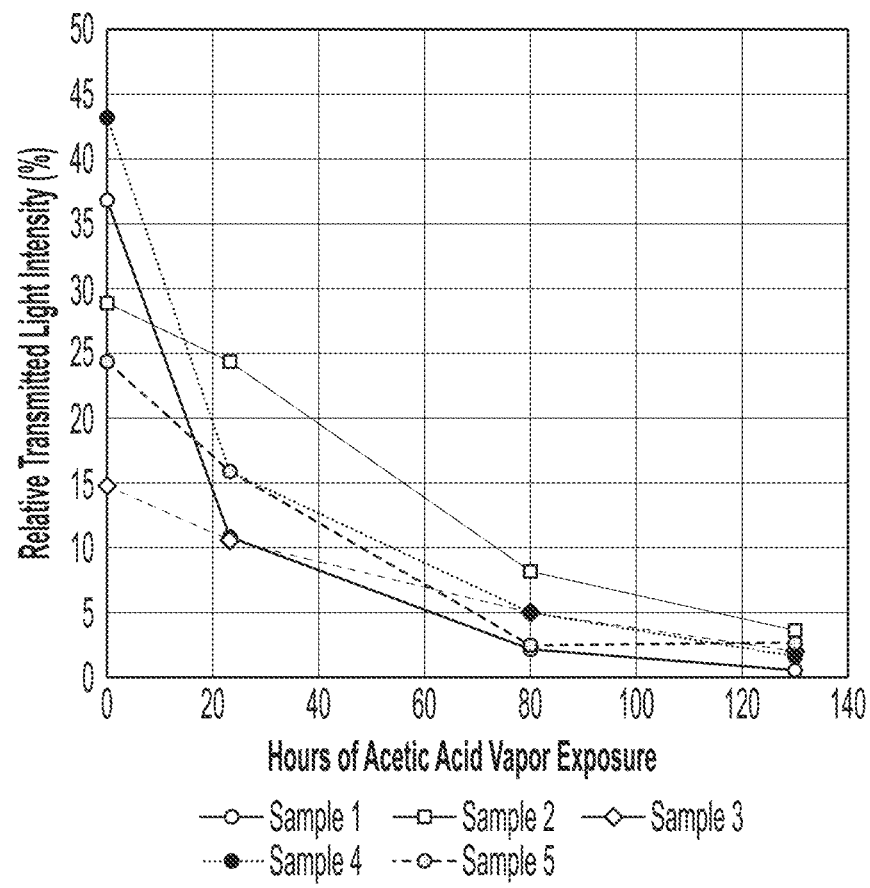
FIG. 8 is a graphical representation of the relative transmitted light intensity through each sample of Example 1 over time.
Figure 9:
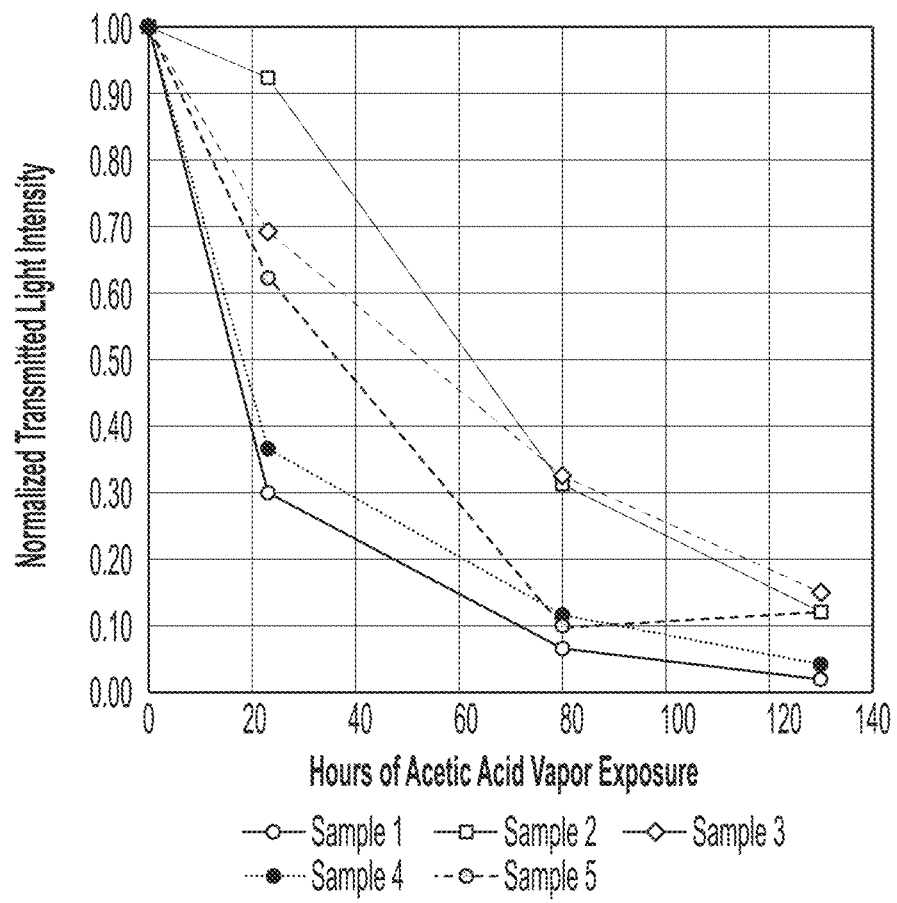
FIG. 9 is a graphical representation of the normalized transmitted light intensity through each sample of Example 1 over time.

Each sample was placed inside a holder and illuminated with a LED light source inside a tube to control light pollution. An ambient light sensor from ams AG was used to measure the intensity of the light passing through each sample. The results are presented in FIGS. 7-9. FIG. 7 includes photographs of the illuminated samples themselves. FIG. 8 is a graphical representation of the relative light intensity transmitted through each sample over time. FIG. 9 is a graphical representation of the normalized light intensity transmitted through each sample over time, with an intensity of 1.00 assigned to each control sample. As shown in FIGS. 7-9, all of the samples exhibited increased corrosion and decreased light transmission over time. The fine wire mesh samples (Sample Nos. 1 and 4) exhibited the most significant corrosion over time.

Figure 10:
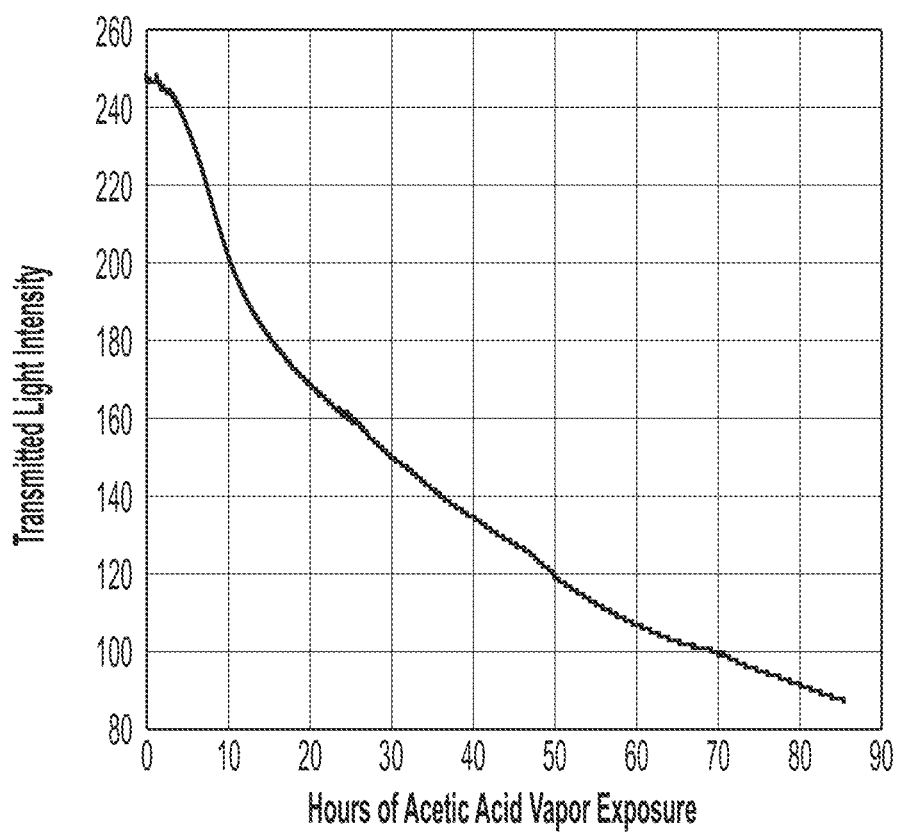
FIG. 10 is a graphical representation of the transmitted light intensity through the corrosive sample tested in Example 2 over time.

2. Example 2: Real-Time Degradation of Transmitted Light Intensity in Corrosive Environment Sample No. 4 of Example 1 was placed inside a sealed plastic bag together with a paper towel that had been saturated with a 5% acetic acid solution. The sample was subjected to illumination testing in the same manner as Example 1, except that the sample remained inside the sealed bag during testing. The results are presented in FIG. 10, which is a graphical representation of the actual light intensity transmitted through the sample over time. Like Example 1, the sample exhibited increased corrosion and decreased light transmission over time.

3. Example 3: Humidity Control with Desiccant

A turbine sump having a volume of 11.5 cubic feet and a stable temperature between about 65° F. and 70° F. was humidified to about 95% using damp rags. The rags were then removed from the humidified turbine sump. A desiccant bag was placed inside the humidified turbine sump, which was then sealed closed. The desiccant bag contained 125 g of calcium chloride with a gelling agent to prevent formation of aqueous calcium chloride.

Figure 20:
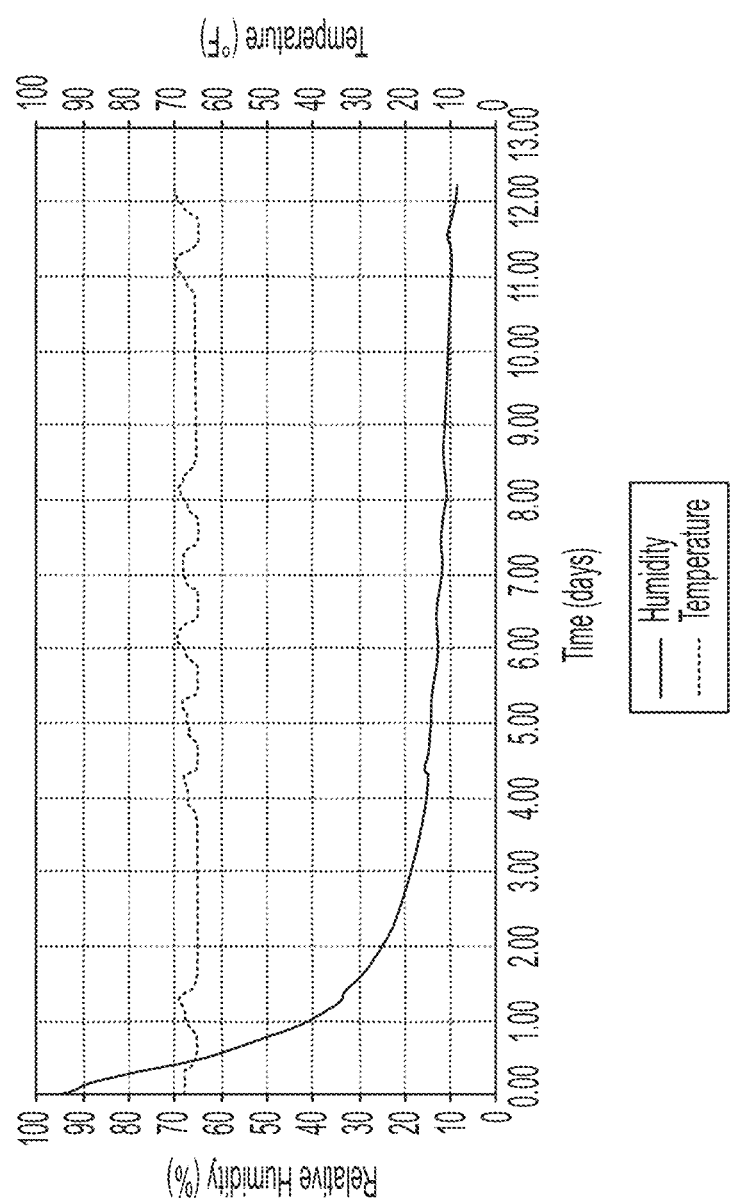
FIG. 20 is a graphical representation of the relative humidity and temperature over time in a turbine sump with a desiccant.

The relative humidity and temperature in the turbine sump were measured over time, as shown in FIG. 20. After 1 day, the desiccant had adsorbed enough moisture to decrease the relative humidity to about 40%. After 3 days, the desiccant had adsorbed enough moisture to decrease the relative humidity beneath about 20%. The relative humidity eventually decreased beneath 10%.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A water float, comprising:
 a float base; and
 a frame including two frame halves, each frame half including at least one snap connector positioned within a channel defined by the frame half for indexing the frame to the float base, the at least one snap connector including a ramped distal end;
 wherein the float base includes a plurality of stops extending radially inwardly into a central aperture of the float base, each of the plurality of stops including a ramped proximal end; and
 wherein the ramped distal end of the at least one snap connector of each frame half contacts a ramped proximal end of one of the plurality of stops upon insertion of the frame into the central aperture of the float base, and flexes until an outwardly directed shoulder of the at least one snap connector passes the stop.

2. The water float of claim 1, wherein each of the at least one snap connector includes an outer surface that tapers radially outwardly from the shoulder to resist movement of the float base upwardly relative to the frame.

3. The water float of claim 1, wherein the frame includes a plurality of water float feet that extend distally from the float base when the frame is connected to the float base, the plurality of water float feet being configured to engage a foot coupled to a magnetostrictive probe.

4. The water float of claim 1, wherein the frame includes a plurality of frame spacers that extend radially inwardly from the frame and are configured to contact a magnetostrictive probe as the frame moves relative to the magnetostrictive probe.

5. The water float of claim 1, wherein the water float has a specific gravity such that it is buoyant in water collected at the floor of a tank of no more than 0.25 inches.

6. The water float of claim 1, wherein the water float has a diameter of 2.75 inches or less.

7. The water float of claim 1, wherein each frame half includes one of a plurality of attachment bosses or a plurality of attachment apertures, the plurality of attachment bosses forming an interference fit with the plurality of attachment apertures, thereby connecting one frame half to the other frame half.

8. The water float of claim 1, further including a water float magnet, wherein a top end of each frame half includes an annular channel sized to hold the water float magnet when the frame halves are connected to one another.

9. The water float of claim 8, further comprising at least one ballast ring, wherein a bottom end of each frame half includes a ballast receiver including an annular groove sized to receive the at least one ballast ring.

10. The water float of claim 9, wherein the float magnet and the at least one ballast ring each include a central opening sized to receive a magnetostrictive probe.

11. A water float, comprising:
 a float base; and
 a frame including two frame halves, each frame half including at least one friction connector extending outwardly from the frame half;
 wherein the float base includes a central aperture;
 wherein upon insertion of the frame into the central aperture of the float base, the at least one friction connectors frictionally engage the float base to inhibit movement of the float base relative to the frame; and wherein the frame includes a plurality of water float feet that extend distally from the float base when the frame is connected to the float base, the plurality of water float feet being configured to engage a foot coupled to a magnetostrictive probe.

12. The water float of claim 11, wherein the frame includes a plurality of frame spacers that extend radially inwardly from the frame and are configured to contact a magnetostrictive probe as the frame moves relative to the magnetostrictive probe.

13. The water float of claim 11, wherein the water float has a specific gravity such that it is buoyant in water collected at the floor of a tank of no more than 0.25 inches.

14. The water float of claim 11, wherein each frame half includes one of a plurality of attachment bosses or a plurality of attachment apertures, the plurality of attachment bosses forming an interference fit with the plurality of attachment apertures, thereby connecting one frame half to the other frame half.

15. The water float of claim 11, further including a water float magnet, wherein a top end of each frame half includes an annular channel sized to hold the water float magnet when the frame halves are connected to one another.

16. The water float of claim 15, further comprising at least one ballast ring, wherein a bottom end of each frame half includes a ballast receiver including an annular groove sized to receive the at least one ballast ring.

17. The water float of claim 15, wherein the float magnet and the at least one ballast ring each include a central opening sized to receive a magnetostrictive probe.

* * * * *